United States Patent
Yamaya

(10) Patent No.: US 11,376,090 B2
(45) Date of Patent: Jul. 5, 2022

(54) ENDOSCOPE, AND ENDOSCOPE SYSTEM

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 429 days.

(21) Appl. No.: 16/133,832

(22) Filed: Sep. 18, 2018

(65) Prior Publication Data

US 2019/0015172 A1  Jan. 17, 2019

Related U.S. Application Data

(63) Continuation of application No. PCT/JP2017/005523, filed on Feb. 15, 2017.

(30) Foreign Application Priority Data

Mar. 23, 2016 (JP) .............................. JP2016-058991

(51) Int. Cl.
*A61B 90/00* (2016.01)
*A61B 1/00* (2006.01)
(Continued)

(52) U.S. Cl.
CPC .......... *A61B 90/03* (2016.02); *A61B 1/00098* (2013.01); *A61B 1/00101* (2013.01);
(Continued)

(58) Field of Classification Search
CPC . A61B 90/03; A61B 1/00098; A61B 1/00101; A61B 1/018; A61B 2090/035; G02B 23/2476
(Continued)

(56) References Cited

U.S. PATENT DOCUMENTS

| 5,460,168 A * | 10/1995 | Masubuchi ........ | A61B 1/00142 600/123 |
| 2007/0270637 A1* | 11/2007 | Takemoto .......... | A61B 17/0469 600/104 |
| 2016/0270637 A1* | 9/2016 | Tanaka ............... | A61B 1/00098 |

FOREIGN PATENT DOCUMENTS

| JP | 04218134 A | * | 8/1992 | ......... A61B 1/00098 |
| JP | H04-314439 A | | 11/1992 | |

(Continued)

OTHER PUBLICATIONS

International Search Report dated May 16, 2017 issued in PCT/JP2017/005523.
(Continued)

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An endoscope includes: a rigid distal structure portion; a rotational portion; an exterior member; a bearing opposed to the exterior member and recessed from an outer surface of the distal structure portion, the bearing being; and a preventing portion. The bearing is configured to receive and support the rotational shaft and to displace the rotational shaft from the distal structure portion by the exterior member being removed from the distal structure portion. The preventing portion provided on one of the rotational portion and the distal structure portion, and configured to prevent disengagement of the rotational portion by coming in contact with the other of the rotational portion and the distal structure portion when the rotational shaft is displaced from the bearing.

16 Claims, 38 Drawing Sheets

(51) Int. Cl.
 *G02B 23/24* (2006.01)
 *A61B 1/018* (2006.01)
(52) U.S. Cl.
 CPC .......... *G02B 23/2476* (2013.01); *A61B 1/018* (2013.01); *A61B 2090/035* (2016.02)
(58) Field of Classification Search
 USPC ................................................ 600/127, 129
 See application file for complete search history.

(56) References Cited

FOREIGN PATENT DOCUMENTS

| | | | | |
|---|---|---|---|---|
| JP | H06-315458 | A | | 11/1994 |
| JP | H06-315461 | A | | 11/1994 |
| JP | H07-000303 | U | | 1/1995 |
| JP | H08-056900 | A | | 3/1996 |
| JP | H08-182648 | A | | 7/1996 |
| JP | H09-253036 | A | | 9/1997 |
| JP | 10118014 | A | * | 5/1998 |
| JP | 10127578 | A | * | 5/1998 |
| JP | H10-127578 | A | | 5/1998 |
| JP | 2003-102668 | A | | 4/2003 |
| JP | 2006288756 | A | * | 10/2006 ......... A61B 1/00098 |
| JP | 2007-289434 | A | | 11/2007 |
| JP | 2009219572 | A | * | 10/2009 |
| WO | WO 2013/084561 | A1 | | 6/2013 |

OTHER PUBLICATIONS

English translation of International Preliminary Report on Patentability dated Oct. 4, 2018 together with the Written Opinion in related International Application No. PCT/JP2017/005523.

* cited by examiner

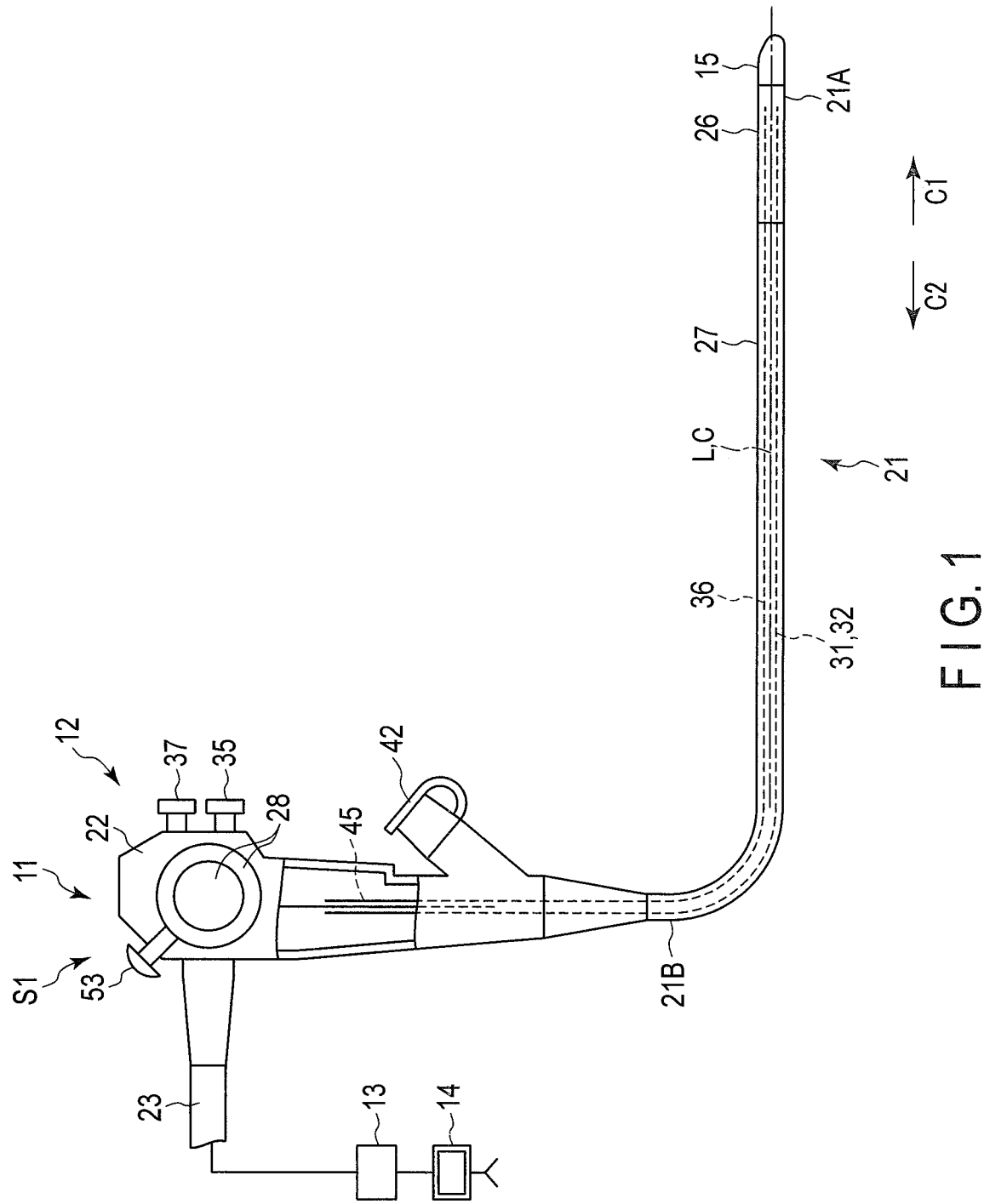
F I G. 1

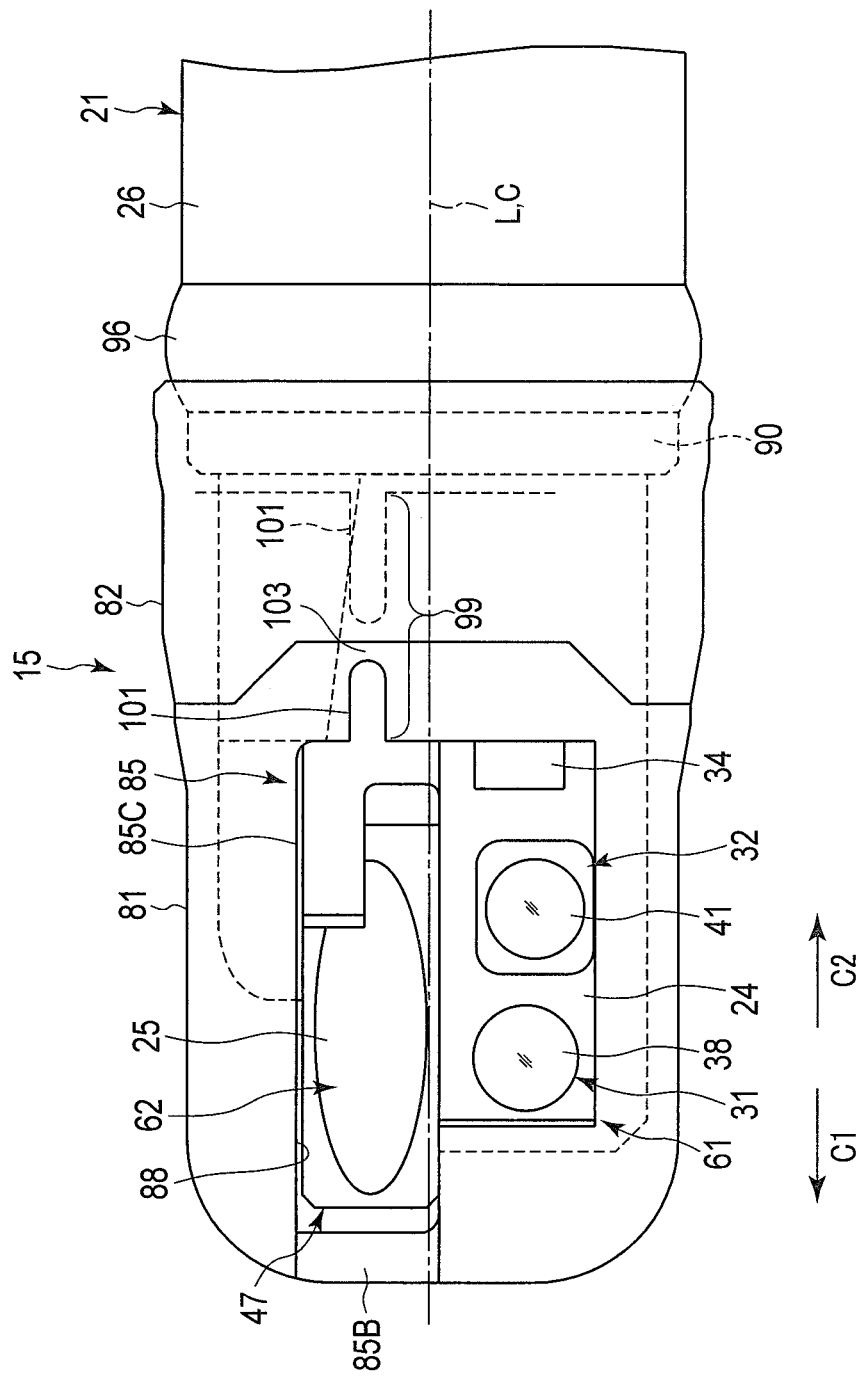
F I G. 2

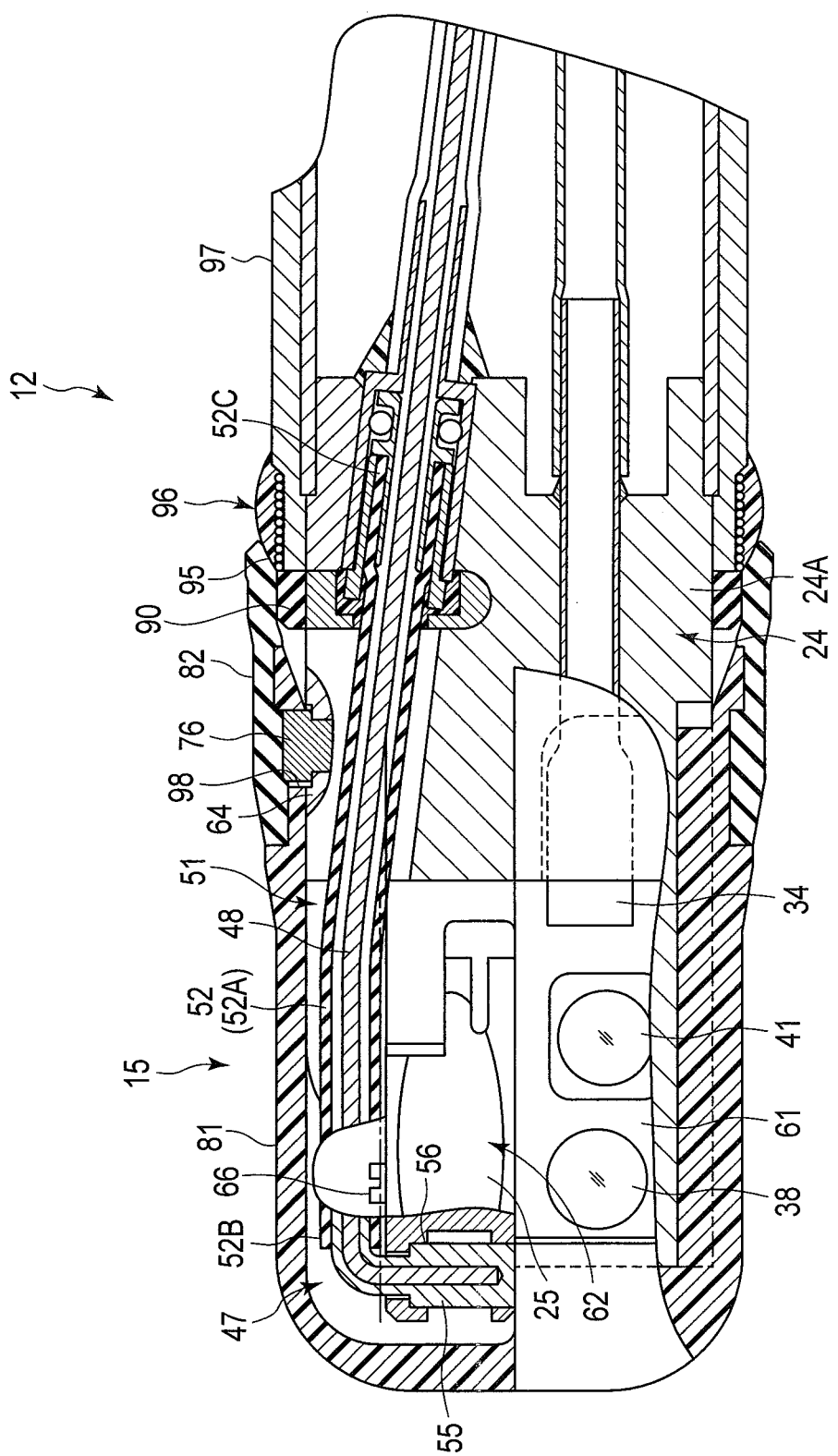
F I G. 5

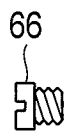
F I G. 8D
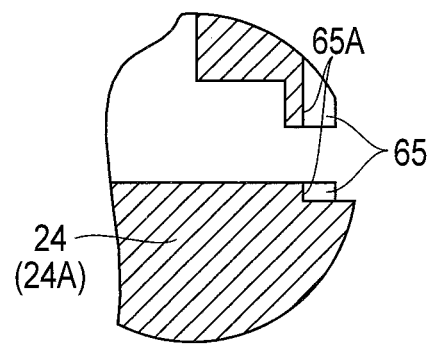
F I G. 8E
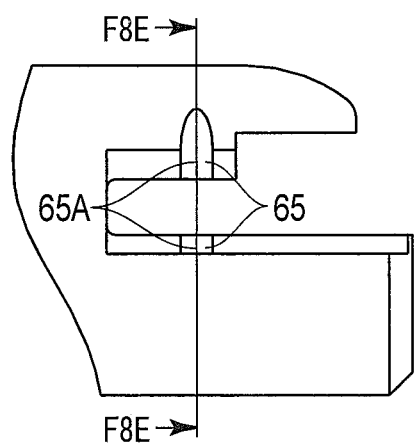
F I G. 8F

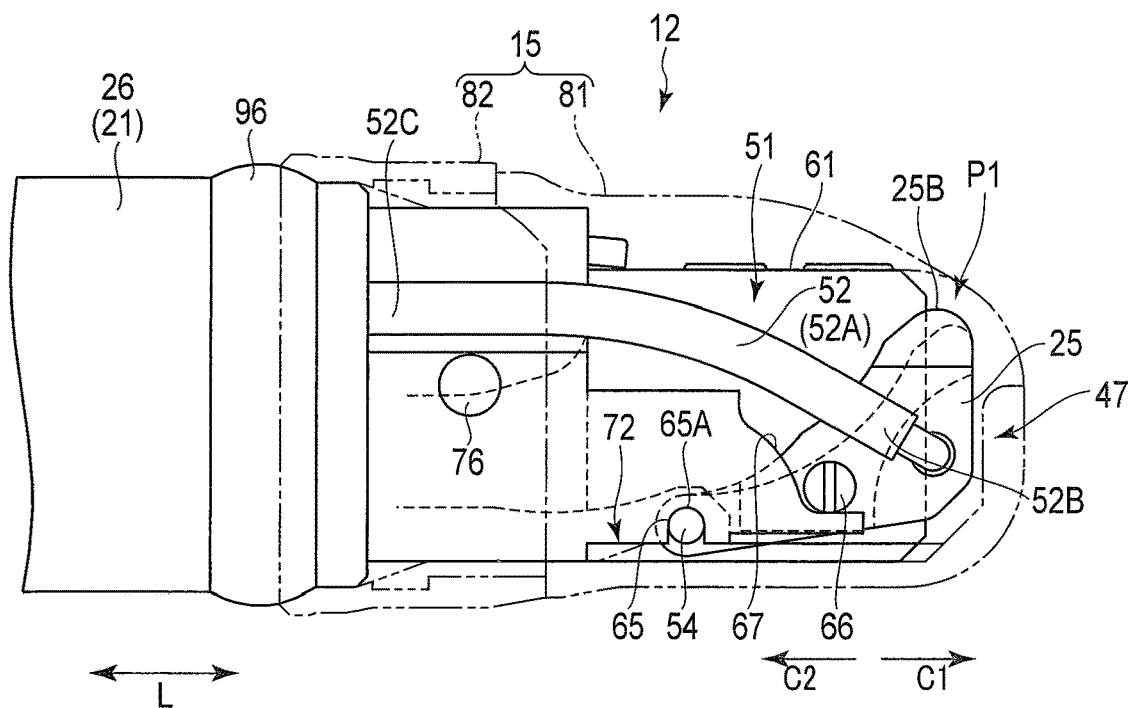
F I G. 11
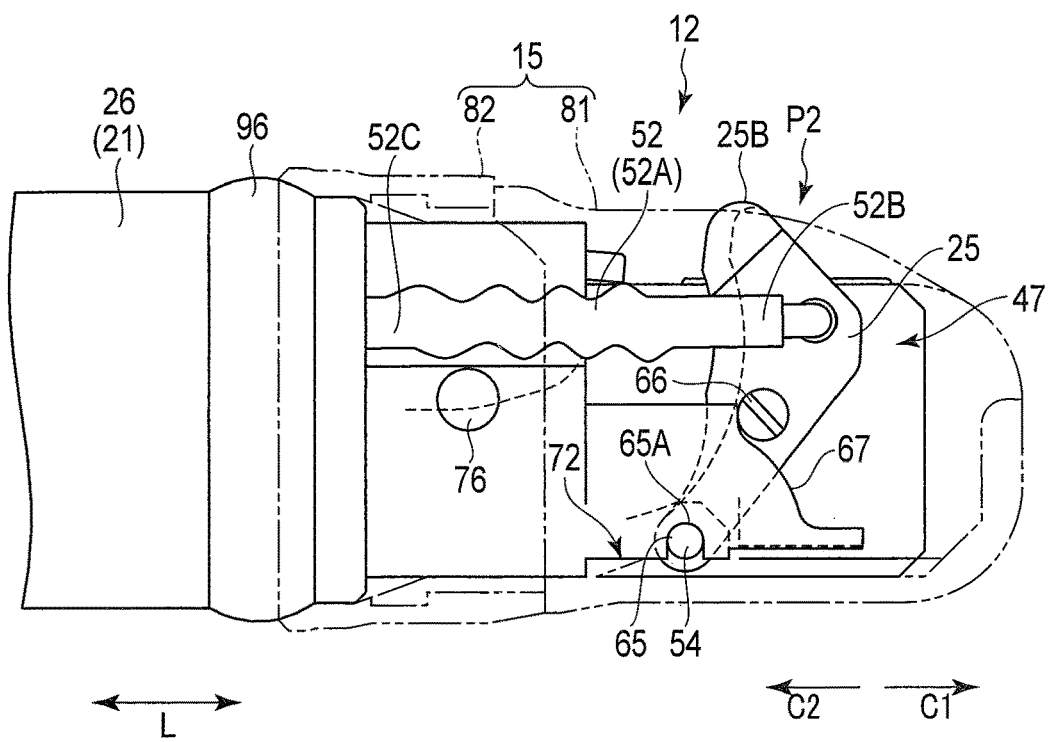
F I G. 12

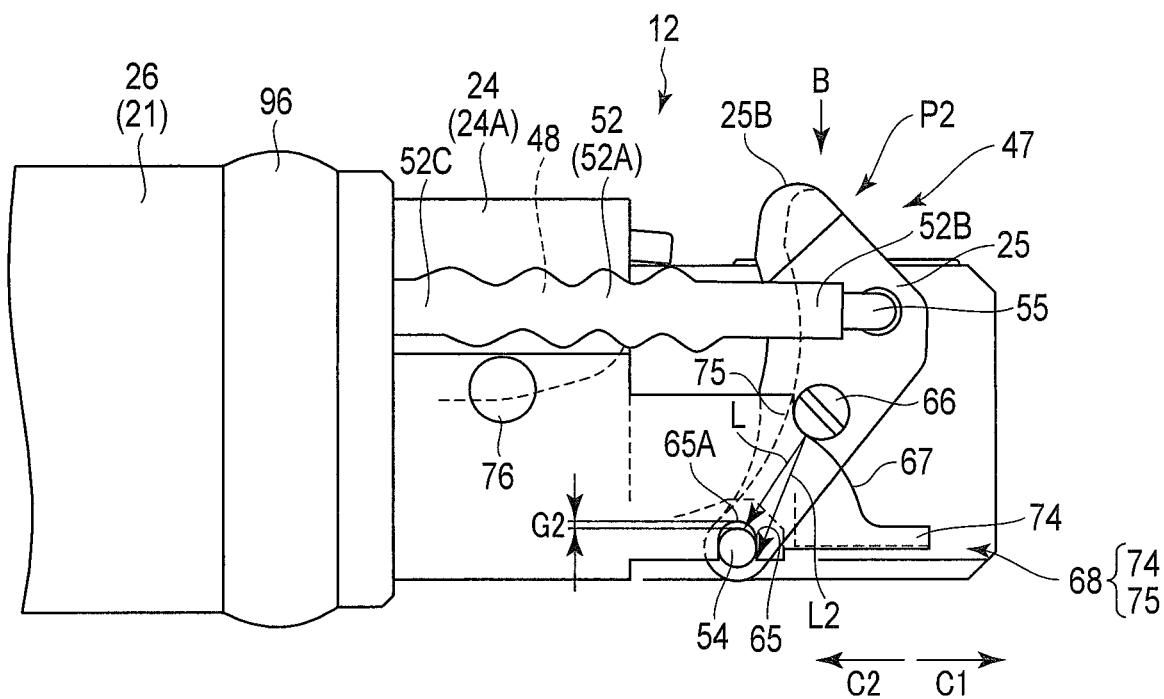
F I G. 14

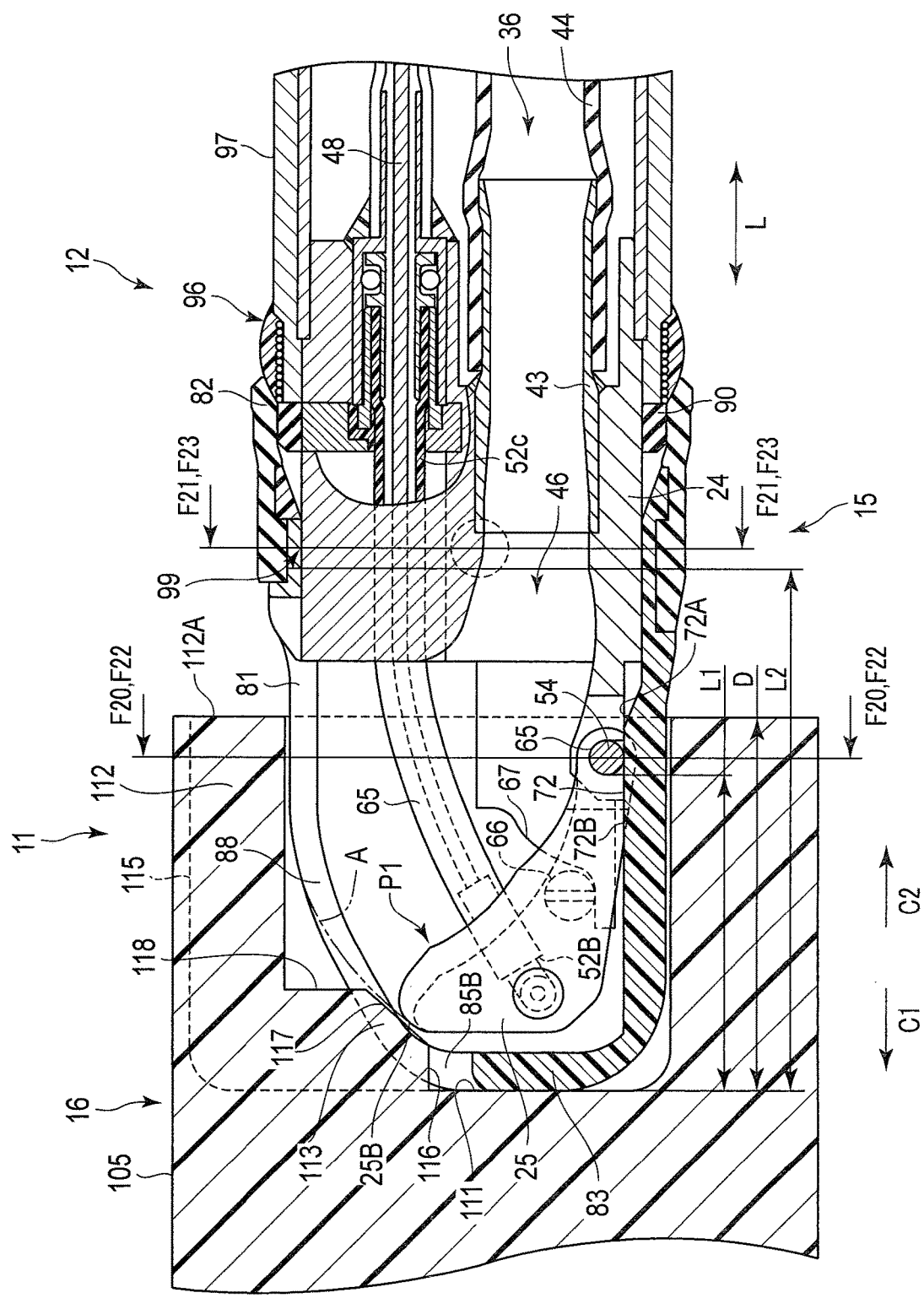
F I G. 19

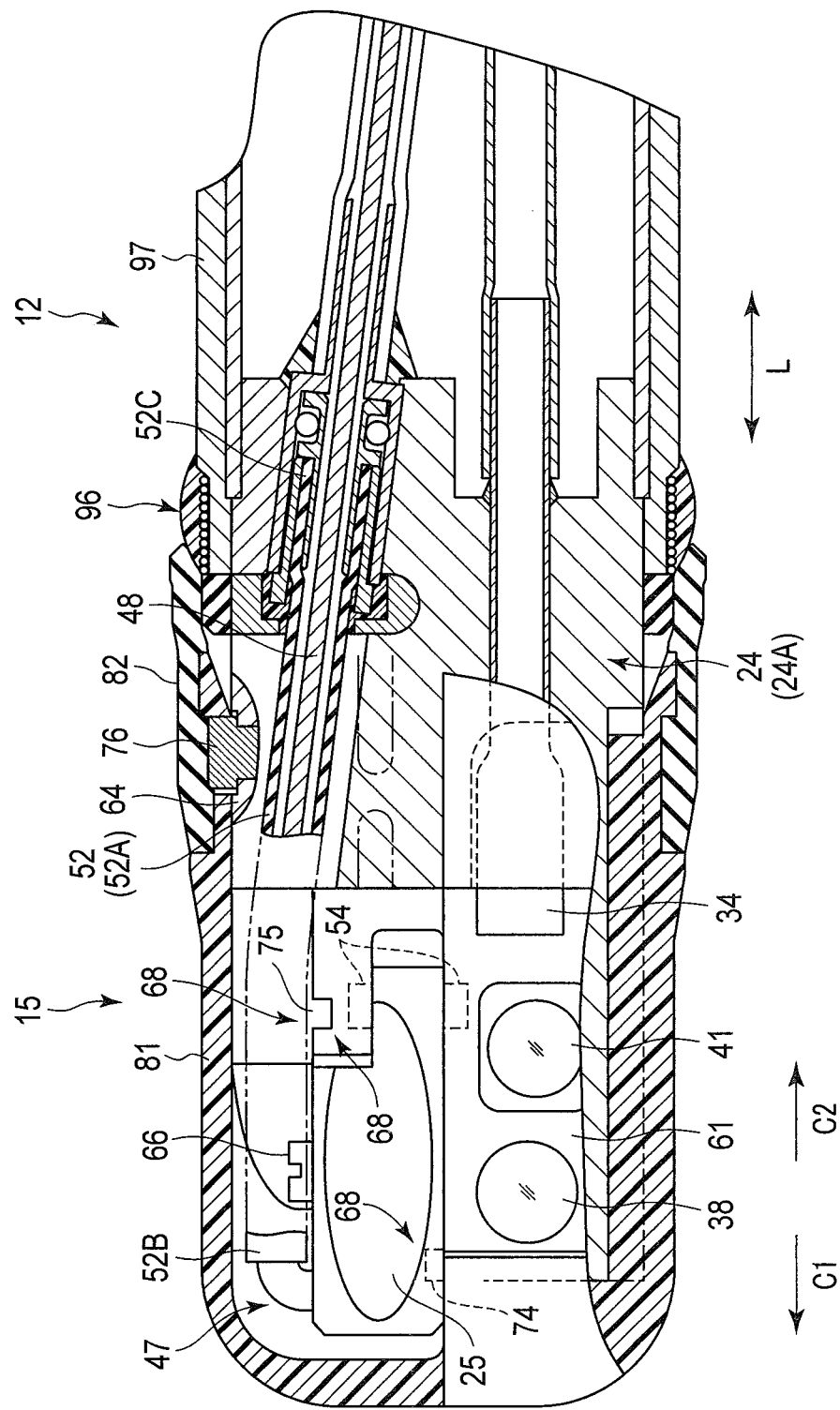
F I G. 24

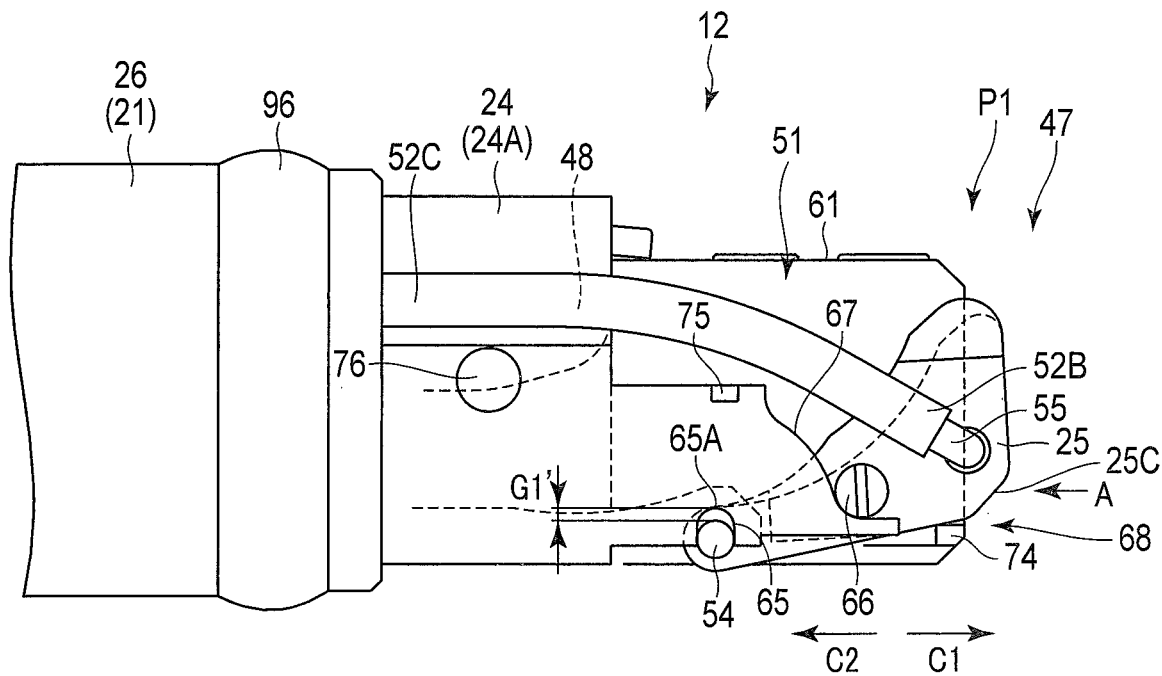
F I G. 27
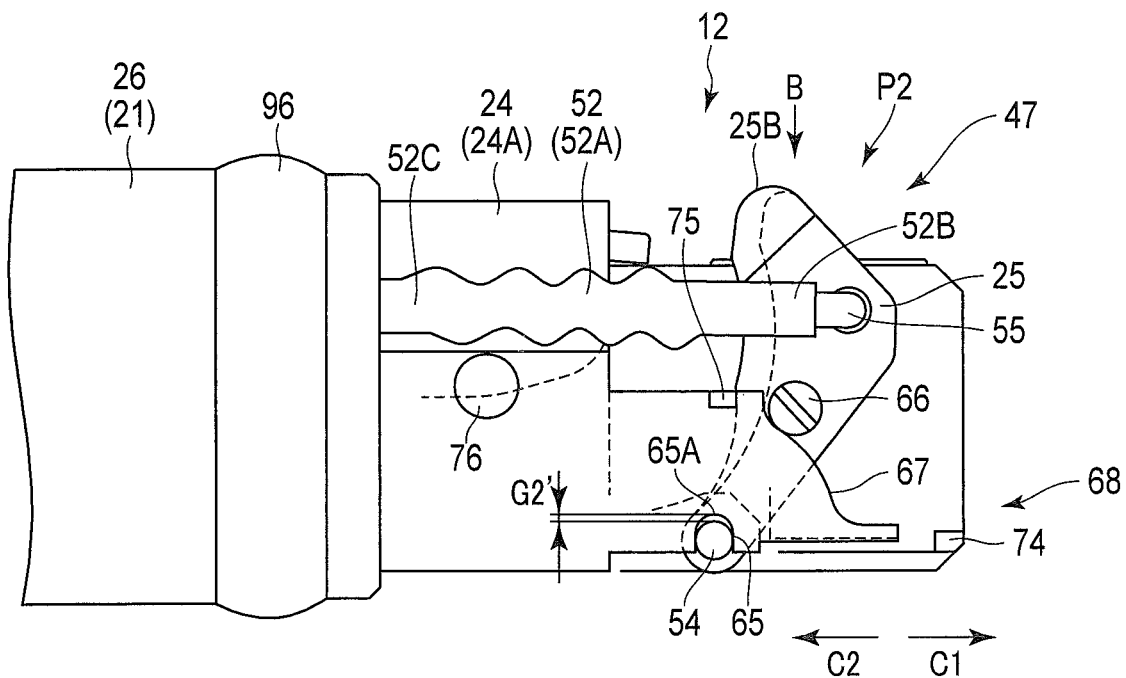
F I G. 28

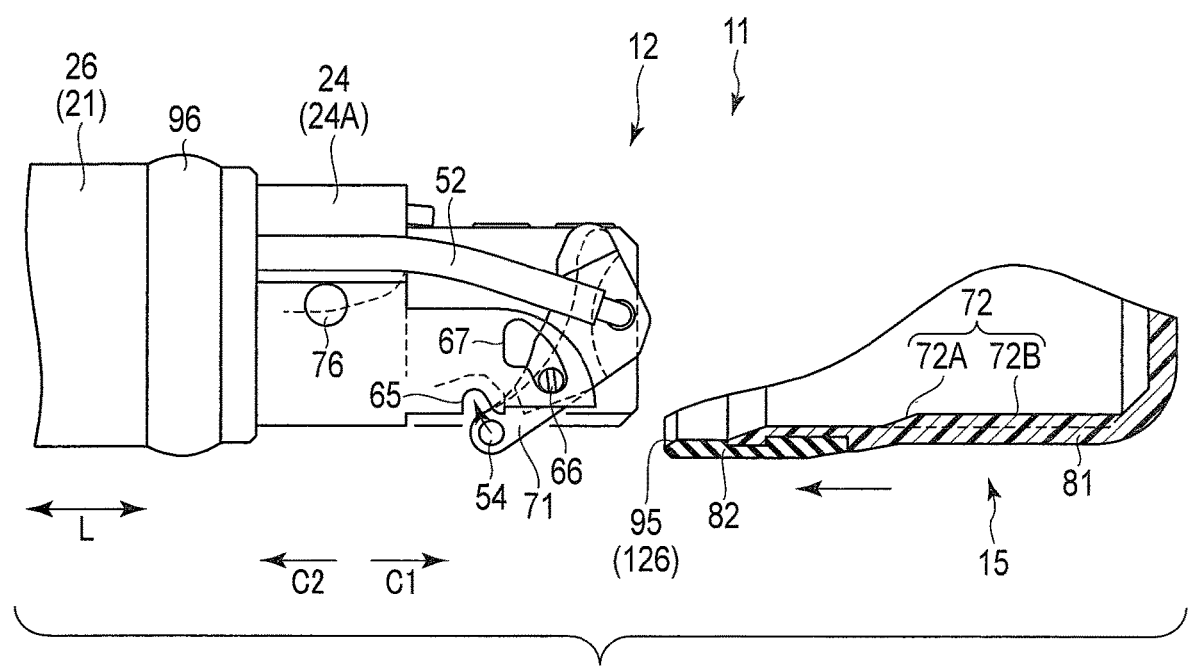
F I G. 44

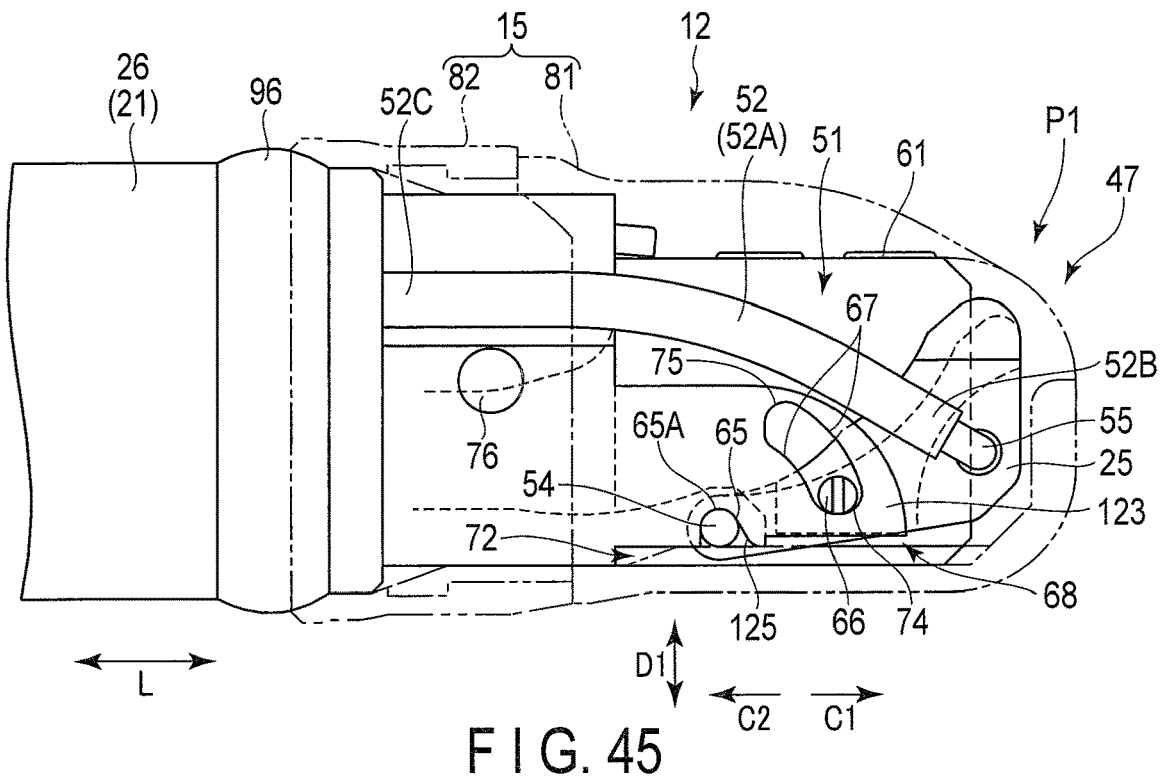
F I G. 45
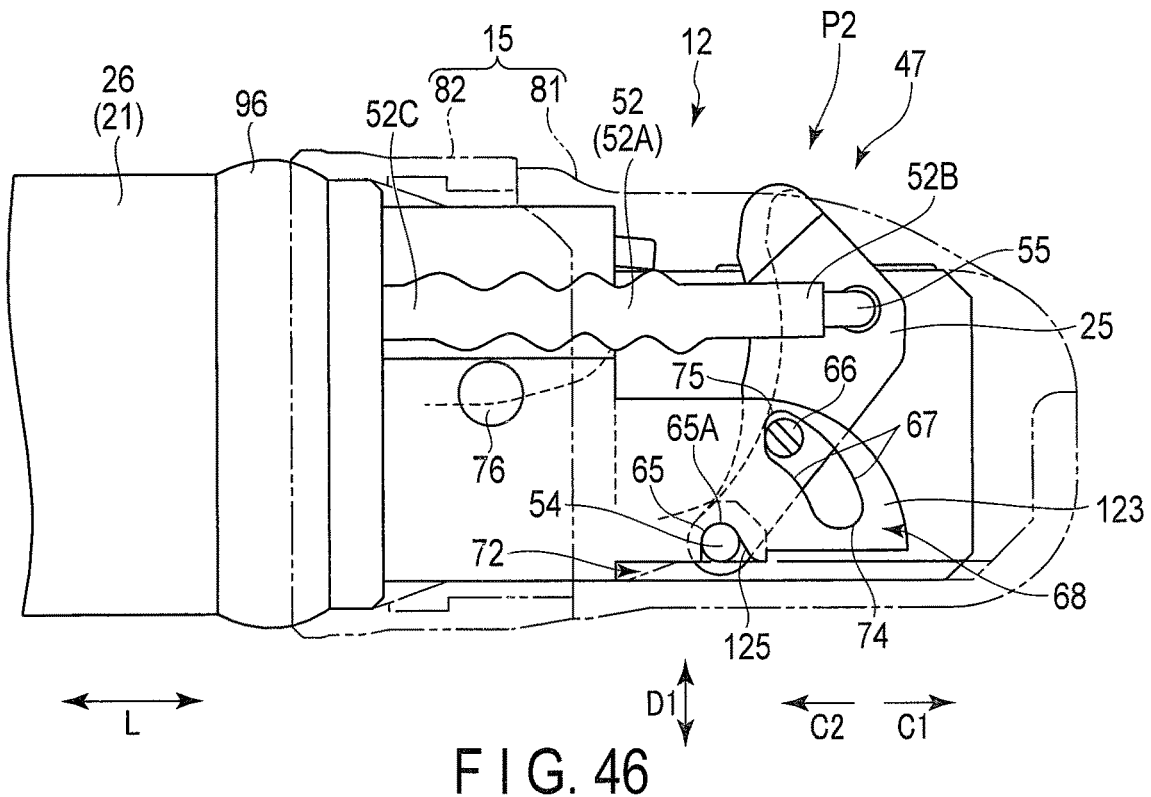
F I G. 46

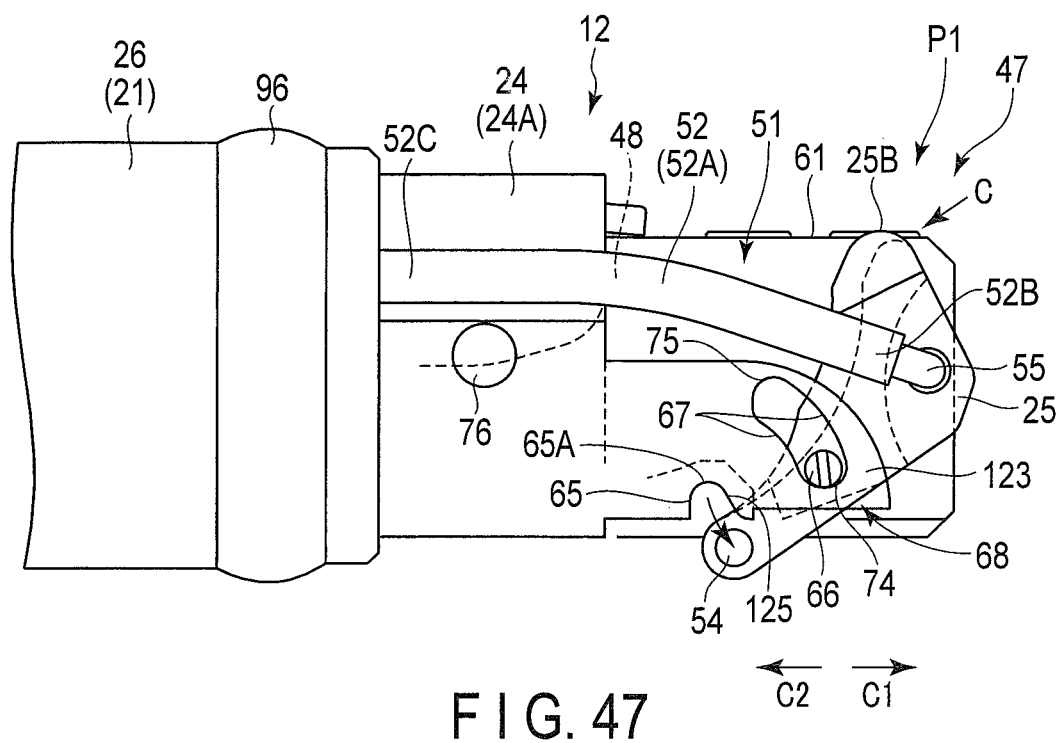
F I G. 47
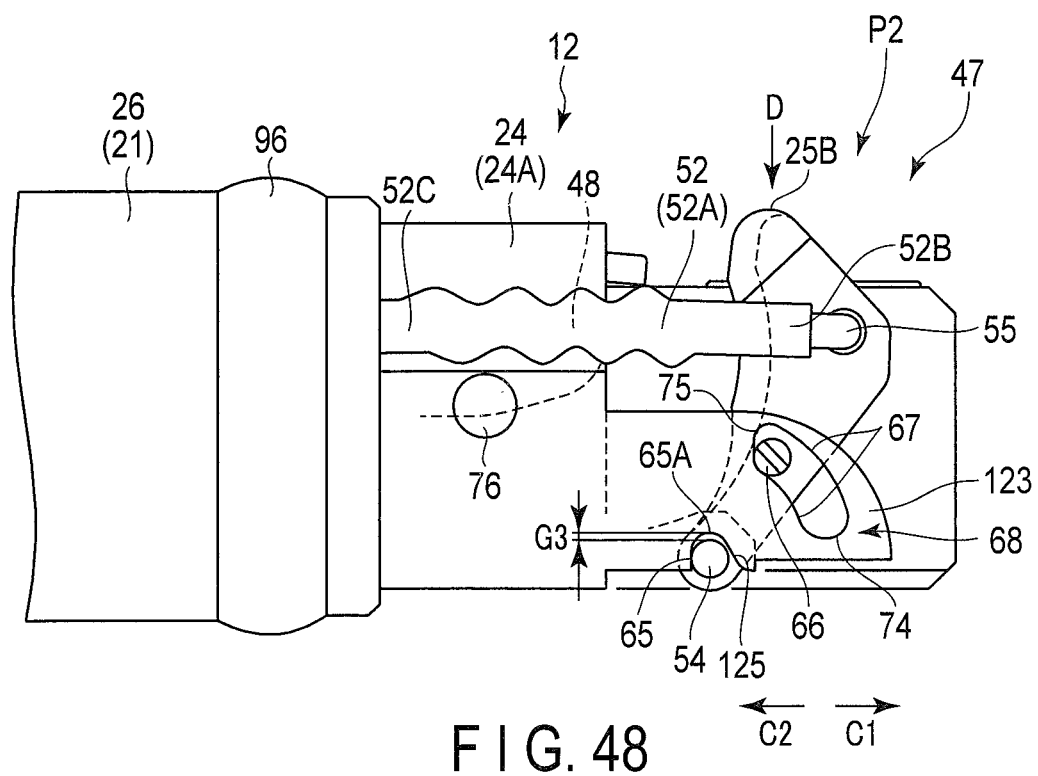
F I G. 48

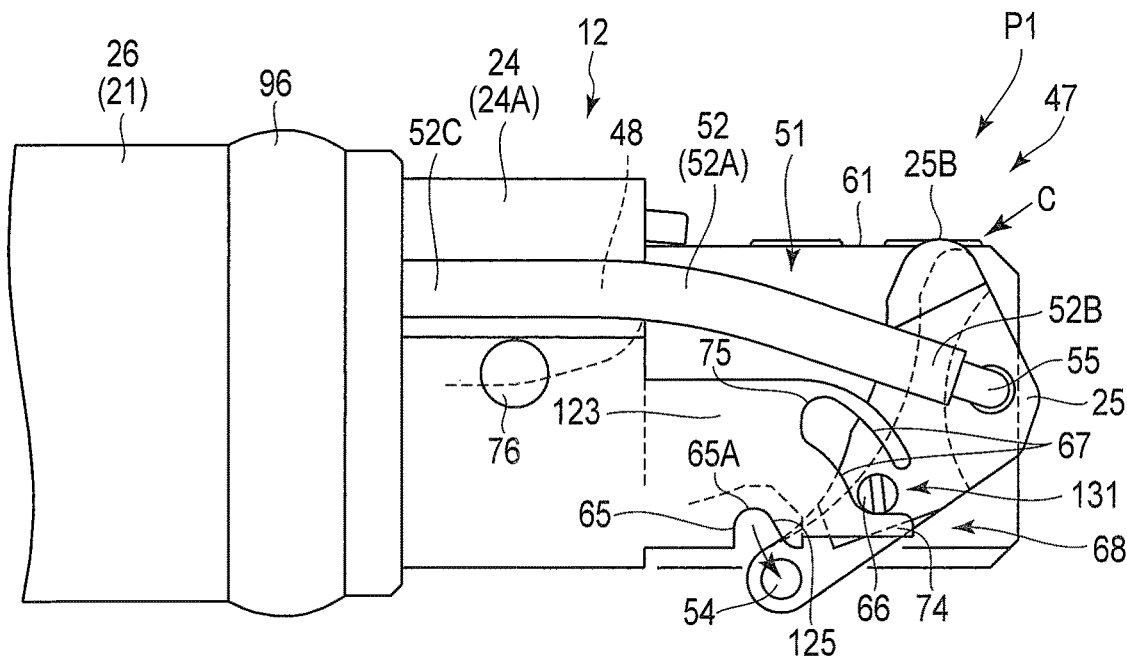
F I G. 52
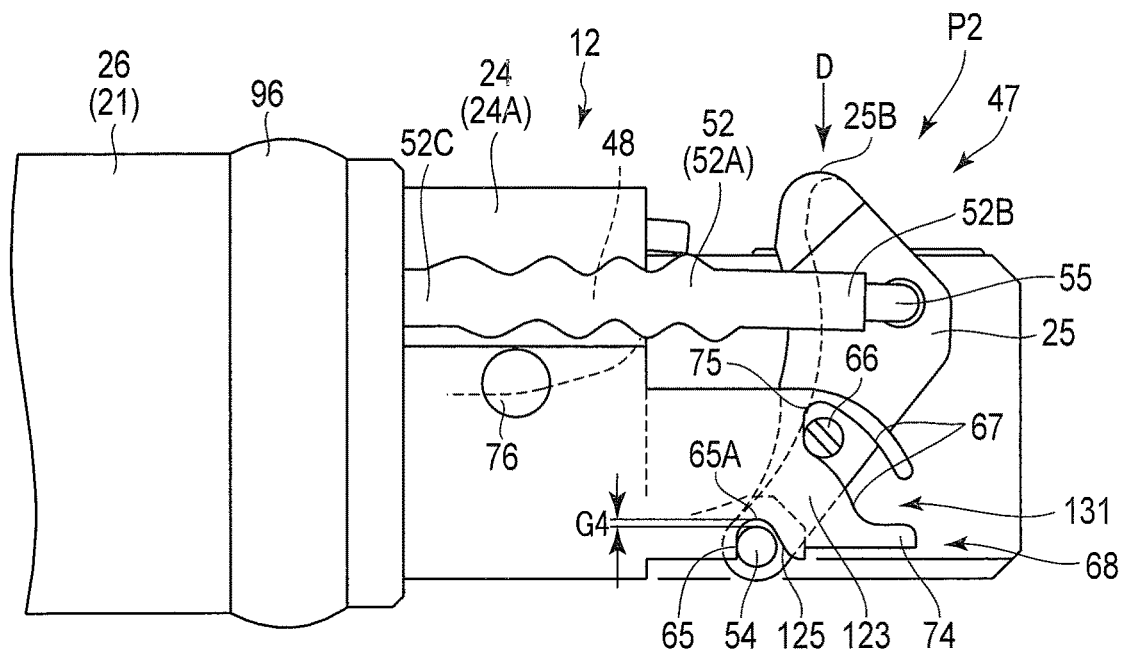
F I G. 53

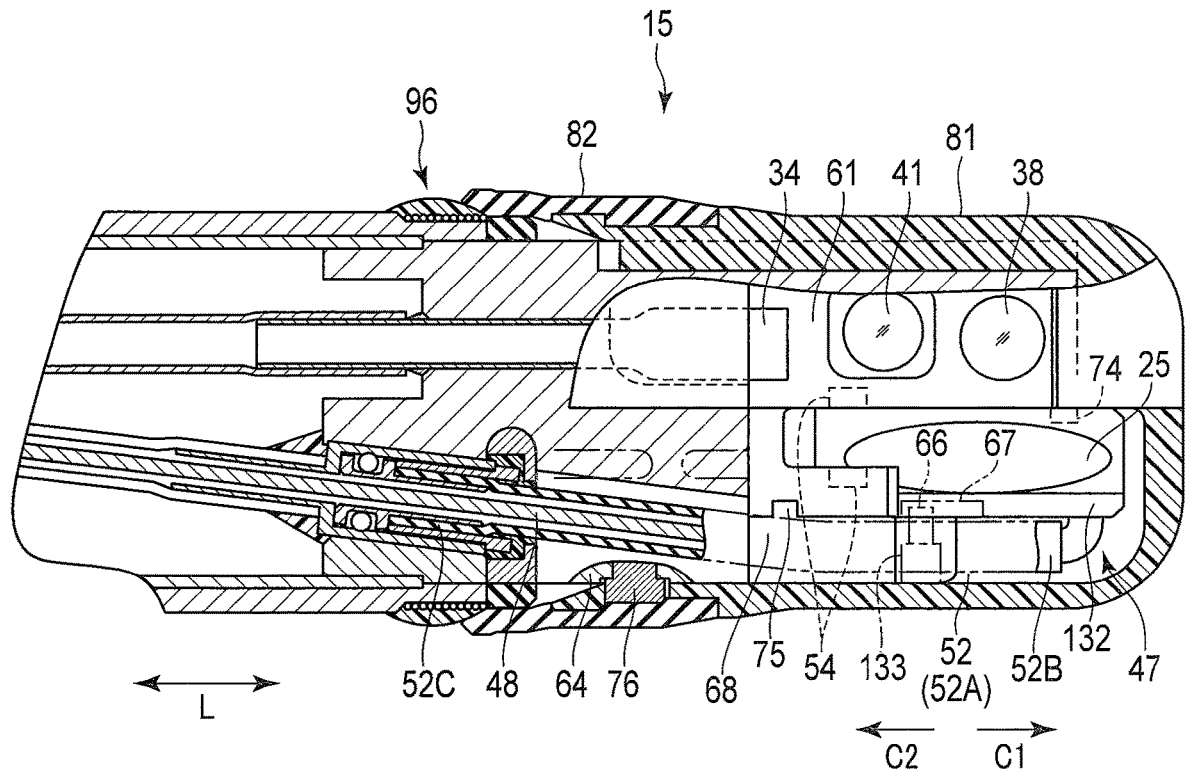
F I G. 56
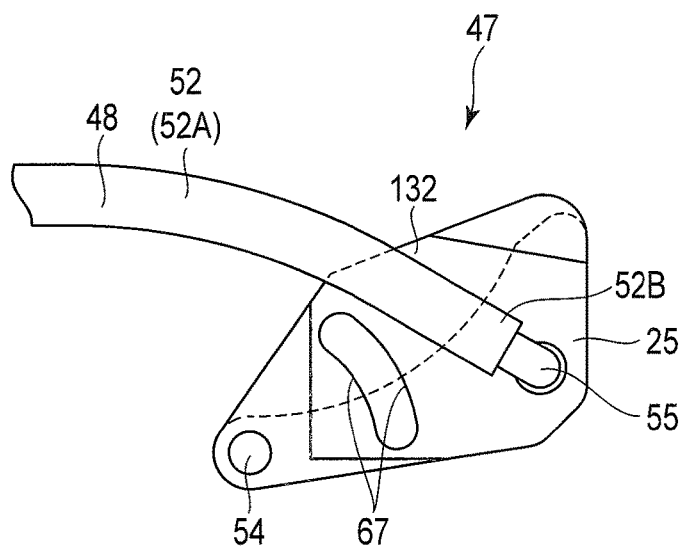
F I G. 57

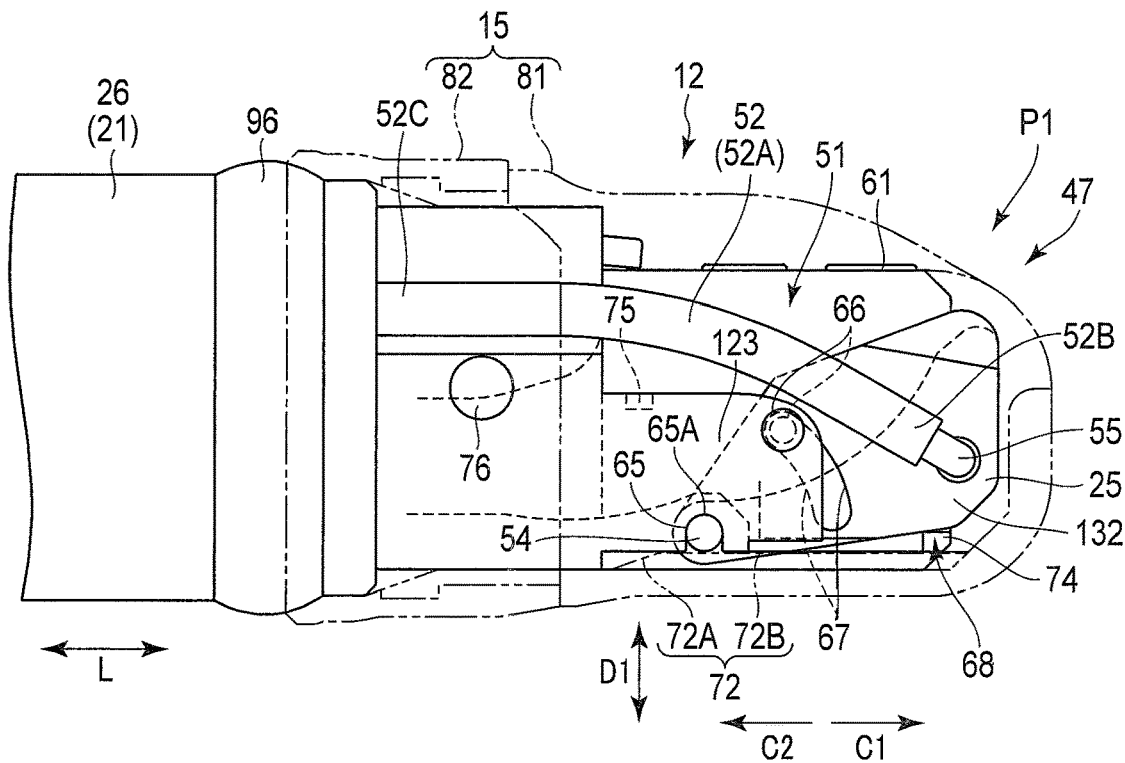
F I G. 58
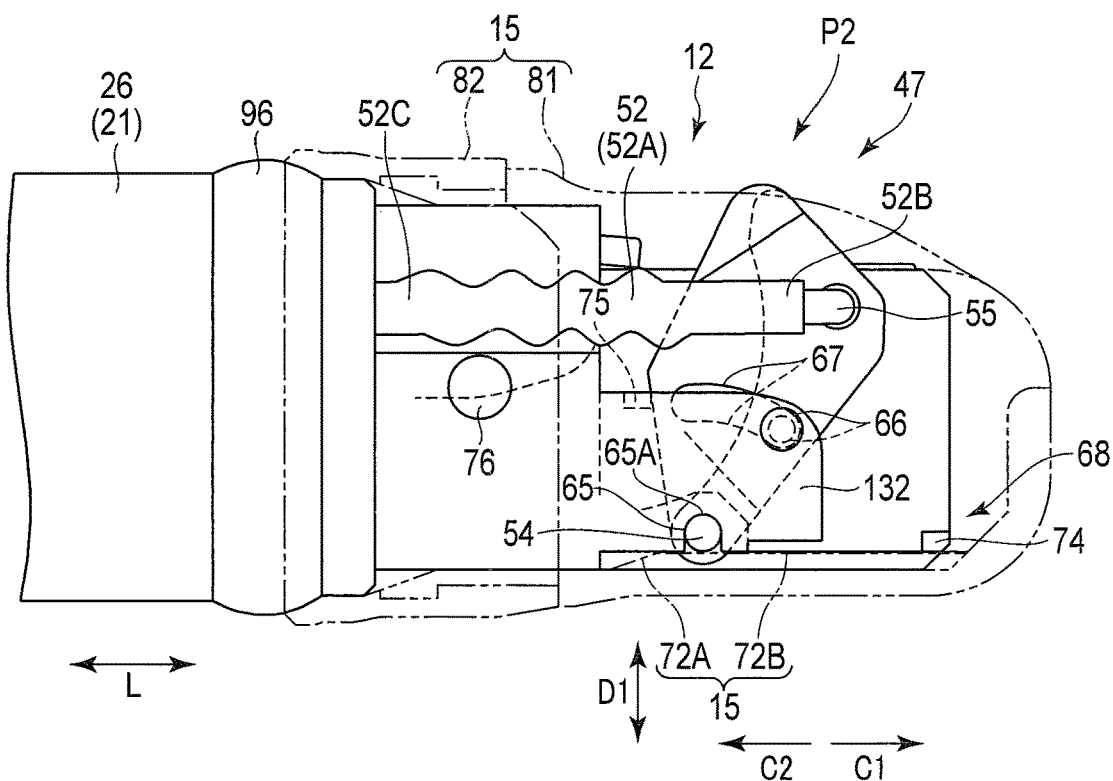
F I G. 59

ENDOSCOPE, AND ENDOSCOPE SYSTEM

CROSS-REFERENCE TO RELATED APPLICATIONS

This application is a Continuation Application of PCT Application No. PCT/JP2017/005523, filed Feb. 15, 2017 and based upon and claiming the benefit of priority from prior Japanese Patent Application No. 2016-058991, filed Mar. 23, 2016, the entire contents of all of which are incorporated herein by reference.

BACKGROUND OF THE INVENTION

1. Field of the Invention

The present invention relates to an endoscope including a rotational portion which rotates relative to a distal structure portion, and an endoscope system.

2. Description of the Related Art

For example, patent document 1 discloses an endoscope including a cap which is attached to a distal structure portion of the endoscope. Usually, in the endoscope, such a cap is provided, and the surrounding of the distal structure portion is covered by the cap. By this structure, a mucous membrane of a body cavity of a patient is protected.

CITATION LIST

Patent Literature

Patent document 1: Jpn. Pat. Appln. KOKAI Publication No. H9-253036

SUMMARY

One embodiment of an endoscope comprising: a rigid distal structure portion provided on a distal side of an insertion section which is inserted in a subject; a rotational portion including a rotational shaft which is held to be rotatable relative to the distal structure portion, and configured to rotate about the rotational shaft; an exterior member detachably attached to the distal structure portion; a bearing opposed to the exterior member and recessed from an outer surface of the distal structure portion, the bearing being configured to receive and support the rotational shaft and to displace the rotational shaft from the distal structure portion by the exterior member being removed from the distal structure portion; and a preventing portion provided on one of the rotational portion and the distal structure portion, and configured to prevent disengagement of the rotational portion by coming in contact with the other of the rotational portion and the distal structure portion when the rotational shaft is displaced from the bearing.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view illustrating an endoscope system and an endoscope according to an embodiment.

FIG. 2 is a schematic plan view illustrating a distal structure portion of the endoscope illustrated in FIG. 1, and a cover which covers the distal structure portion.

FIG. 5 is a partially cut-out cross-sectional view illustrating the distal structure portion illustrated in FIG. 2, the cover and a wire, FIG. 5 being taken by a plane along the wire.

FIG. 8D is a side view of the preventing portion (screw) which is fastened in the screw hole of the pivot base.

FIG. 8E is a cross-sectional view taken along line F8E-F8E in FIG. 8F.

FIG. 8F is a bottom view of the distal structure portion, as viewed in a direction of an arrow 8F in FIG. 8A.

FIG. 11 is a side view illustrating a state in which the pivot base is in a fallen position in the distal structure portion illustrated in FIG. 2.

FIG. 12 is a side view illustrating a state in which the pivot base is in a raised position in the distal structure portion illustrated in FIG. 11.

FIG. 14 is a side view illustrating a state in which the rotational shaft is displaced from the bearing when the pivot base is in the raised position in the distal structure portion illustrated in FIG. 7.

FIG. 19 is a cross-sectional view taken by a plane along the longitudinal direction L, FIG. 19 illustrating a state in which the cover removing tool is attached to the cover and distal structure portion illustrated in FIG. 16.

FIG. 24 is a cross-sectional view illustrating a distal structure portion, cover, restriction portion, etc. of an endoscope system of a second embodiment.

FIG. 27 is a side view illustrating a state in which the rotational shaft is displaced when the pivot base is in the fallen position in a state in which the cover is removed in the endoscope system illustrated in FIG. 24.

FIG. 28 is a side view illustrating a state in which the rotational shaft is displaced when the pivot base is in the raised position in the state in which the cover is removed in the endoscope system illustrated in FIG. 24.

FIG. 44 is a side view illustrating a step of attaching the cover to the distal structure portion in the endoscope system illustrated in FIG. 40.

FIG. 45 is a side view illustrating a distal structure portion, cover and guide portion of an endoscope system of a ninth embodiment, FIG. 45 illustrating a state in which the pivot base is in the fallen position.

FIG. 46 is a side view illustrating a state in which the pivot base is in the raised portion in the endoscope system illustrated in FIG. 45.

FIG. 47 is a side view illustrating a state in which the pivot base was pushed in the direction of the arrow C and the rotational shaft was displaced from the bearing, in a state in which the cover is removed in the endoscope system illustrated in FIG. 45.

FIG. 48 is a side view illustrating a state in which the pivot base was pushed in the direction of the arrow D and the rotational shaft was displaced from the bearing, in a state in which the cover is removed in the endoscope system illustrated in FIG. 46.

FIG. 52 is a side view illustrating a state in which the pivot base was pushed in the direction of the arrow C and the rotational shaft was displaced from the bearing, in a state in which the cover is removed in the endoscope system illustrated in FIG. 50.

FIG. 53 is a side view illustrating a state in which the pivot base was pushed in the direction of the arrow D and the rotational shaft was displaced from the bearing, in a state in which the cover is removed in the endoscope system illustrated in FIG. 51.

FIG. 56 is a partly cut-out cross-sectional illustrating a distal structure portion, cover and wire of an endoscope system of an eleventh embodiment, FIG. 56 being taken by a plane along the wire.

FIG. 57 is a side view illustrating, in enlarged scale, a pivot mechanism (pivot base) of the endoscope system illustrated in FIG. 56.

FIG. 58 is a side view illustrating the distal structure portion, cover and guide portion of the endoscope system illustrated in FIG. 56, FIG. 58 illustrating a state in which the pivot base is in the fallen position.

FIG. 59 is a side view illustrating a state in which the pivot base is in the raised portion in the endoscope system illustrated in FIG. 58.

DETAILED DESCRIPTION

Figure 3:
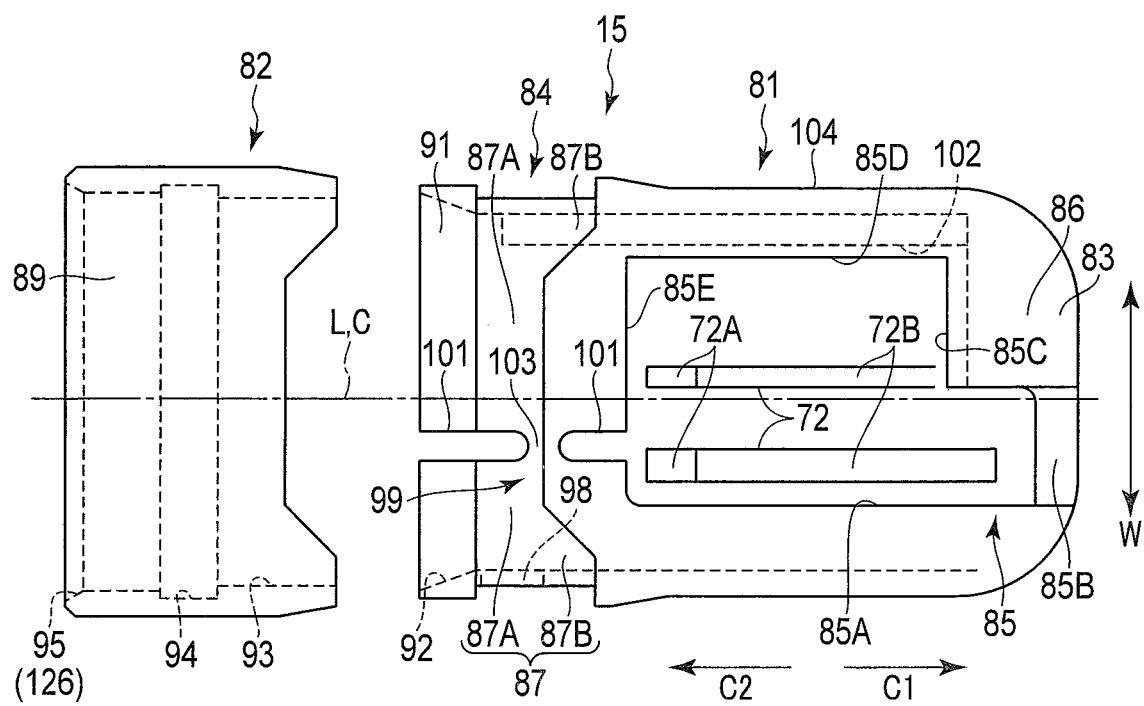
FIG. 3 is an exploded plan view illustrating a cover body and a ferrule of the cover illustrated in FIG. 2.

Hereinafter, embodiments for implementing the present invention will be described with reference to the accompanying drawings.

An endoscope system of a first embodiment will be described with reference to FIG. 1 to FIG. 23. As illustrated in FIG. 1 and FIG. 16, an endoscope system 11 includes an endoscope 12; an endoscope controller 13 (image processing unit) which performs image processing, based on a subject image captured by the endoscope 12; a monitor 14 which displays video that is generated by the image processing in the endoscope controller 13; and a cover removing tool 16 (exterior member removing tool) for removing a cover 15 at a distal end of the endoscope 12.

As illustrated in FIG. 1 and FIG. 2, the endoscope 12 (insertion device) includes an insertion section 21 which is inserted into a tract such as a lumen cavity of a subject along a longitudinal direction L; the cover 15 (exterior member, jacket) which is attached to a distal end of the insertion section 21; an operation section 22 which is provided at a proximal end of the insertion section 21 and is grasped by a user; a universal cord 23 extending from the operation section 22; and a rigid distal structure portion 24 provided at the distal end of the insertion section 21. Although details will be described later, the cover 15 is formed as a disposable type. The cover 15 is easily attachable to the distal structure portion 24 of the insertion section while the shape thereof is being maintained. However, the cover 15 is formed not to be easily detachable from the distal structure portion 24, for example, by an engaging pin 76 (to be described later) or the like.

As illustrated in FIG. 1, the insertion section 21 defines the longitudinal axis L by a distal end 21A and a proximal end 21B thereof. As illustrated in FIG. 1 and FIG. 2, the insertion section 21 includes a pivot base 25, the distal structure portion 24, a bending portion 26 and a tube portion 27 in the named order from the distal end 21A toward the proximal end 21B thereof. The tube portion 27 may be a flexible one which is a so-called flexible endoscope, or may be a so-called rigid endoscope which keeps a straight state and has resistance to bending. The bending portion 26 can be bent in a plurality of directions, for example, in two directions or four directions, by a knob 28 of the operation section 22 by a publicly known mechanism. Incidentally, in the embodiments to be described below, the description will be given by defining a distal direction side of the longitudinal direction L as C1, and by defining a proximal direction side opposite to the distal direction of the longitudinal direction L as C2. The distal structure portion 24 is provided at the distal end of the insertion section 21.

As illustrated in FIG. 1, FIG. 2 and FIG. 19, the endoscope 12 includes an illumination optical system 31, an observation optical system 32 and a treatment instrument insertion channel 36. Besides, although not illustrated, the endoscope 12 includes an air/water supply mechanism and a suction mechanism. The air/water supply mechanism includes a nozzle 34 (to be described) at a distal end thereof, and is operated by a first button 35 of the operation section 22. The suction mechanism communicates with the channel 36, and is operated by a second button 37 of the operation section 22.

The illumination optical system 31 and observation optical system 32 are inserted through the distal structure portion 24, bending portion 26 and tube portion 27 of the insertion section 21 of the endoscope 12, the operation section 22, and the universal cord 23. As illustrated in FIG. 2, the illumination optical system 31 includes an illumination window 38 in the distal structure portion 24. The observation optical system 32 includes an observation window 41 in the distal structure portion 24.

The channel 36 has a distal end opened in the distal structure portion 24 of the insertion section 21 of the endoscope 12 (see FIG. 19). The channel 36 has a proximal end opened near a proximal portion of the tube portion 27 of the insertion section 21, or opened in the operation section 22. Here, as illustrated in FIG. 1, an opening (not shown) of the proximal end of the channel 36 is provided in the operation section 22, and a forceps tap 42 is detachably attached to this opening via a mouthpiece. As illustrated in FIG. 19, a distal end of a tube 44 of the channel 36 is fixed to the distal structure portion 24 via a mouthpiece 43. Note that, as illustrated in FIG. 1, the tube 44 of the channel 36 is branched into a publicly known suction conduit 45, for example, in the inside of the operation section 22. The suction conduit 45 is coupled to the second button 37. By a pressing operation of the second button 37, sucked matter is discharged from an opening portion 46 (to be described later) at the distal end of the channel 36 via the mouthpiece 43, tube 44, suction conduit 45 and universal cord 23.

In this embodiment, the distal structure portion 24 is formed as such a side-viewing type that the direction of observation is different from a direction along the longitudinal direction L of the insertion section 21. The endoscope 12 includes a pivot mechanism 47 which properly adjusts the direction of a treatment instrument (not shown) or the like, which is passed through the channel 36, by the distal structure portion 24, thereby enabling observation within the view field.

The pivot mechanism 47 has a distal end near the distal structure portion 24 of the insertion section 21 of the endoscope 12, and has a proximal end in the operation section 22. As illustrated in FIG. 1, FIG. 8, etc., the pivot mechanism 47 includes, in the named order from the distal end toward the proximal end of the insertion section 21, a pivot base 25 (treatment instrument raising base; raising base) which is an example of a rotational portion; an elongated (linearly extending) wire 48 (pulling member); an elastic member 52 covering a part where the wire 48 is exposed in a wire moving section 51 (to be described later); and a lever 53. The pivot base 25 is formed in a substantially triangular shape or a boomerang shape. The pivot base 25 is supported on the distal structure portion 24 via a rotational shaft 54, and can pivotally move (raise) the treatment instrument at the distal end of the insertion section 21. A distal end of the wire 48 is supported by the pivot base 25, and a proximal end of the wire 48 is supported by the lever 53. As illustrated in FIG. 5, the wire 48 (pulling member) is connected to the pivot base 25 in the wire moving section 51 provided in the distal structure portion 24, and can remotely operate the pivot base 25. As illustrated in FIG. 5, an operating shaft portion 55, which is formed in an "L" shape, is provided at the distal end of the wire 48. The operating shaft portion 55 is fitted in a receiving portion 56 such that the operating shaft portion 55 is rotatable relative to the receiving portion 56 of the pivot base 25 and does not drop from the receiving portion 56.

Figure 6:
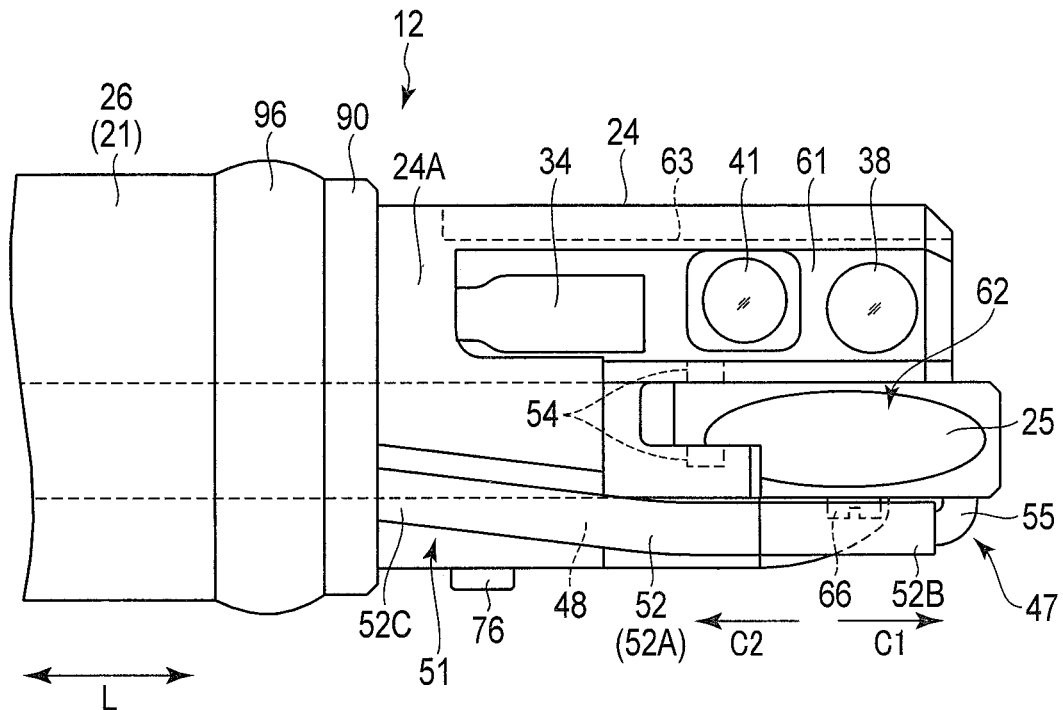
FIG. 6 is a plan view illustrating the distal structure portion illustrated in FIG. 2 in a state in which the cover is removed.

As illustrated in FIG. 5, the elastic member 52 is formed of a material, such as rubber, in a cylindrical shape (tubular shape). An exposed part of the wire 48 can be passed through the inside of the elastic member 52. The elastic member 52 includes an elastic member body 52A; one end 52B which is water-tightly fixed to the pivot base side on the distal direction C1 side of the longitudinal direction L; and the other end 52C which is water-tightly fixed to the distal structure portion 24 on the proximal direction C2 side of the longitudinal direction L. The elastic member 52 prevents liquid or gas from entering the inside of the insertion section 21 along the wire 48, to be more specific, the inside of the tube portion 27 of the insertion section 21. Both ends of the elastic member 52 are water-tightly connected to the pivot base 25 and the distal structure portion 24. As illustrated in FIG. 6, the one end 52B of the elastic member 52 is fixed, via an adhesive or the like, to that end portion of the operating shaft portion 55, which projects from the pivot base 25.

As illustrated in FIG. 6, etc., the distal structure portion 24 includes a block-shaped main body 24A. As illustrated in FIG. 2, FIG. 3, and FIG. 5 to FIG. 7, in the main body 24A, a planar portion 61 (to be described later), a storage portion 62 (storage space), the wire moving section 51 (wire moving space), a guide groove 63 and a pin fixing portion 64 are formed from a cylinder of rigid material such as stainless steel. In the main body 24A, a center axis C is defined. In the description below, it is assumed that the above-described longitudinal direction L agrees with the center axis C.

Figure 7:
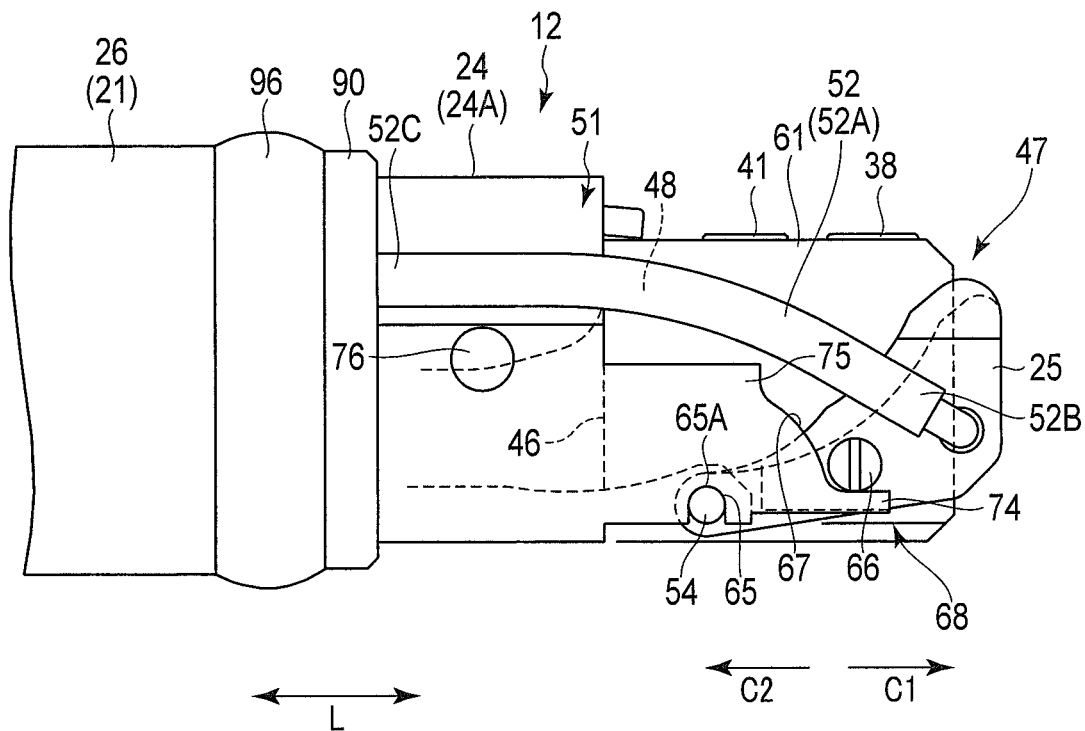
FIG. 7 is a side view illustrating the distal structure portion illustrated in FIG. 2 in a state in which the cover is removed.

As illustrated in FIG. 6 and FIG. 7, the main body 24A is provided with the illumination window 38 at the distal end of the illumination optical system 31; the observation window 41 at the distal end of the observation optical system 32; and a distal portion of the tube 44 of the channel 36. Thus, the distal structure portion 24 is formed of the main body 24A, the illumination window 38 of the illumination optical system 31, the observation window 41 of the observation optical system 32, and the distal portion of the tube 44 of the channel 36. The pivot base 25 at the distal end portion of the pivot mechanism 47 is rotatably attached to the main body 24A.

As illustrated in FIG. 6, FIG. 7 and FIG. 19, the main body 24A includes the planar portion 61 in which the illumination window 38 and observation window 41 are fixed; the storage portion 62 which pivotably stores the pivot base 25; the opening portion 46 which communicates with the storage portion 62 and with the channel 36, and guides the treatment instrument to the pivot base 25; a bearing 65 which rotatably holds the rotational shaft 54 of the pivot base 25; a guide portion 67 which guides a preventing portion 66 (to be described later) of the pivot base 25; and a restriction portion 68 which is provided to neighbor the guide portion 67 and restricts the range of rotation of the pivot base 25. As illustrated in FIG. 19, the distal end of the tube 44 of the channel 36 is fixed in the opening portion 46. It is preferable that the distal side of the storage portion 62 along the longitudinal direction L, that is, the distal end of the main body 24A, is open. In the meantime, as illustrated in FIG. 6, the wire moving section 51, which is continuous with the storage portion 62 and moves the wire 48, is formed on the proximal side of the storage portion 62.

It is assumed that the planar portion 61 of the main body 24A is parallel to the longitudinal direction L. As illustrated in FIG. 6 and FIG. 7, on the planar portion 61 of the main body 24A, the illumination window 38 is arranged on the distal side, and the observation window 41 is arranged adjacent to the illumination widow 38 on the proximal side. Note that the nozzle 34 is provided on the proximal side of the observation window 41. The nozzle 34 is directed toward the observation window 41 and illumination widow 38. The nozzle 34 can discharge a liquid, such as physiological saline, toward the observation window 41 and illumination widow 38, and can blow away, by air, a deposit on the observation window 41 and illumination widow 38.

Figure 8A:
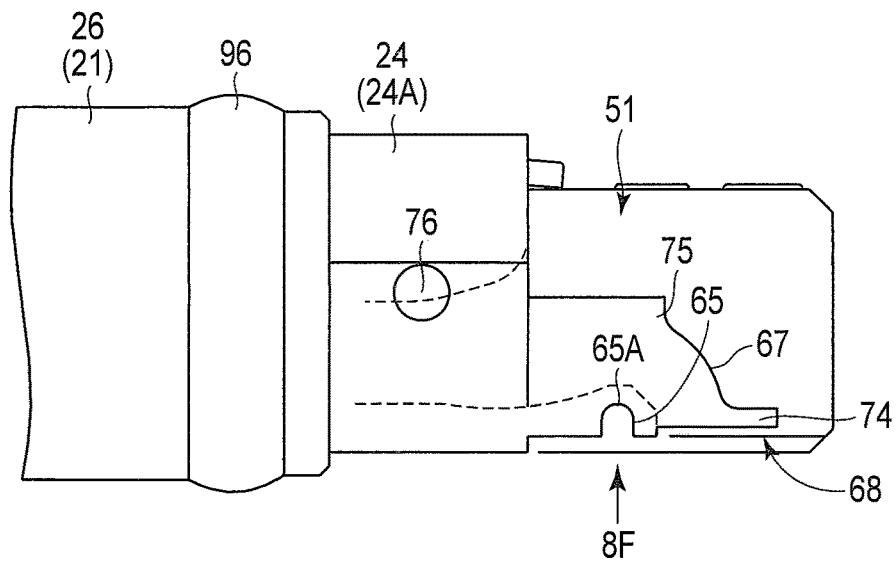
FIG. 8A is a side view illustrating the distal structure portion illustrated in FIG. 7 in a state in which a pivot base is removed from the distal structure portion.
Figure 8B:
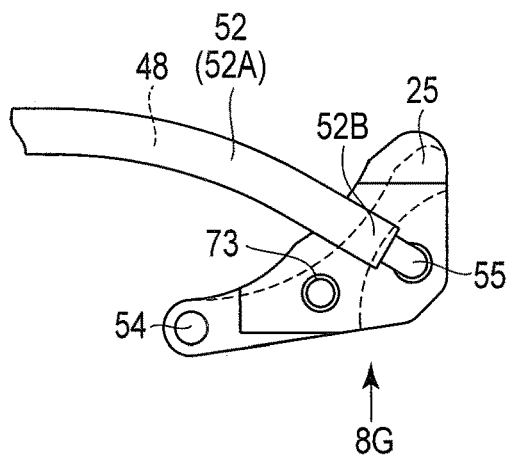
FIG. 8B is a side view illustrating the pivot base and wire of a pivot mechanism.
Figure 9:
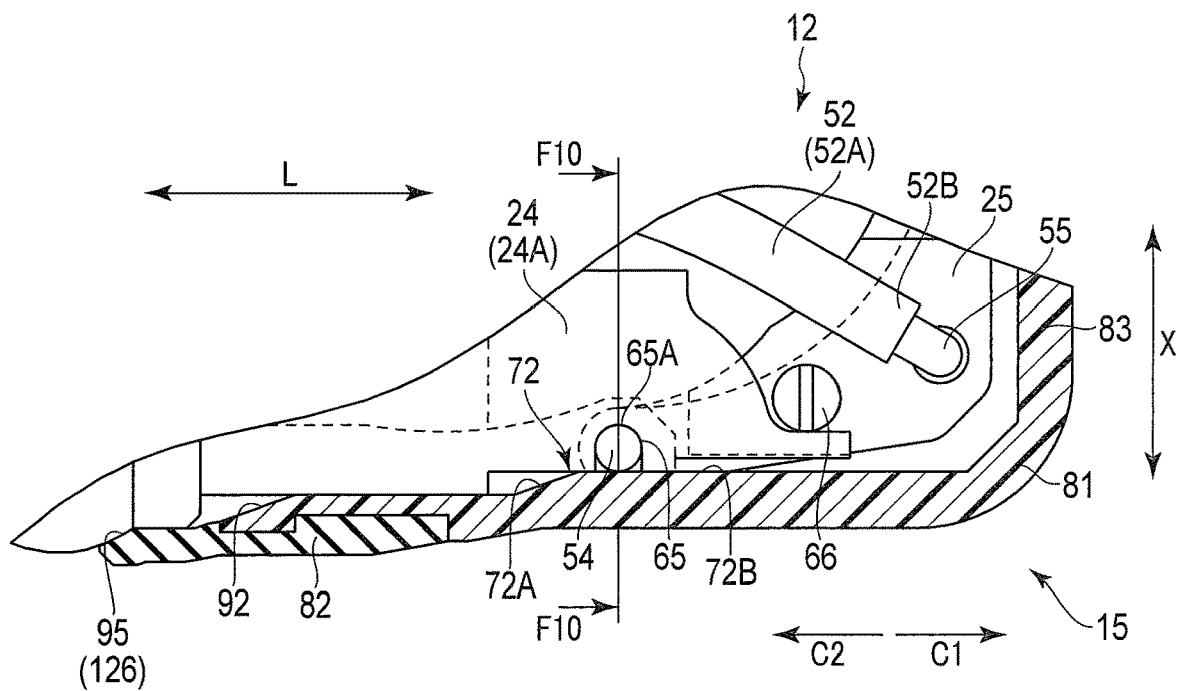
FIG. 9 is a cross-sectional view illustrating the distal structure portion and cover illustrated in FIG. 2, FIG. 9 being taken by a plane along a longitudinal direction L at a position of a rotational shaft of the pivot base.
Figure 10:
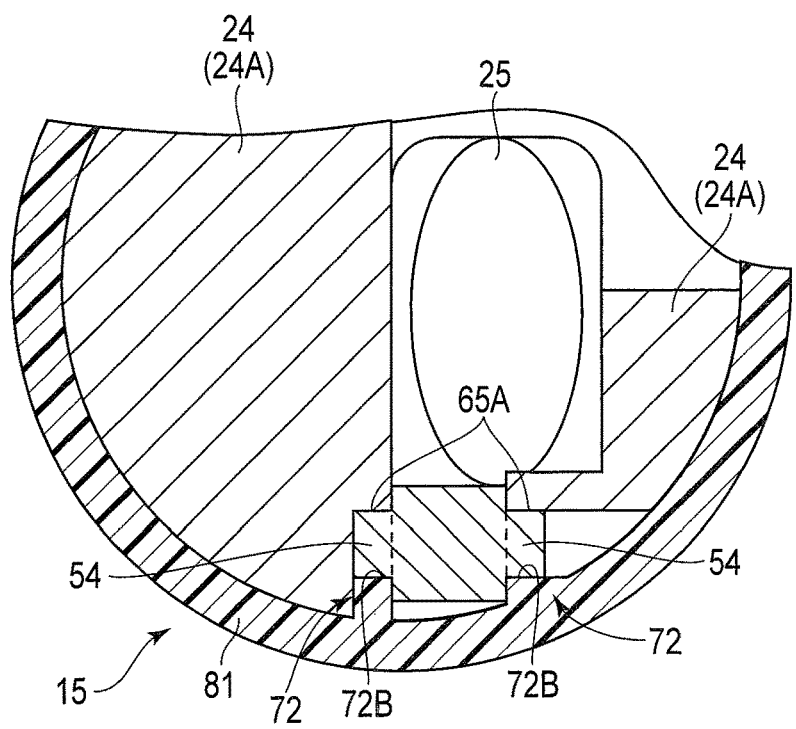
FIG. 10 is a cross-sectional view which is cut at a position of line F10-F10 in FIG. 9.

As illustrated in FIG. 8A and FIG. 9, the bearing 65 is provided to be recessed from a peripheral part (outer surface) of the distal structure portion 24, such that the bearing 65 receives the rotational shaft 54 of the pivot base 25 (to be described later). The bearing 65 has a substantially "U" shape, and can support the rotational shaft 54 in the inside thereof. In other words, it can be said that the bearing 65 has a groove shape. The dimension of the bearing 65 in the longitudinal direction (L direction) is equal to or slightly greater than the dimension of the rotational shaft 54 in the longitudinal direction (L direction). As will be described later with reference to FIG. 13 and FIG. 14, in the state in which the cover 15 is removed from the distal structure portion 24, the rotational shaft 54 can be displaced relative to the bearing 65 (can be lifted relative to a bottom 65A of the bearing 65) when the pivot base 25 is in a fallen position P1 or a raised position P2.

As illustrated in FIG. 6 to FIG. 8, the storage portion 62 is arranged in a direction perpendicular to the longitudinal direction L, relative to the planar portion 61. The storage portion 62 forms a space in which the pivot base 25 can rotate within a predetermined range. The pivot base 25 is pivotable relative to the bearing 65 of the main body 24A, with the rotational shaft 54 functioning as the fulcrum. The pivot base 25 is an example of a rotational portion which rotates about the rotational shaft 54, and is a treatment instrument raising base which raises (erects) the treatment instrument, which is inserted in the subject along the insertion section 21, relative to the insertion section 21.

Figure 8C:
FIG. 8C is a plan view of a preventing portion (screw) which is fastened in a screw hole of the pivot base.
Figure 8G:
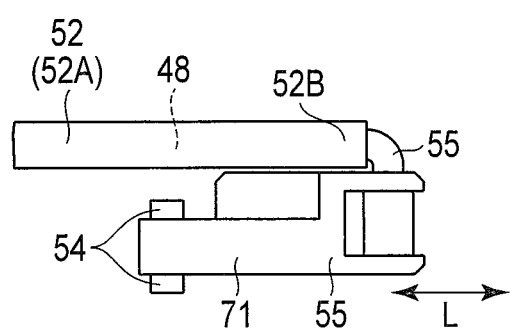
FIG. 8G is a bottom view of the pivot base, as viewed in a direction of an arrow 8G in FIG. 8B.
Figure 13:
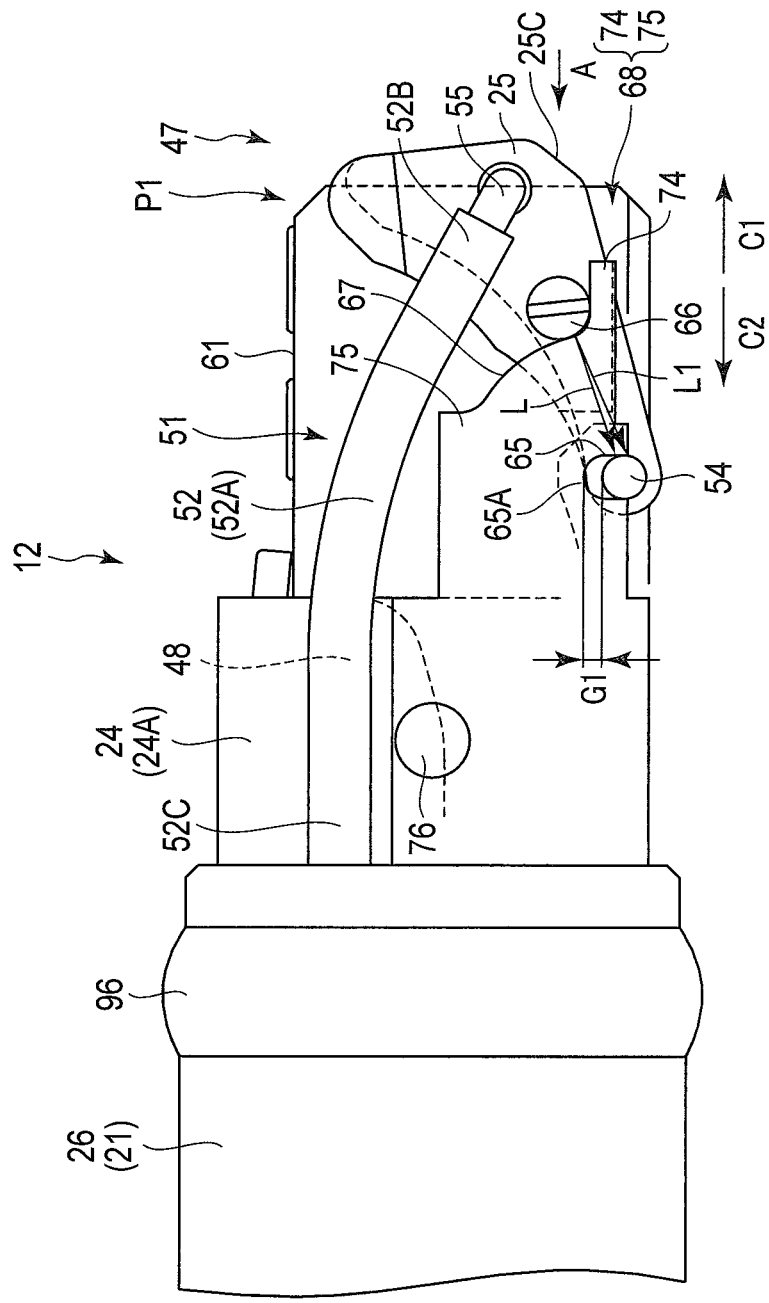
FIG. 13 is a side view illustrating a state in which the rotational shaft is displaced from a bearing when the pivot base is in the fallen position in the distal structure portion illustrated in FIG. 7.

As illustrated in FIG. 8G, FIG. 8C and FIG. 8D, the pivot base 25 includes a pivot base body 71, the rotational shaft 54 which is formed integral with the pivot base body 71, and a preventing portion 66 which prevents the rotational shaft 54 from dropping from the bearing 65 of the main body 24A. The rotational shaft 54 is held to be rotatable relative to the bearing 65 of the distal structure portion 24. The rotational shaft 54 is provided to project on both sides in a direction crossing the longitudinal direction (L direction) from the pivot base body 71 of the pivot base 25. Thus, the rotational shaft 54 of the pivot base 25 is rotatably supported in a so-called both-end support fashion, such that the rotational shaft 54 is clamped between the bearing 65 of the distal structure portion 24 and an alignment portion 72 (to be described later) of the cover 15 (see FIG. 9 and FIG. 10). In the present embodiment, the preventing portion 66 is provided on the pivot base 25 (rotational portion) side. In this embodiment, as illustrated in FIG. 13, a shortest distance L between the preventing portion 66 and rotational shaft 54 and a distance L1 between the preventing portion 66 and a corner portion of the bearing 65 have a relationship of L<L1. Thus, the pivot base 25 does not drop from the distal structure portion 24. In addition, in FIG. 14, the shortest distance L and a distance L2 between the preventing portion 66 and the corner portion of the bearing 65 have a relationship of L<L2. Thus, the pivot base 25 does not drop from the distal structure portion 24.

As illustrated in FIG. 7, FIG. 8B, FIG. 8C and FIG. 8D, the preventing portion 66 is composed of a screw (a head portion of a screw) which is fixed in a screw hole 73 formed in the pivot base body 71 of the pivot base 25. The preventing portion 66 cooperates with the guide portion 67 and wire 48, thereby defining a distance of lifting of the rotational shaft 54 from the bottom 65A of the bearing 65. Specifically, the structure of the preventing portion 66, guide portion 67 and wire 48 prevents the rotational shaft 54 from dropping from the bearing 65, and prevents the pivot base 25 from dropping from the distal structure portion 24. In addition, in an attitude in which the cover 15 (exterior member) is attached and detached, i.e. in a position in which the pivot member 25 (rotational portion) is not raised relative to the distal structure portion 24, the preventing portion 66 exactly restricts the disengagement of the pivot base 25. Note that the "position in which the pivot member 25 (rotational portion) is not raised relative to the distal structure portion 24" corresponds to positions other than the raised position P2, and, to be more specific, corresponds to both the fallen position P1 and a position between the fallen position P1 and raised position P2.

A distal end of the wire 48 of the pivot mechanism 47 is supported by the pivot base 25. In the meantime, the proximal end (not shown) of the wire 48 of the pivot mechanism 47 is supported by the lever 53 of the operation section 22. Since the length of the wire 48 is adjusted, the pivot base 25 is disposed in a position (fallen position P1) indicated by a solid line in FIG. 11 when the lever 53 is in a first position S1 (the most raised state illustrated in FIG. 1). As the lever 53 is gradually pushed down, the wire 48 is pulled, and a distal end portion 25B of the pivot base 25, which is remote from the rotational shaft 54, is gradually raised with the rotational shaft 54 functioning as the fulcrum. It is assumed that the state in which the lever 53 is most pushed down is a second position. At this time, as indicated by a solid line in FIG. 12, the pivot base 25 is disposed in a most raised position P2.

As illustrated in FIG. 7 and FIG. 8A, the guide portion 67 of the distal structure portion 24 is formed in an arcuate shape having a center at the bearing 65, in such a manner to guide the preventing portion 66 of the pivot base 25. The guide portion 67 can guide the preventing portion 66 when the pivot base 25 is rotated relative to the distal structure portion 24. The restriction portion 68 is provided to neighbor the guide portion 67 and to be continuous with the guide portion 67. The restriction portion 68 includes a first stopper 74 which restricts the rotational angle of the pivot base 25 on the fallen position P1 side of the pivot base 25, and a second stopper 75 which restricts the rotational angle of the pivot base 25 on the raised position P2 side of the pivot base 25. The first stopper 74 and second stopper 75 abut on the preventing portion 66, thereby restricting the rotational angle of the pivot base 25.

As illustrated in FIG. 6, the main body 24A of the distal structure portion 24 includes, on an outer peripheral surface thereof, a guide groove 63 as a first guide along the longitudinal direction L. The guide groove 63 neighbors the planar portion 61, but is disposed at a position remote from the storage portion 62, i.e. the wire 48 and pivot base 25 of the pivot mechanism 47. It is preferable that the guide groove 63 is continuously formed from the distal end to proximal end of the main body 24A.

As illustrated in FIG. 5, the pin fixing portion 64 is formed on the outer peripheral surface of the main body 24A of the distal structure portion 24. It is preferable that the pin fixing portion 64 neighbors the wire moving section 51 and is formed substantially on the opposite side to the guide groove 63, with the center axis C of the main body 24A of the distal structure portion 24 being interposed. The engaging pin 76 (engaging portion), which projects in a direction perpendicular to the center axis C, is fixed on the pin fixing portion 64. The engaging pin 76 is formed in a columnar shape, but the shape of the engaging pin 76 is not limited to the columnar shape. An inclined surface may be provided on the side of the wire moving section 51 on the upper side of the engaging pin 76, so that the engaging pin 76 may easily be disengaged from an engaging recess portion 98. In addition, an inclined surface may be provided on the distal side, so that the engaging pin 76 may easily be engaged in the engaging recess portion 98.

Figure 4:
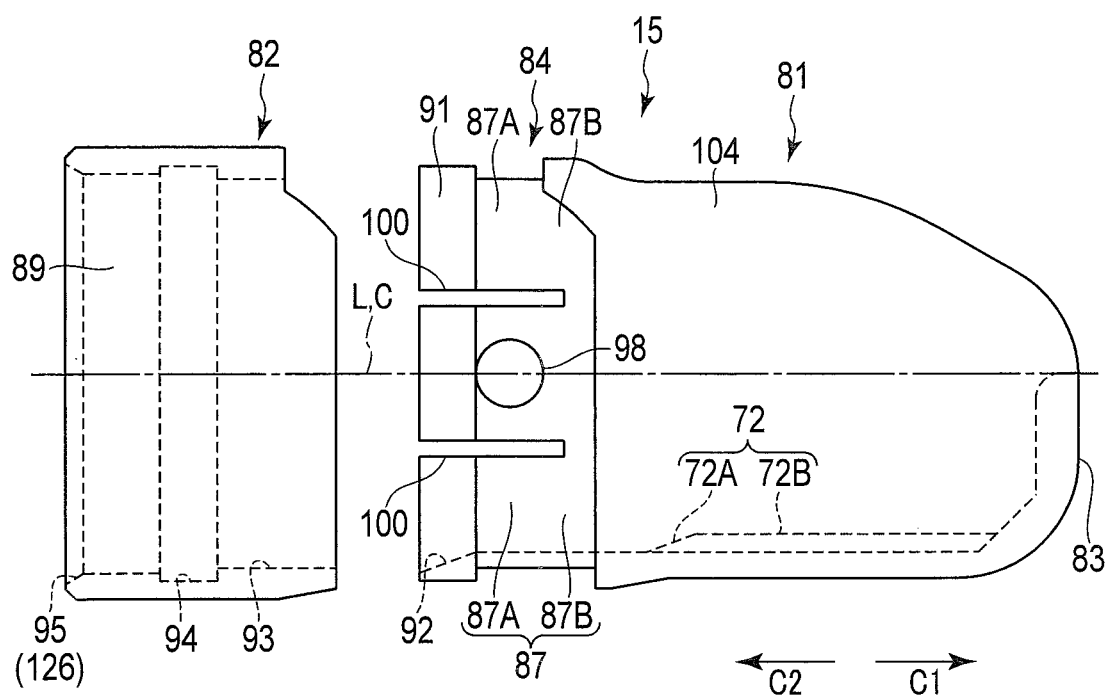
FIG. 4 is an exploded side view illustrating the cover body and ferrule of the cover illustrated in FIG. 3.

As illustrated in FIG. 3 and FIG. 4, the cover 15 (exterior member) includes a cover body 81 and a ferrule 82. The cover body 81 is formed of, for example, a resin material, in an integral cylindrical shape. The cover 15 is an example of an exterior member which is detachably attached to the distal structure portion 24. Specifically, the cover 15 (exterior member) is a jacket which covers the distal structure portion 24 when the cover 15 (exterior member) is attached to the distal structure portion 24.

The ferrule 82 is formed of, for example, a member (rubber material) having rubber-like elasticity, in a cylindrical or annular shape. Incidentally, it is preferable that the cover body 81 and ferrule 82 are formed of a material with electrical insulating properties. In addition, the inside diameters, or the inner peripheral surfaces, of the cover body 81 and ferrule 82 are formed to have proper sizes and shapes, based on the size of the distal structure portion 24.

The cover body 81 includes a closing portion 83 at its distal end, and includes an annular portion 84 at its proximal end. The closing portion 83 is formed in a substantially hemispheric shape. The proximal end of the cover body 81, that is, the annular portion 84, is opened. The cover body 81 includes a substantially rectangular opening edge portion 85 (opening portion) between the closing portion 83 and annular portion 84. The opening edge portion 85 exposes the illumination window 38, observation window 41, nozzle 34 and pivot base 25 of the distal structure portion 24 to the outside.

As illustrated in FIG. 3 and FIG. 4, the opening edge portion 85 (opening portion) includes a right-side edge portion 85A which is provided on the right side along the longitudinal direction L from the proximal direction C2 side toward the distal direction C1 side; a U-shaped recess portion 85B which is continuous with the right-side edge portion 85A; a distal edge portion 85C which is continuous with the recess portion 85B; a left-side edge portion 85D which is continuous with the recess portion 85B and is provided on the left side along the longitudinal direction L from the proximal direction C2 side toward the distal direction C1 side; and a proximal edge portion 85E which is provided between the right-side edge portion 85A and left-side edge portion 85D. The opening edge portion 85 forms a closed loop by the right-side edge portion 85A, recess portion 85B, distal edge portion 85C, left-side edge portion 85D and proximal edge portion 85E. It is preferable that the right-side edge portion 85A and left-side edge portion 85D are parallel or substantially parallel to each other. It is preferable that the distal edge portion 85C and proximal edge portion 85E are parallel or substantially parallel to each other. Not only at a time when the pivot base 25 pivotally moves the treatment instrument, but also at all other times, the endoscope 12 exposes the pivot base 25 from the opening edge portion 85 (opening portion) (see FIG. 15).

As illustrated in FIG. 3 and FIG. 4, the right-side edge portion 85A, together with the annular portion 84 and a rotational circumferential surface 104 (to be described later), covers the wire 48 and elastic member 52 of the pivot mechanism 47 such that the wire 48 and elastic member 52 are movable. The distal edge portion 85C includes a distal covering portion 86 which covers the distal direction C1 side of the planar portion 61 of the main body 24A, with respect to the illumination window 38.

Figure 15:
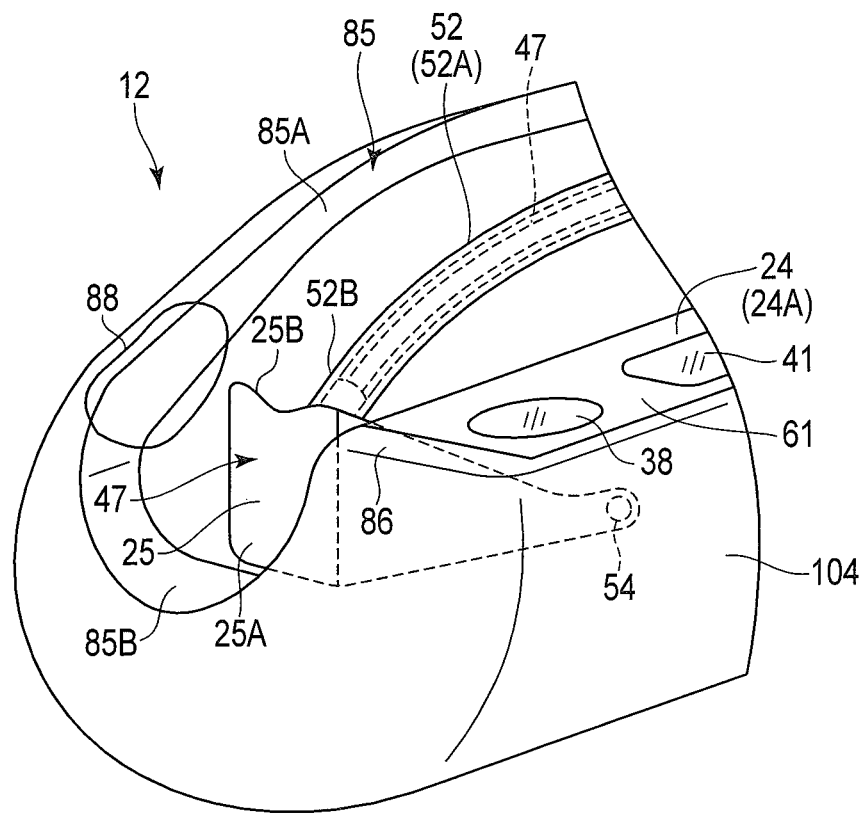
FIG. 15 is a perspective view illustrating, in enlarged scale, parts on a distal direction side of the distal structure portion and cover illustrated in FIG. 2.
Figure 16:
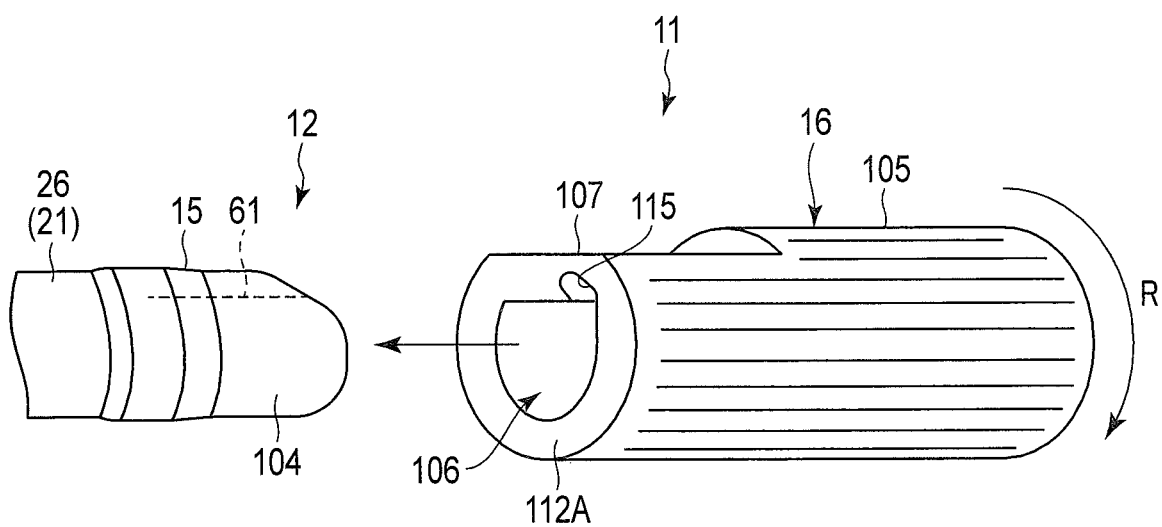
FIG. 16 is a perspective view illustrating a step of attaching a cover removing tool to the cover (endoscope) illustrated in FIG. 2, and then rotating the cover removing tool in an R direction.

As illustrated in FIG. 3 and FIG. 15, the U-shaped recess portion 85B, which is continuous with the right-side edge portion 85A, is formed at a distal end of the right-side edge portion 85A. The recess portion 85B is formed toward the closing portion 83.

As illustrated in FIG. 4, the annular portion 84 includes, on its outer peripheral surface, an engaging portion 87 with which the ferrule 82 is engaged. The engaging portion 87 is formed at a position spaced apart toward the proximal direction C2 side along the longitudinal direction L from the proximal edge portion 85E of the opening edge portion 85. The engaging portion 87 includes an annular recess portion 87A which suppresses a movement of the ferrule 82 along the longitudinal direction L relative to the cover body 81; and an engaging recess portion 87B which suppresses a movement of the ferrule 82 around the axis in the longitudinal direction L. The annular recess portion 87A and engaging recess portion 87B are integrally continuously formed. In the annular portion 84, an annular flange portion 91 is formed at a proximal end of the engaging portion 87, the annular flange portion 91 projecting radially outward with respect to the longitudinal direction L, relative to the annular recess portion 87A. A skirt portion 92, which has a gradually decreasing thickness toward the proximal direction C2 side along the longitudinal direction L, is formed on the inner periphery of the flange portion 91. The skirt portion 92 has a gradually increasing inside diameter toward the proximal direction C2 side.

Note that it is preferable that the inside diameter of the inner peripheral surface of the cover body 81 is constant from the vicinity of the distal end of the right-side edge portion 85A of the opening edge portion 85, and from the vicinity of the distal end of the left-side edge portion 85D, to the distal end of the skirt portion 92 of the flange portion 91.

As illustrated in FIG. 3 and FIG. 4, the ferrule 82 includes, on its inner peripheral surface, an annular projection portion 93 which is engaged in the annular recess portion 87A. The ferrule 82 includes, on its inner peripheral surface, an annular engaging recess portion 94 in which the flange portion 91 is engaged. Thus, as illustrated in FIG. 2, the ferrule 82 is engaged with the annular portion 84 of the cover body 81. As illustrated in FIG. 4 and FIG. 5, the ferrule 82 includes a second skirt portion 95 on its inner peripheral surface. A bobbin portion 96 (fixing portion), which is coated with resin, is engaged with, and is put in water-tight contact with, the second skirt portion 95. The bobbin portion 96 is provided at the distal portion of the bending portion 26, and fixes a jacket 97 of the bending portion 26 to the distal structure portion 24. The second skirt portion 95 has a gradually decreasing thickness toward the proximal side along the longitudinal direction L, and has a gradually increasing inside diameter toward the proximal direction C2 side.

As illustrated in FIG. 4 and FIG. 5, an engaging recess portion 98 (engaging portion), which is engageable with the engaging pin 76, is formed in an inner peripheral surface of the annular portion 84 of the cover body 81. The engaging recess portion 98 may be formed in such a state that the inner peripheral surface and outer peripheral surface of the cover body 81 communicate with each other, or may be simply formed in a recess shape in the inner peripheral surface of the cover body 81. It is preferable that the engaging recess portion 98 is formed in the annular recess portion 87A. A pair of notches 100, which extend in the longitudinal direction (L direction), are formed near the engaging recess portion 98. The engaging recess portion 98 is provided at a position between the two notches 100. Each notch 100 is provided to extend over the flange portion 91, annular recess portion 87A and engaging recess portion 87B of the annular portion 84. In the present embodiment, the notches 100 contribute to elastic deformation of the flange portion 91 and annular recess portion 87A. As a result, elastic deformation tends to easily occur in the vicinity of the engaging recess portion 98, and, even with relatively weak force, the engagement between the engaging recess portion 98 and engaging pin 76 can be released, and also the engaging recess portion 98 and engaging pin 76 can easily be engaged.

Figure 20:
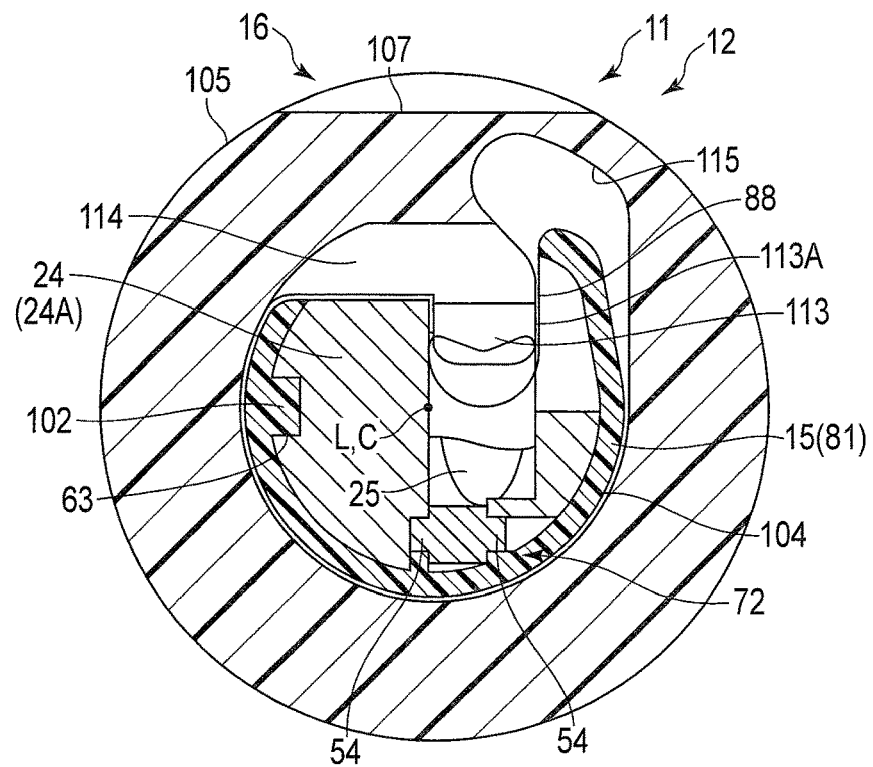
FIG. 20 is a cross-sectional view taken along line F20-F20 in FIG. 19.
Figure 21:
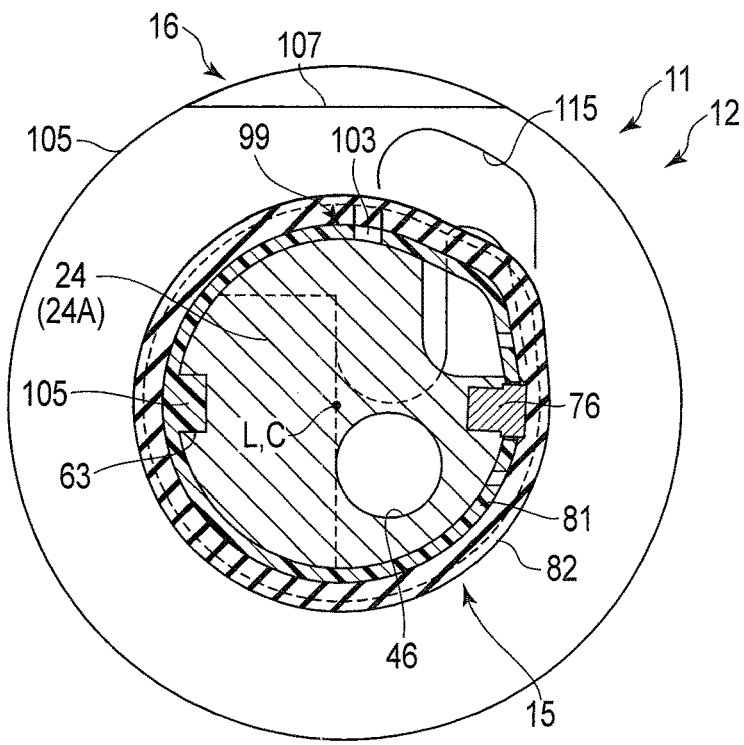
FIG. 21 is a cross-sectional view taken along line F21-F21 in FIG. 19.

As illustrated in FIG. 3 and FIG. 4, a guide projection portion 102 and an alignment portion 72 are formed on the inner peripheral surface of the cover body 81. Specifically, the guide projection portion 102 is formed to be movable along the guide groove 63, and projects radially inward from the inner peripheral surface of the cover body 81. It is preferable that the guide projection portion 102 is formed from the vicinity of the distal end of the inner peripheral surface of the cover body 81 to the vicinity of the proximal end thereof. The guide projection portion 102 can be formed in a proper shape. For example, as illustrated in FIG. 20, the guide projection portion 102 is formed to have a substantially rectangular transverse cross section so as to correspond to the shape of the guide groove 63. Besides, although not illustrated, the guide projection portion 102 may be composed of a plurality of guide projection portions, and these guide projection portions may be mutually spaced apart at proper intervals.

As illustrated in FIG. 3, the alignment portion 72 is formed of a pair of alignment portions each having a projecting shape extending in the longitudinal direction (L direction). One of the alignment portions 72 has a greater width dimension with respect to a direction W crossing the longitudinal direction L than the other of the alignment portions 72. As illustrated in FIG. 9, when the cover 15 is attached to the distal structure portion 24, the alignment portion 72 aligns the rotational shaft 54 in the original position. To be more specific, when the cover 15 is attached to the distal structure portion 24 in a direction along the longitudinal direction L of the insertion section 21, the alignment portion 72 moves the rotational shaft 54 in a direction X crossing the longitudinal direction L, and aligns the rotational shaft 54 in a predetermined position (bottom 65A) in the bearing 65.

As illustrated in FIG. 3, FIG. 4, FIG. 9 and FIG. 10, each of the alignment portions 72 includes a smooth inclined surface 72A which gradually projects in an inward direction (direction toward the center axis C) toward the closing portion 83, and a track 72B extending from the inclined surface 72A in the longitudinal direction L. The inclined surface 72A guides the rotational shaft 54 to a predetermined position (bottom 65A) in the bearing 65, when the cover 15 is attached to the distal structure portion 24. The track 72B pushes the rotational shaft 54 onto the bearing 65, when the cover is attached to the distal structure portion 24. After the cover 15 was attached to the distal structure portion 24, the track 72B abuts on the rotational shaft 54 and holds the rotational shaft 54 in the predetermined position (bottom 65A) in the bearing 65.

As illustrated in FIG. 3, a fragile portion 99 is formed between the proximal edge portion 85E of the opening edge portion 85 of the cover body 81 and the proximal end of the flange portion 91 of the annular portion 84. The fragile portion 99 is decreased in strength and made fragile, compared to the other parts, and the fragile 99 is destroyed when the cover 15 is removed from the distal structure portion 24. Here, the fragile portion 99 includes a pair of slits 101, and a coupling portion 103 (broken portions 103) which is located between the slits 101. One slit 101 is formed continuous with the proximal edge portion 85E. The other slit 101 is formed continuous with the proximal end of the flange portion 91 of the annular portion 84. In this case, the slits 101 are formed along the longitudinal direction L. The slits 101 do not communicate with each other, and the coupling portion 103 is formed. Note that the engaging recess portion 98 is formed at a position rotated by about 90° from the coupling portion 103 around the center axis C. In addition, the guide projection portion 102 is formed at a position rotated by about 90° from the coupling portion 103 around the center axis C in a circumferential direction on the side opposite to the engaging recess portion 98. As illustrated in FIG. 2, it is preferable that the fragile portion 99 is disposed not over the planar portion 61 of the main body 24A of the distal structure portion 24, but over the wire moving section 51.

As illustrated in FIG. 3 and FIG. 4, the cover body 81 includes the rotational circumferential surface 104 on its outer periphery. The rotational circumferential surface 104 is formed as a part of the cylinder. The center axis C of the cover 15 and distal structure portion 24 is defined by the rotational circumferential surface 104. This rotational circumferential surface 104 is engaged in the inside of a cylindrical portion 112 (to be described later) of the cover removing tool 16.

When the cover 15 is formed, the ferrule 82 is attached to the cover body 81 illustrated in FIG. 3. At this time, to begin with, it is confirmed that the coupling portion 103 exists between the slits 101 of the cover body 81, and the slits 101 are not continuous. Thereafter, the ferrule 82 is engaged with the cover body 81, thereby forming the cover 15.

As illustrated in FIG. 2 to FIG. 4, the cover 15 is attached to the distal structure portion 24 by defining the direction of the cover 15 in the circumferential direction about the longitudinal direction L. At this time, the guide projection portion 102 of the cover 15 is engaged in the guide groove 63 of the main body 24A of the distal structure portion 24, and the guide projection portion 102 is moved along the longitudinal direction L. Thus, misalignment in the circumferential direction of the cover 15 in relation to the distal structure portion 24 is prevented.

In addition, when the cover 15 is attached to the distal structure portion 24, the second skirt portion 95 of the engaging portion 89 of the ferrule 82 of the cover 15 is abutted on the engaging pin 76 of the distal structure portion 24. At this time, the engaging portion 89 elastically deforms by its elasticity, and passes over the engaging pin 76. Furthermore, the skirt portion 92 of the annular portion 84 of the cover body 81 abuts on the engaging pin 76 of the distal structure portion 24. At this time, the annular portion 84 elastically deforms by the notches 100, and passes over the engaging pin 76. Thus, the engaging recess portion 98 is engaged with the engaging pin 76 of the distal structure portion 24. Incidentally, by increasing the inside diameter of the engaging portion 89, the engaging portion 89 may be made to pass over the engaging pin 76 without coming in contact with the engaging pin 76.

In addition, the second skirt portion 95 of the ferrule 82 or a part of the engaging portion 89 abuts on, and comes in water-tight contact with, the bobbin portion 96 at the distal end of the bending portion 26 and an insulating member 90 on the distal direction C1 side of the bobbin portion 96 (see FIG. 5). Note that the bobbin portion 96 is a part where an adhesive was applied from the outer periphery of the string which is annually wound, and the applied adhesive was fixed. The ferrule 82 is put in close contact with at least one of the bobbin portion 96 and insulating member 90 over the entire circumference. Thus, when a treatment is performed by using a high-frequency treatment instrument or the like, high-frequency current, which leaks from the high-frequency treatment instrument, does not leak to the outside of the ferrule 82 via the distal structure portion 24.

At this time, as illustrated in FIG. 2, the illumination window 38, observation window 41 and nozzle 34 are exposed to the opening edge portion 85 of the cover 15, and the pivot base 25 is exposed such that the pivot base 25 is pivotable within a proper range. As illustrated in FIG. 15, in the state in which the cover 15 is properly attached to the distal structure portion 24, a part of a distal surface 25A and the distal end portion 25B of the pivot base 25 are exposed, as viewed from the distal side along the longitudinal direction L. Thus, when the treatment instrument (not shown) is guided by the pivot base 25 and projected from the distal end of the pivot base 25, the recess portion 85B prevents the treatment instrument from interfering with the cover 15.

In the endoscope 12, in the state in which the cover 15 is attached to the distal structure portion 24, the insertion section 21 is inserted into a tract such as a lumen cavity, and observation and a proper treatment are performed. Note that the fragile portion 99 is covered and protected by the ferrule 82. Thus, for example, during the insertion into a tract such as a lumen cavity, or during a treatment, even if the fragile portion 99 abuts on an inner wall or the like, breakage of the fragile portion 99 is prevented.

After the use of the endoscope 12, the cover 15 and ferrule 82 are removed from the distal structure portion 24, and are discarded. Specifically, in the state in which the cover 15 is removed, the endoscope 12 (the distal structure portion 24 of the endoscope 12) is cleaned, disinfected and sterilized, and is reused. At this time, since the cover 15 is removed from the distal structure portion 24, the channel 36 and pivot mechanism 47, as well as the vicinity of the illumination window 38 of the illumination optical system 31 and the vicinity of the observation window 41 of the observation optical system 32, are easily cleaned.

In the meantime, when the cover 15 is removed from the distal structure portion 24, it is possible to remove the cover 15 by ripping the coupling portion 103 between the slits 101 by using the force of the user's fingers. However, when the cover 15 is removed from the distal structure portion 24 by the user's fingers, the manner of removal may differ from user to user. Thus, there is concern that it is difficult to stably destroy the fragile portion 99.

The fragile portion 99 can stably be destroyed by using the cover removing tool 16 (exterior member removing tool) which will be described below with reference to FIG. 16 to FIG. 19. It is thus preferable to use the cover removing tool 16 at a time of removing the cover 15 from the distal end portion 24 after the use of the endoscope 12.

The cover removing tool 16 according to the present embodiment is formed of a resin material having higher rigidity than the cover body 81 of the cover 15. Specifically, while the cover 15 is formed of a general resin material such as a plastic, a fiber reinforced plastic such as a glass fiber reinforced plastic can be used for the cover removing tool 16. On the other hand, the distal structure portion 24 is formed of a general metallic material (stainless steel, etc.). Specifically, the cover removing tool 16 is formed of a material which is harder than the cover 15 and is softer than the distal structure portion 24. Thereby, the fragile portion 99 of the cover 15 can easily be destroyed, and the distal structure portion 24 is prevented from being accidentally damaged.

Figure 17:
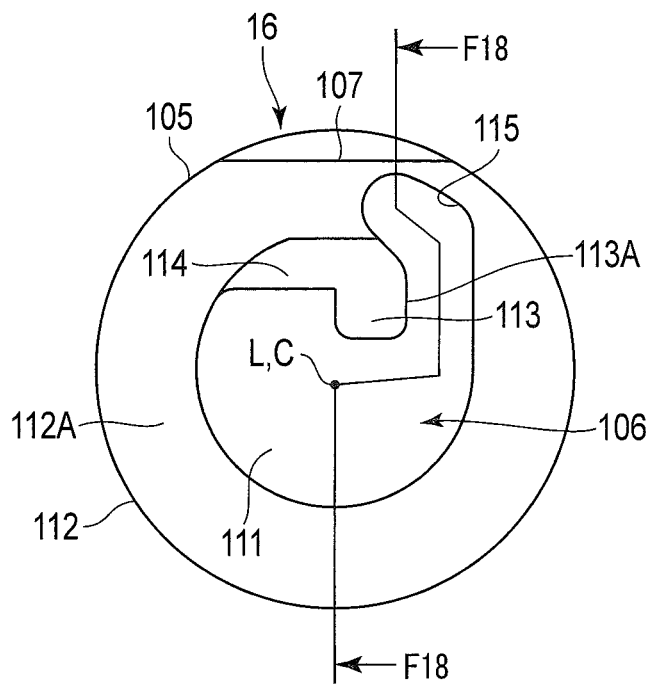
FIG. 17 is a front view illustrating, from a working portion side, the cover removing tool illustrated in FIG. 16.
Figure 18:
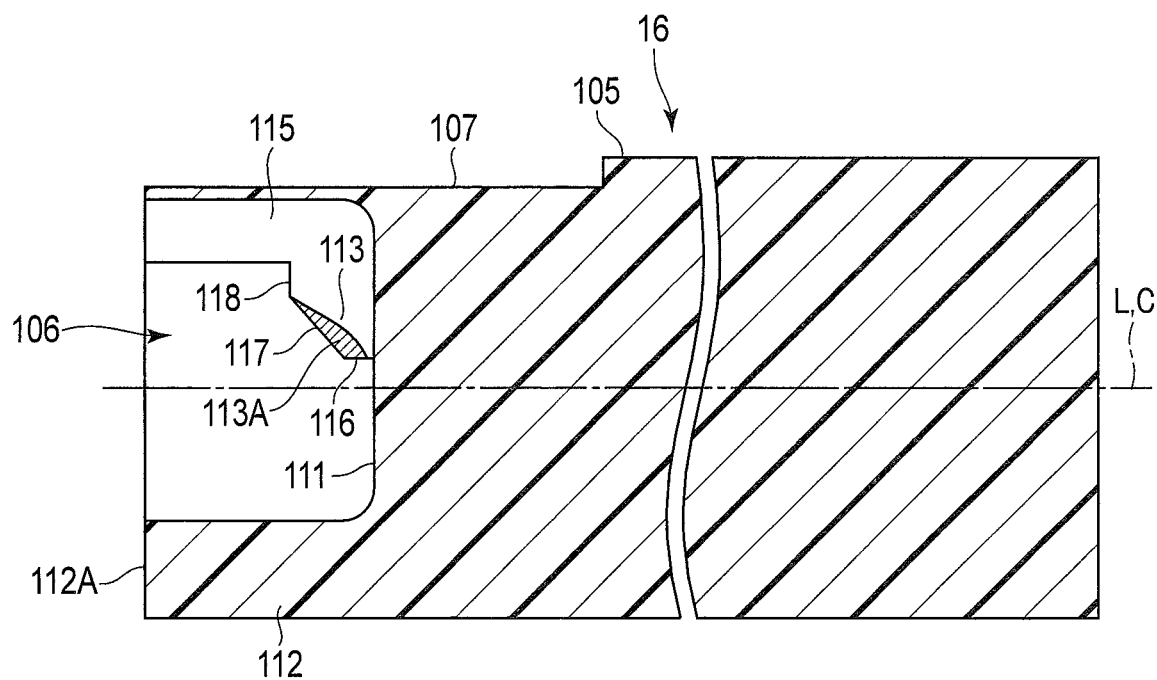
FIG. 18 is a cross-sectional view taken along line F18-F18 of the cover removing tool illustrated in FIG. 17.

As illustrated in FIG. 16, the cover removing tool 16 includes a columnar body 105. The outer periphery of the columnar body 105 is formed in a proper shape. As illustrated in FIG. 17, a working portion 106, which acts at a time of removing the cover 15 that is attached to the distal structure portion 24, is formed at one end of the columnar body 105. As illustrated in FIG. 16 to FIG. 18, the working portion 106 is formed in such a recess shape as to cover the vicinity of the closing portion 83 of the cover 15. An index 107, which enables the user to recognize the direction of the cover removing tool 16 in the circumferential direction around the axis of the longitudinal direction L, is formed on an outer peripheral surface of the columnar body 105. Here, the index 107 is formed as such a planar surface as to enable recognition of the direction by the touch. It is preferable that the index 107 is formed at a position neighboring the working portion 106.

The index 107 enables the user to recognize, by the naked eyes, etc., the position of insertion relative to the distal structure portion 24 to which the cover 15 is attached. The index 107 may be characters such as "UP", or may be an imprinted arrow indicative of the rotational direction. In this manner, the outer shape of the cover removing tool 16 is not particularly limited.

As illustrated in FIG. 17 and FIG. 18, the working portion 106 includes a bottom portion 111 which abuts on the distal end of the cover 15; a cylindrical portion 112 which projects from the bottom portion 111 and can cover the periphery of the cover 15; an end face 112A provided at the distal end of the cylindrical portion 112; a first projection portion 113 (abutment portion) which is engaged in the U-shaped recess portion 85B of the opening edge portion 85 of the cover 15 (the opening portion of the cover 15); a second projection portion 114 which is engaged with the distal covering portion 86 of the cover body 81, which is flush with the planar portion 61 of the distal structure portion 24; and a run-off portion 115 in which a part of the right-side edge portion 85A of the opening edge portion 85 of the destroyed cover 15 is disposed. The first projection portion 113 (projection) includes a stepped portion 116 extending in the longitudinal direction L (L direction); an inclined portion 117 which is inclined in a direction away from the center axis C toward the proximal direction C2 side of the center axis C direction; and a top surface portion 118 provided on the proximal direction C2 side of the center axis C direction. As illustrated in FIG. 19, the inclined portion 117 extends in a direction along a locus A which the distal end portion 25B of the pivot base 25 describes, at a position apart from the locus A. Thus, even if the pivot base 25 rotates by a small distance in the state in which the cover removing tool 16 is engaged with the cover 15, the distal end portion 25B of the pivot base 25 does not interfere with the inclined portion 117.

As illustrated in FIG. 19, the working portion 106 at one end of the columnar body 105 of the cover removing tool 16 is engaged with the distal structure portion 24 to which the cover 15 is attached. A distal surface of the closing portion 83 of the cover 15 abuts on the bottom surface 111.

By the cylindrical portion 112, the center axis C of the working portion 106 is defined. The distance, i.e. the radius, between the center axis C and the inner peripheral surface of the cylindrical portion 112, is set to be slightly greater than the radius defined by the rotational circumferential surface 104 of the cover 15. Thus, the rotational circumferential surface 104 of the cover 15 is abutted on, and supported by, the inner peripheral surface of the cylindrical portion 112. At this time, the cylindrical portion 112 is movable relative to the rotational circumferential surface 104 around the center axis C (see FIG. 16, FIG. 19, FIG. 20 and FIG. 22).

The width of the first projection portion 113 is set to be slightly smaller than the width of the recess portion 85B of the cover 15. As illustrated in FIG. 18, the first projection portion 113 of the cover removing tool 16 includes a pushing portion 113A. The pushing portion 113A is abutted on a to-be-pushed portion (edge) 88 (see FIG. 15) between the recess portion 85B and right-side edge portion 85A of the opening edge portion 85 of the cover 15.

The second projection portion 114 illustrated in FIG. 17 projects toward the end face 112A of the columnar body 105, relative to the bottom portion 111. The second projection portion 114 neighbors the first projection portion 113 in the circumferential direction about the center axis C. It is preferable that the second projection portion 114 is parallel to the planar portion 61. The second projection portion 114 can be abutted on the distal covering portion 86 of the distal edge portion 85C of the cover 15.

As illustrated in FIG. 19, the cover removing tool 16 is formed to have the following relationship in dimension. A dimension D in the longitudinal direction L from the bottom portion 111 to the end face 112A of the cylindrical portion 112 is greater than a dimension L1 from the bottom portion 111 to the rotational shaft 54. In addition, the dimension D in the longitudinal direction L from the bottom portion 111 to the end face 112A of the cylindrical portion 112 is less than a dimension L2 from the bottom portion 111 to the fragile portion 99.

The functions of the cover removing tool 16 for removing the cover 15, which is attached to the distal structure portion 24, and the rotational shaft 54 (bearing 65) will be described.

As illustrated in FIG. 16, the working portion 106 of the cover removing tool 16 is opposed to the distal structure portion 24 to which the cover 15 is attached. The direction of the index 107 is set in a parallel state to the planar portion 61 of the distal structure portion 24. As illustrated in FIG. 19, in this state, the working portion 106 of the cover removing tool 16 is engaged with the distal structure portion 24 to which the cover 15 is attached. The center axis C of the working portion 106 of the cylindrical portion 112 of the cover removing tool 16 is aligned with the center axis C of the rotational circumferential surface 104 of the cover 15, and the distal surface 25A of the closing portion 83 of the cover 15 is abutted on the bottom portion 111 of the working portion 106 of the cover removing portion 16. Thereby, there occur states illustrated in FIG. 20 and FIG. 22.

As illustrated in FIG. 19 and FIG. 20, at this time, the first projection portion 113 of the cover removing tool 16 is engaged in the recess portion 85B of the opening edge portion 85 of the cover 15. The second projection portion 114 of the cover removing tool 16 is disposed close to, or abutted on, the distal covering portion 86 of the cover 15.

In the state in which the distal structure portion 24 or the vicinity of the distal portion of the insertion section 21 is held and the distal surface of the closing portion 83 of the cover 15 is abutted on the bottom portion 111 of the cover removing tool 16, the cover removing tool 16 is rotated in a direction indicated by an arrow R in FIG. 16, relative to the distal structure portion 24 and the cover 15. Specifically, the cylindrical portion 112 of the cover removing tool 16 is rotated about the center axis C of the rotational circumferential surface 104, relative to the rotational circumferential surface 104 of the cover 15.

Figure 22:
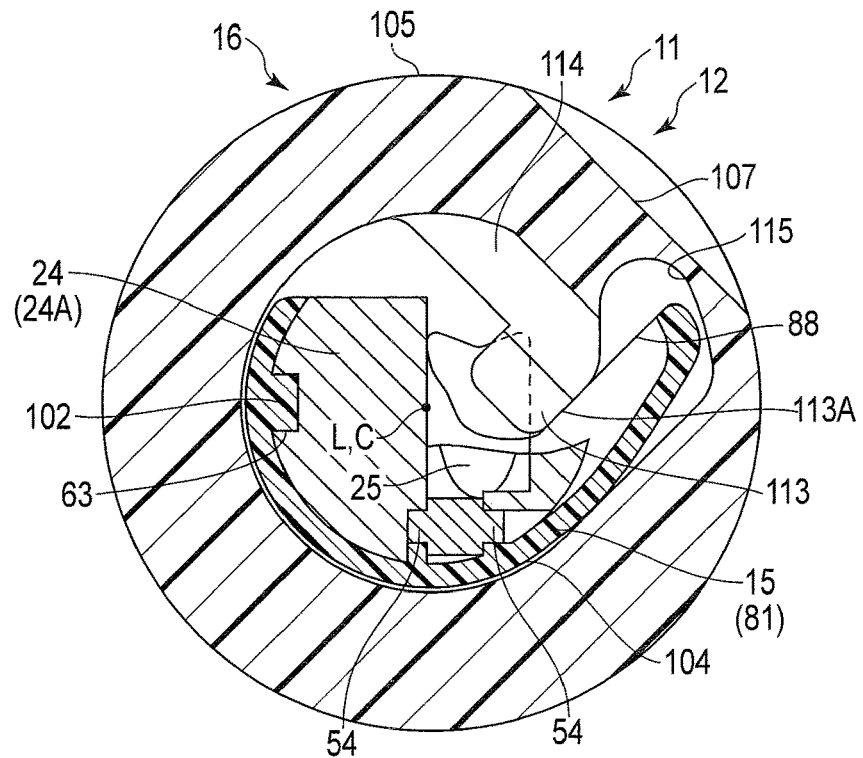
FIG. 22 is a cross-sectional view illustrating the distal structure portion, cover, etc. in a state after the cover removing tool was rotated by a predetermined angle and a coupling portion was broken at a position along line F22-F22 in FIG. 19.

Thereby, as illustrated in FIG. 22, while the opposed surface of the second projection portion 114 is moved away from the distal covering portion 86, the pushing portion 113A of the first projection portion 113 pushes the to-be-pushed portion 88 (edge) of the right-side edge portion 85A of the opening edge portion 85.

At this time, the guide projection portion 102 of the cover 15 keeps the state in which the guide projection portion 102 is engaged in the guide groove 63 of the distal structure portion 24. Thus, the guide projection portion 102 restricts the movement of the cover body 81 about the center axis C, relative to the distal structure portion 24.

Figure 23:
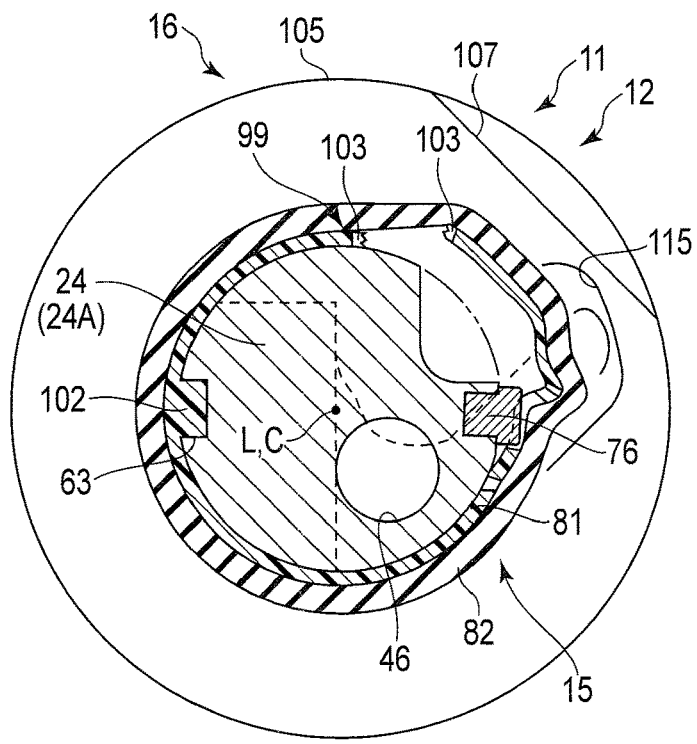
FIG. 23 is a cross-sectional view illustrating the distal structure portion, cover, etc. in a state after the cover removing tool was rotated by a predetermined angle and the coupling portion was broken at a position along line F23-F23 in FIG. 19.

Accordingly, the amount of working force of the cover removing tool 16 is applied to the coupling portion 103 between the slits 101 of the cover 15, which is opposed to the first projection portion 113 of the cover removing tool 16, through the to-be-pushed portion 88, right-side edge portion 85A and proximal edge portion 85E. Thereby, a stress concentrates at the fragile portion 99 of the cover 15, and the coupling portion is broken as illustrated in FIG. 23. By the breakage of the coupling portion 103, that part of the engaging portion 87 of the annular portion 84, which includes the engaging recess portion 98, moves in the circumferential direction, while the state is maintained in which the guide projection portion 102 of the cover 15 is engaged in the guide groove 63 of the distal structure portion 24. At this time, by the momentum of release of the stress due to the breakage of the coupling portion 103 of the fragile portion 99, the engaging recess portion 98 of the cover 15 can be disengaged from the engaging pin 76 of the distal structure portion 24. Thus, the breakage of the fragile portion 99 and the disengagement between the engaging pin 76 and the engaging recess portion 98 can be performed substantially at the same time.

In the present embodiment, in particular, the distance of engagement between the guide groove 63 of the distal structure portion 24 and the guide projection portion 102 of the cover 15 is set to be long. Thus, when the cover 15 is destroyed by using the cover removing tool 16, the pushing force on the cover 15 is concentrated by the breakage of the fragile portion 99 and the disengagement between the engaging pin 76 and the engaging recess portion 68.

In addition, as described above, because of the relationship of dimension L1<dimension D<dimension L2, when the cover removing tool 16 is rotated in the R direction, the rotational shaft 54, the bearing 65 and the track 72B of the alignment portion 72 are located in the inside of the cylindrical portion 112. Moreover, since the alignment portion 72 is located on the opposite side to the fragile portion 99 (e.g. on the opposite side by about) 180°, the deformation of the cover 15 due to breakage of the fragile portion 99 does not affect the alignment portion 72 side. Thus, when the fragile portion 99 is destroyed, the positions of the rotational shaft 54, the bearing 65 and the track 72B of the alignment portion 72 do not change. Accordingly, while the cover removing tool 16 is rotating, the rotational shaft 54 does not drop from the bearing 65, and the pivot base 25 is prevented from being erroneously damaged by the cover removing tool 16.

In the meantime, as illustrated in FIG. 22, the right-side edge portion 85A enters the run-off portion 115 of the cover removing tool 16. If the cover removing tool 16 is further rotated in the direction of the arrow R in FIG. 16, relative to the distal structure portion 24 and the cover 15, the user of the cover removing tool 16 is required to apply a force for bending the right-side edge portion 85A. Thus, the cylindrical portion 112 of the cover removing tool 16 becomes less easily slidable around the center axis C, relative to the rotational circumferential surface 104 of the cover 15. The user of the cover removing tool 16 recognizes this state. Accordingly, if the user of the cover removing tool 16 rotates the cover removing tool 16 in the direction of the arrow R, relative to the distal structure portion 24 and the cover 15, the coupling portion 103 is broken as illustrated in FIG. 23. Then, the user feels a proper drag until the engagement between the engaging pin 76 and the engaging recess portion 98 is released. Thereafter, the drag decreases, and then the user feels the drag once again. By feeling the second drag, the user can recognize that the breakage of the coupling portion 103 is completed.

At this time, the first projection portion 113 and second projection portion 114 come in contact with none of parts of the distal structure portion 24. Thus, when the cover 15 is removed from the distal structure portion 24 by the cover removing tool 16, a load is prevented from acting on the distal structure portion 24. In short, the distal structure portion 24 is not damaged.

In addition, the cover removing tool 16 is drawn out to the distal direction C1 side along the longitudinal direction L, from the cover 15 in which the fragile portion 99 was broken and broken portions 103 were formed. In this state, the user can directly observe the state in which the fragile portion 99 was broken. Since the fragile portion 99 was broken and the engaging recess portion 98 was disengaged from the engaging pin 76 of the distal structure portion 24, the cover 15 can be held by the user's fingers, a forceps, etc., and the cover 15 can be removed from the distal structure portion 24 to the distal direction C1 side along the longitudinal direction L. Thus, if the cover removing tool 16 is used, the user can more easily remove the cover 15 in the state in which the hygienic safety for the user (surgeon or staff) is secured. Incidentally, depending on the state of breakage, there may be a case in which the cover 15, together with the cover removing tool 16, is removed from the distal structure portion 24. The removed cover 15 is discarded.

Besides, in the state in which the distal structure portion 24 is held, if the cover removing tool 16 is rotated in a direction opposite to the direction indicated by the arrow R in FIG. 16, relative to the distal structure portion 24 and cover 15, the first projection portion 113 of the cover removing tool 16 pushes the wall surface of the storage portion 62. In addition, the state is maintained in which the opposed surface of the second projection portion 114 abuts on the distal covering portion 86 of the distal edge portion 85C of the cover 15. Thus, it is not possible that the user erroneously rotates the cover removing tool 16 in the direction opposite to the direction indicated by the arrow R.

The endoscope 12, from which the cover 15 was removed, that is, the insertion section 21 including the distal structure portion 24, the operation section 22 and the universal cord 23, are properly cleaned, disinfected and sterilized for reuse. In the present embodiment, as illustrated in FIG. 13 and FIG. 14, by lifting the rotational shaft 54 from the bottom 65A of the bearing 65, the passage of a brush or the like is facilitated at a time of cleaning, and the cleaning performance of the distal structure portion 24 is improved.

As illustrated in FIG. 13, in the state in which the pivot base 25 is in the fallen position P1, the user pushes the vicinity of a distal chamfered portion 25C of the pivot base 25 from a direction indicated by an arrow A. Thereby, a gap G1 can be created between the bottom 65A of the bearing 65 and the rotational shaft 54. As illustrated in FIG. 14, in the state in which the pivot base 25 is in the raised position P2, the user pushes the vicinity of the distal end portion 25B of the pivot base 25 from a direction indicated by an arrow B. Thereby, a gap G2 can be created between the bottom 65A of the bearing 65 and the rotational shaft 54. In this manner, in the present embodiment, in each of the states of the fallen position P1 and raised position P2, the gap can be created between the bottom 65A of the bearing 65 and the rotational shaft 54. Therefore, usability is high for the user who performs cleaning. After the cleaning, disinfection and sterilization are performed, and a new cover 15 is properly attached to the distal structure portion 24. Thereby, the endoscope system 11 can be used for the next-time observation and treatment.

As has been described above, according to the endoscope 12 of this embodiment, the following can be said. The endoscope 12 (endoscope system 11) includes the rigid distal structure portion 24 provided on the distal side of the insertion section 21 which is inserted in a subject; the rotational portion including the rotational shaft 54 which is held to be rotatable relative to the distal structure portion 24, and configured to rotate about the rotational shaft 54; the exterior member detachably attached to the distal structure portion 24; the bearing 65 opposed to the exterior member and recessed from the outer surface of the distal structure portion 24, the bearing 65 being configured to receive and support the rotational shaft 54 and to displace the rotational shaft 54 from the distal structure portion 24 by the exterior member being removed from the distal structure portion 24; and the preventing portion 66 provided on one of the rotational portion and the distal structure portion 24, and configured to prevent disengagement of the rotational portion by coming in contact with the other of the rotational portion and the distal structure portion 24 when the rotational shaft 65 is displaced from the bearing 65.

According to this configuration, when the exterior member was removed from the distal structure portion 24 at a time of maintenance, the rotational shaft 54 can be displaced from the bearing 65. Thus, a brush or the like for cleaning can easily be passed through areas surrounding the rotational shaft 54 and bearing 65, and workability can be enhanced when the user cleans these parts. Thereby, there can be provided the endoscope 12 (endoscope system 11) which the user can easily use.

The preventing portion 66 restricts disengagement of the rotational portion in a position where the rotational portion is not raised relative to the distal structure portion 24. Usually, for the smoothing of work, it is preferable to attach/detach the exterior member in the state in which the rotational portion is not raised. According to this configuration, when the exterior member is attached/detached, the rotational portion is not disengaged from the distal structural portion 24, and it is possible to prevent a risk of damage to the rotational portion which is disengaged.

In this case, the guide portion 67 is provided which guides the preventing portion 66 when the rotational portion is rotated relative to the distal structure portion 24. According to this configuration, the rotation of the rotational portion can be guided by utilizing the guide portion 67 and preventing portion 66. Compared to the configuration in which the rotational portion is supported by only the rotational shaft 54, the attitude of the rotational portion can be stabilized.

The endoscope 12 includes the restriction portion 68 which restricts the range of rotation of the rotational portion relative to the distal structure portion 24. According to this configuration, the position of the rotational portion can be restricted within a predetermined range by the restriction portion 68. Thereby, for example, when the exterior member is attached to the distal structure portion 24, it is possible to prevent the rotational portion from coming in contact with the exterior member and damaging the exterior member or the rotational portion. In addition, for example, in the state in which the exterior member is detached, it is possible to prevent the exterior member and rotational portion from colliding and being damaged, when the exterior member is attached to the distal structure portion 24 once again.

The exterior member includes the alignment portion 72. The alignment portion 72 aligns the rotational shaft 54 in a predetermined position in the bearing 65, when the exterior member is attached to the distal structure portion 24. According to this configuration, when the exterior member is attached to the distal structure portion 24, the rotational shaft 54 can automatically be aligned in the predetermined position in the bearing 65 by the alignment portion 72, and the rotational shaft 54 can be restored to the original position without the user being aware of the alignment. Thereby, when the rotational portion is restored to the original position, the user is not required to do time-consuming work, and the user-friendly endoscope 12 with good efficiency in maintenance can be provided.

In this case, when the exterior member is attached to the distal structure portion 24 in a direction along the longitudinal direction L of the insertion section 21, the alignment portion 72 moves the rotational shaft 54 in the direction X crossing the longitudinal direction L, and aligns the rotational shaft 54 in the predetermined position in the bearing 65. According to this configuration, the rotational shaft 54 can be aligned by utilizing the operation of attaching the exterior member, without the user being aware of the alignment, and the user-friendly endoscope can be realized.

The alignment portion 72 includes the inclined surface 72A which is provided on the inner surface of the exterior member in a manner to project toward the distal structure portion 24. The inclined surface 72A guides the rotational shaft 54 to the predetermined position in the bearing 65, when the exterior member is attached to the distal structure portion 24. According to this configuration, by the inclined surface 72A, a cam structure can be realized which converts an attachment movement of the exterior member to a movement in the direction X crossing the direction of the attachment movement. When the exterior member is attached and the rotational shaft 54 is aligned in the predetermined position in the bearing 65, the load on the user's hand and fingers can be reduced.

The alignment portion 72 includes the track 72B which is continuous with the inclined surface 72A, the track 72B being provided on the inner surface of the exterior member in a manner to project toward the distal structure portion 24. The track 72B holds the rotational shaft 54 in the predetermined position in the bearing 65. According to this configuration, the rotational shaft 54, which has been guided by the inclined surface 72A, can be held in the predetermined position in the bearing 65 by the track 72B. Thus, the alignment portion 72 can be realized by the simple configuration including the inclined surface 72A and track 72B, and the configuration of the exterior member can be simplified. In addition, since the alignment portion 72 is, like the guide projection 102, elongated in the longitudinal direction (L direction), the alignment portion 72 functions like a rib of the cover body 81. Thus, the alignment portion 72 contributes to an improvement of rigidity of the cover body 81 (cover 15), and can make the cover body 81 less crushable.

The rotational portion is a treatment instrument raising base which raises a treatment instrument that is inserted in the subject along the insertion section 21. According to this configuration, it is possible to improve the ease in cleaning of the rotational shaft 54 of the treatment instrument raising base, and to provide a user-friendly endoscope.

The endoscope 12 includes the rigid distal structure portion 24 provided on the distal side of the insertion section 21 which is inserted in a subject; the rotational portion including the rotational shaft 54 which is held to be rotatable relative to the distal structure portion 24, and configured to rotate about the rotational shaft 54; the exterior member detachably attached to the distal structure portion 24 in a manner to cover at least a part of the distal structure portion 24; the bearing 65 opposed to the exterior member and recessed from the outer surface of the distal structure portion 24, the bearing 65 being configured to displace the rotational shaft 54 from the distal structure portion 24 by the exterior member being removed from the distal structure portion 24; and the alignment portion 72 provided on the exterior member and configured to move, when the exterior member is attached to the distal structure portion 24, the rotational shaft 54 in the direction X crossing the longitudinal direction L of the insertion section 21, and to align the rotational shaft 54 in a predetermined position in the bearing 65.

According to this configuration, the alignment portion 72, which moves the rotational shaft 54 in the direction X crossing the longitudinal direction L of the insertion section 21, can be provided on the exterior member. Thereby, a configuration is realized in which the alignment of the rotational shaft 54 is automatically released when the exterior member was removed. Therefore, it is possible to realize the configuration in which the rotational shaft 54 is displaced from the bearing 65 when the exterior member is removed, and the bearing 65 and rotational shaft 54 are easily cleaned, and to realize the user-friendly endoscope 12.

The endoscope system 11 includes the exterior member removing tool which is rotatable relative to the exterior member, the exterior member removing tool including the bottom portion 111 which abuts on the distal end of the exterior member; the cylindrical portion 112 which projects from the bottom portion 111 and is capable of covering the periphery of the exterior member; and the abutment portion which is provided in the inside of the cylindrical portion 112, abuts on the opening portion provided in the exterior member when the exterior member removing tool is rotated relative to the exterior member, and breaks the fragile portion 99 of the exterior member. The dimension D in the longitudinal direction L from the bottom portion 111 to the end face 112A of the cylindrical portion 112 is greater than the dimension L1 in the longitudinal direction L from the bottom portion 111 to the rotational shaft 54, and is less than the dimension L2 in the longitudinal direction L from the bottom portion 111 to the fragile portion 99.

According to this configuration, when the cylindrical portion 112 is rotated in order to break the fragile portion 99, the rotational shaft 54 and bearing 65 can be located in the inside of the cylindrical portion 112. Thereby, it is possible to prevent such a risk that the rotational shaft 54 drops from the bearing 65 when the cylindrical portion 112 is rotated, and the rotational portion is involved in the rotation of the cylindrical portion 112 and damaged. Thus, a more user-friendly endoscope system 11 can be realized.

Hereinafter, a second embodiment to an eleventh embodiment, in which parts of the first embodiment are modified, will be described. In the embodiments below, different parts from the first embodiment will mainly be described, and a description of parts common to the first embodiment will be omitted.

Second Embodiment

A second embodiment of the endoscope system 11 will be described with reference to FIG. 24 to FIG. 28.

Figure 25:
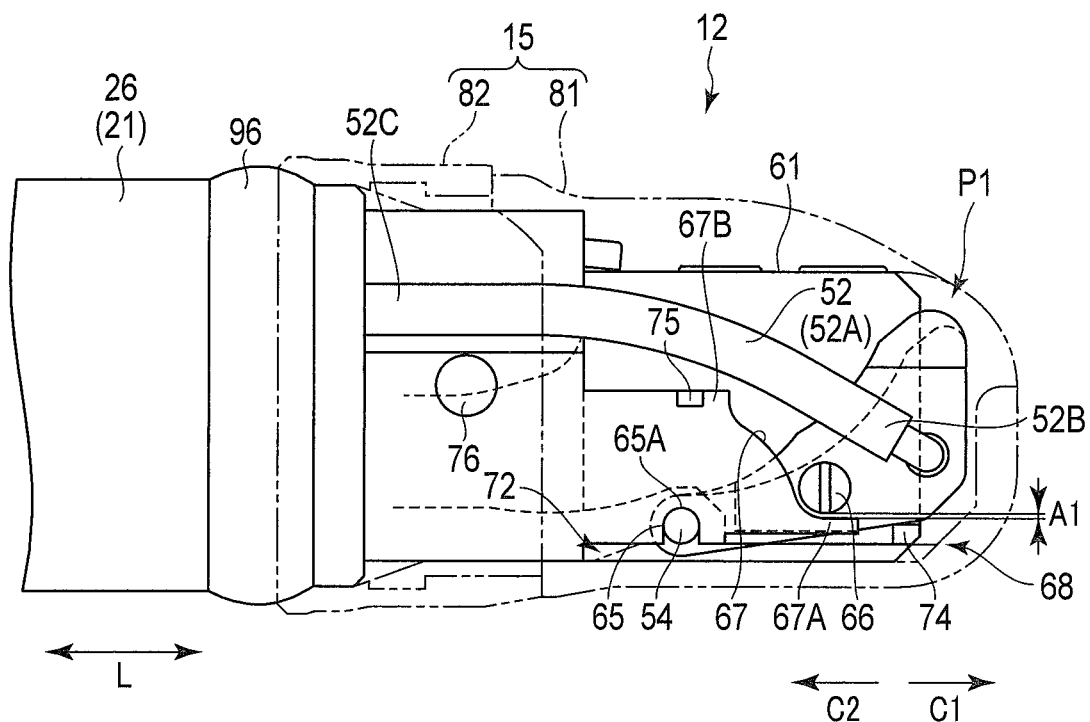
FIG. 25 is a side view illustrating the distal structure portion, cover and pivot base illustrated in FIG. 24, in a state in which the pivot base is in a fallen position.
Figure 26:
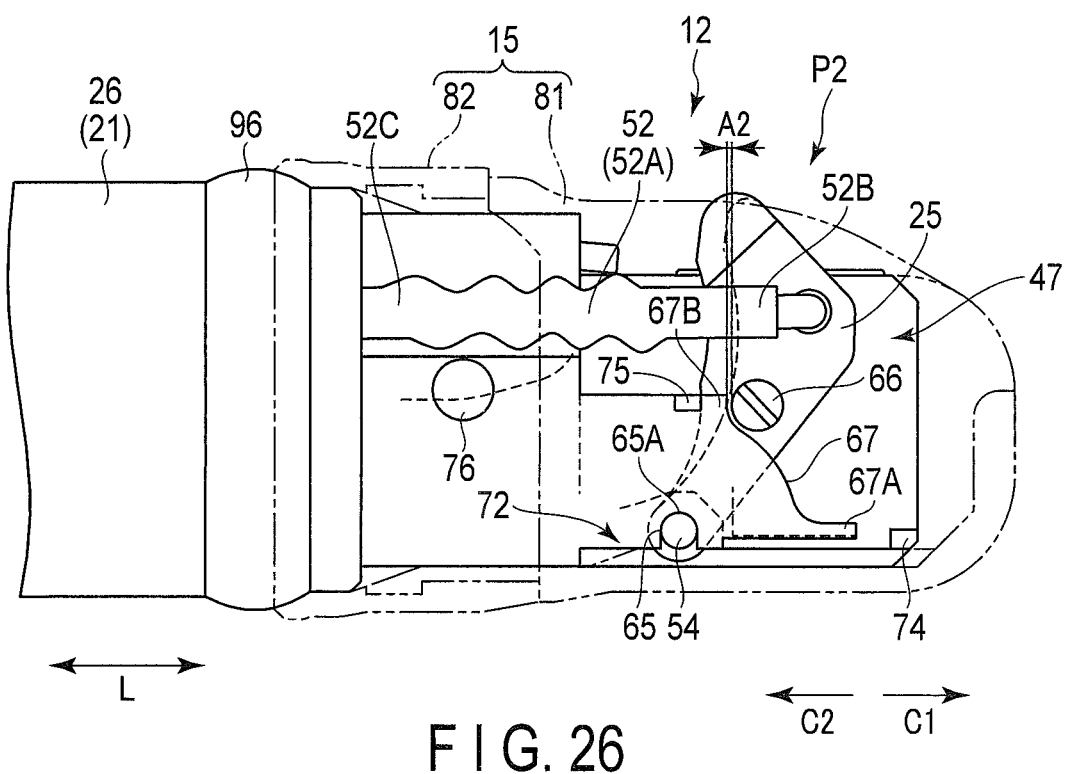
FIG. 26 is a side view illustrating the distal structure portion, cover and pivot base illustrated in FIG. 24, in a state in which the pivot base is in a raised position.

As illustrated in FIG. 24 and FIG. 26, a restriction portion 68 is provided separately from the guide portion 67. The restriction portion 68 includes a first stopper 74 which restricts the rotational angle of the pivot base 25 on the fallen position P1 side of the pivot base 25, and a second stopper 75 which restricts the rotational angle of the pivot base 25 on the raised position P2 side of the pivot base 25. The first stopper 74 and second stopper 75 are provided in a manner to project to the pivot base 25 from the main body 24A of the distal structure portion 24. As illustrated in FIGS. 25 and 26, in the present embodiment, the first stopper 74 and second stopper 75 directly abut on, not the preventing portion 66, but the pivot base 25, thereby restricting the rotational angle of the pivot base 25. As illustrated in FIG. 25, by the function of the first stopper 74, a gap A1 is created between a distal end portion 67A of the guide portion 67 and the preventing portion 66. As illustrated in FIG. 26, by the function of the second stopper 75, a gap A2 is created between a proximal end portion 67B of the guide portion 67 and the preventing portion 66.

The user can remove the cover 15 by using the cover removing tool 16 by the same method as in the first embodiment.

The endoscope 12, from which the cover 15 was removed, that is, the insertion section 21 including the distal structure portion 24, the operation section 22 and the universal cord 23, are properly cleaned, disinfected and sterilized for reuse. In the present embodiment, as illustrated in FIG. 27 and FIG. 28, by lifting the rotational shaft 54 from the bottom 65A of the bearing 65, the passage of a brush or the like is facilitated at a time of cleaning, and the cleaning performance of the distal structure portion 24 is improved. The rotational shaft 54 can be displaced relative to the bearing 65 (can be lifted relative to the bottom 65A of the bearing 65) when the pivot base 25 is in the fallen position P1 or the raised position P2.

As illustrated in FIG. 27, in the state in which the pivot base 25 is in the fallen position P1, the user pushes the vicinity of the distal chamfered portion 25C of the pivot base 25 from the direction indicated by the arrow A. Thereby, a gap G1' can be created between the bottom 65A of the bearing 65 and the rotational shaft 54. As illustrated in FIG. 28, in the state in which the pivot base 25 is in the raised position P2, the user pushes the vicinity of the distal end portion 25B of the pivot base 25 from the direction indicated by the arrow B. Thereby, a gap G2' can be created between the bottom 65A of the bearing 65 and the rotational shaft 54. In this manner, in the present embodiment, in each of the states of the fallen position P1 and raised position P2, the gap can be created between the bottom 65A of the bearing 65 and the rotational shaft 54. Therefore, usability is high for the user who performs cleaning. After the cleaning, disinfection and sterilization are performed, and a new cover 15 is properly attached to the distal structure portion 24. Thereby, the endoscope system 11 is used for the next-time observation and treatment.

According to the present embodiment, also when the restriction portion 68 is provided at a position separate from the guide portion 67, the gap G1' and gap G2' can be formed when the cover 15 is removed. Thereby, it is possible to realize the configuration in which the bearing 65 and rotational shaft 54 are easily cleaned when the cover 15 is removed, and to realize the user-friendly endoscope 12.

Third Embodiment

Figure 29:
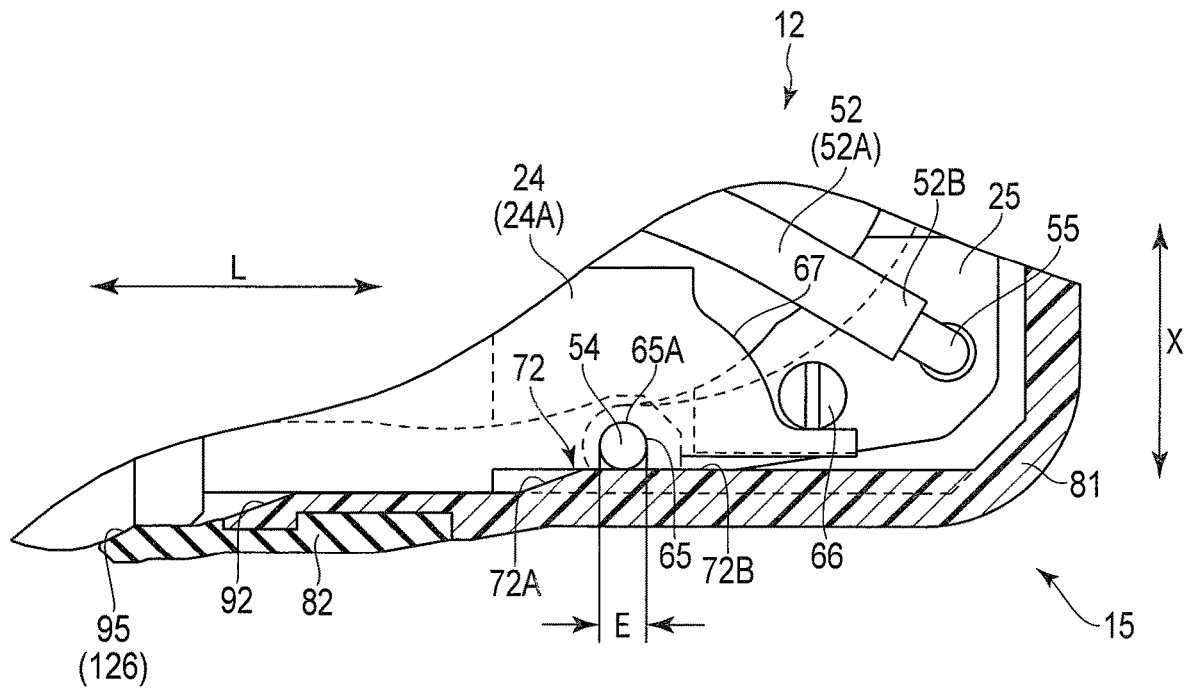
FIG. 29 is a cross-sectional view illustrating a distal structure portion and cover of an endoscope system of a third embodiment, FIG. 29 being taken along the longitudinal direction at a position of the rotational shaft.

A third embodiment of the endoscope system will be described with reference to FIG. 29.

In the present embodiment, the dimension of the bearing 65 in the longitudinal direction L of the insertion section 21 is greater than the dimension in the longitudinal direction L of the bearing 65 in the first embodiment. In addition, a dimension E of the bearing 65 in the longitudinal direction L is greater than the dimension of the bearing 65 in the direction X crossing the longitudinal direction L. Note that the dimension of the bearing 65 in the direction X crossing the longitudinal direction L is substantially equal to the diameter of the rotational shaft 54. On the other hand, in the present embodiment, after the cover 15 is attached, the alignment portion 72 pushes the rotational shaft 54 onto the bottom 65A of the bearing 65. Thus, the alignment portion 72 can determine the position of the rotational shaft 54 in the longitudinal direction L and the position of the rotational shaft 54 in the direction crossing the longitudinal direction L.

In the present embodiment, by the same method as in the first embodiment, the cover 15 is removed, and the rotational shaft 54 can be displaced relative to the bearing 65 (the rotational shaft 54 can be lifted from the bottom 65A of the bearing 65). Moreover, in this embodiment, compared to the bearing 65 of the first embodiment, the dimension E of the bearing 65 in the longitudinal direction L is set to be greater. Thus, in each of the state after the rotational shaft 54 is displaced from the bearing 65 and the state before the rotational shaft 54 is displaced from the bearing 65, a brush or the like for cleaning can easily be passed into the bearing 65. Thereby, at a time of maintenance, the cleaning performance of the bearing 65 and rotational shaft 54 is improved, and the user-friendly endoscope 12 can be realized.

Fourth Embodiment

Figure 30:
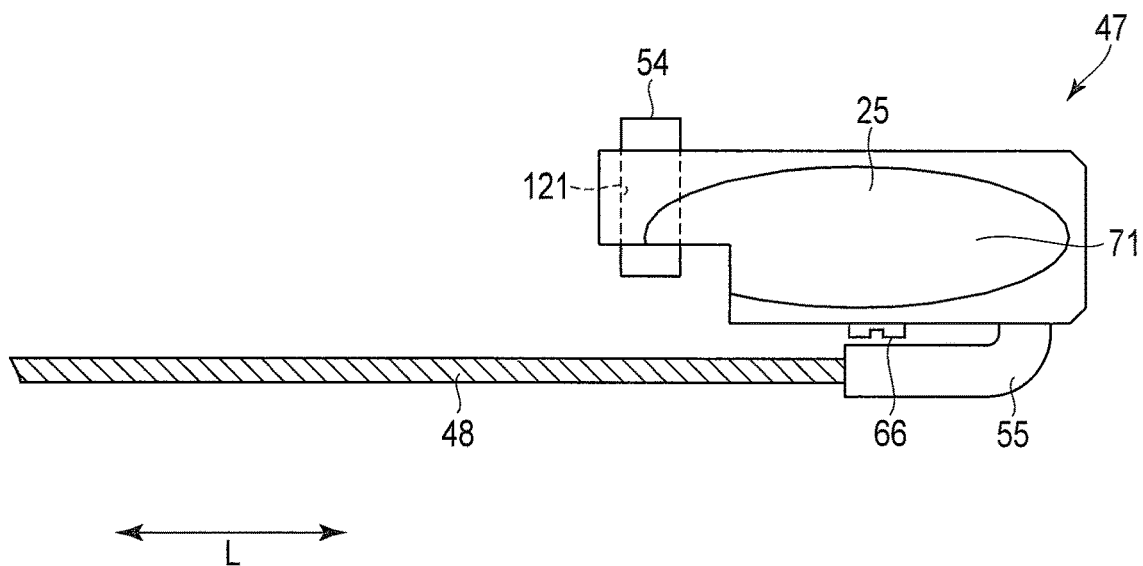
FIG. 30 is a plan view illustrating a pivot mechanism of an endoscope system of a fourth embodiment.

A fourth embodiment of the endoscope system 11 will be described with reference to FIG. 30.

The pivot base 25 includes a pivot base body 71, a rotational shaft 54 which is formed separate from the pivot base body 71, and a preventing portion 66 which prevents the rotational shaft 54 from dropping from the bearing 65 of the main body 24A. The rotational shaft 54 is inserted in a through-hole 121 formed in the pivot base body 71, and is fixed to the pivot base body 71. The rotational shaft 54 is fixed to the pivot base body 71 by an adhesive which is applied in the through-hole 121 with no gap. The method of fixing the rotational shaft 54 to the pivot base body 71 is not limited to this. The fixing method of the rotational shaft 54 may be, for example, brazing using a solder or the like, press-fitting of the rotational shaft 54 into the through-hole 121, or welding to the through-hole 121.

The rotational shaft 54 is provided to project on both sides in a direction crossing the longitudinal direction (L direction) from the pivot base body 71 of the pivot base 25. Thus, the rotational shaft 54 of the pivot base 25 is rotatably supported in a so-called both-end support fashion, such that the rotational shaft 54 is clamped between the bearing 65 of the distal structure portion 24 and the alignment portion 72 of the cover 15.

In the present embodiment, the elastic member 52 is omitted. Thus, the wire 48 is formed of, for example, a corrosion-resistant material (e.g. stainless steel), and is exposed in the wire moving section 51 of the distal structure portion 24. Even with this configuration, there is no problem in actual use.

In this embodiment, by the same method as in the first embodiment, the cover 15 is removed, the rotational shaft 54 is displaced from the bearing 65 (the rotational shaft 54 is lifted from the bottom 65A of the bearing 65), and the bearing 65 and rotational shaft 54 can be cleaned.

Also when the rotational shaft 54 is formed separate from the pivot base body 71 and the elastic member 52 is omitted as in the present embodiment, the cleaning performance of the bearing 65 and rotational shaft 54 can be improved at a time of maintenance. Thereby, the user-friendly endoscope can be realized.

Fifth Embodiment

A fifth embodiment of the endoscope system 11 will be described with reference to FIG. 31 and FIG. 32.

Figure 31:
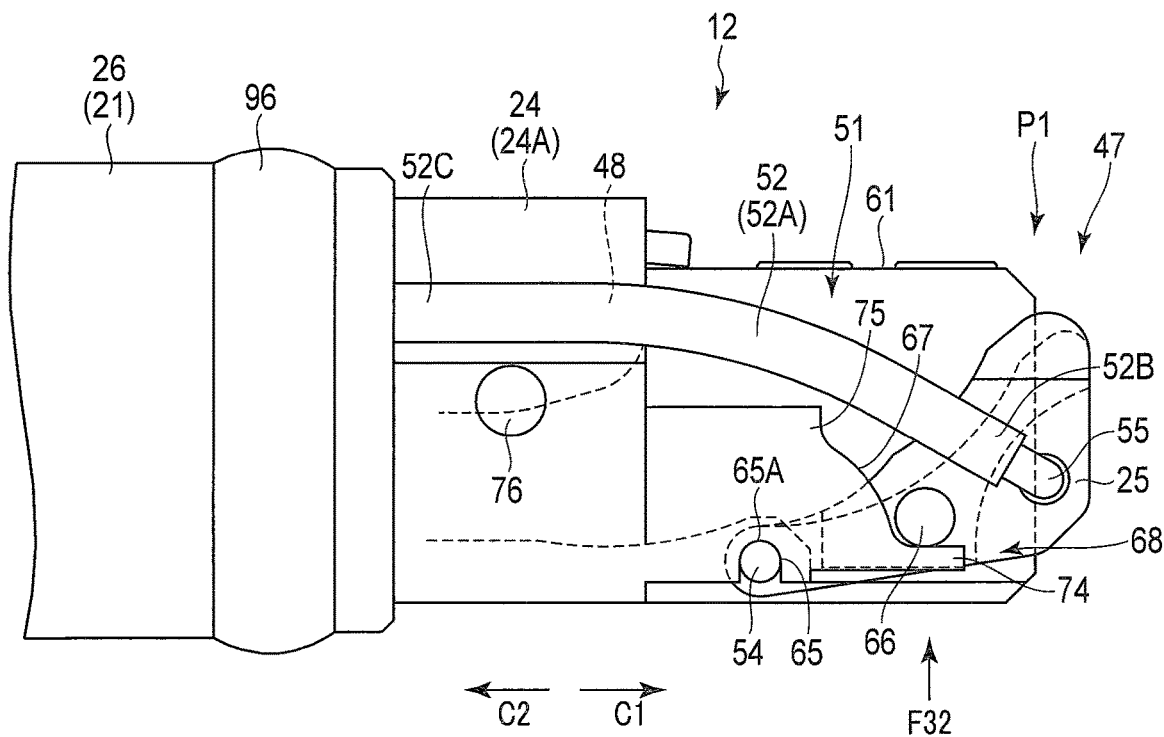
FIG. 31 is a side view illustrating a distal structure portion and a preventing portion in a state in which a cover is removed in an endoscope system of a fifth embodiment.
Figure 32:
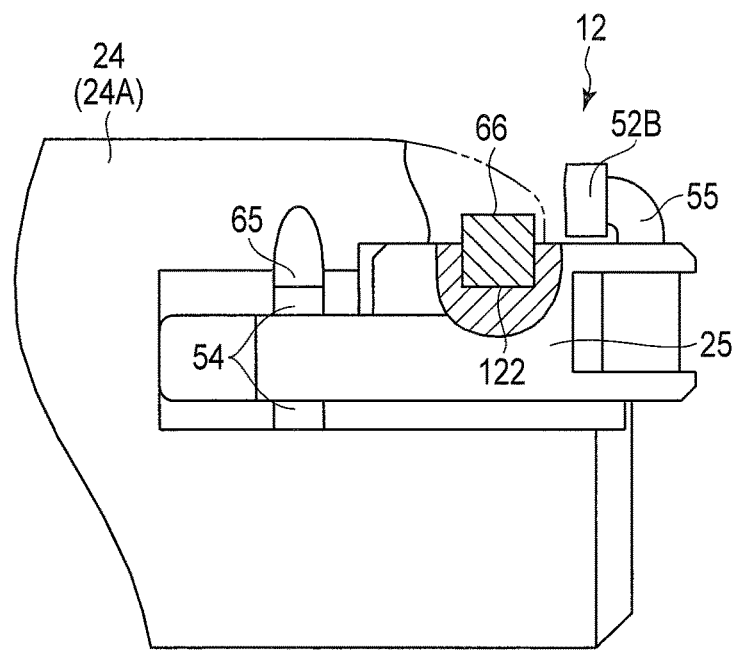
FIG. 32 is a bottom view as viewed in a direction of an arrow F32 in FIG. 31, with a part of the vicinity of the preventing portion being broken out.

As illustrated in FIG. 31 and FIG. 32, the preventing portion 66 is composed of a cylindrical pin which is fixed a hole 122 formed in the pivot base body 71 of the pivot base 25. In the present embodiment, like the first embodiment, the preventing portion 66 cooperates with the guide portion 67 and wire 48, thereby defining the displacement of the rotational shaft 54 (a distance of lifting of the rotational shaft 54 from the bottom 65A of the bearing 65). Specifically, the structure of the preventing portion 66 and guide portion 67 prevents the rotational shaft 54 from dropping from the bearing 65, and prevents the pivot base 25 from dropping from the distal structure portion 24.

The preventing portion 66 is fixed to the pivot base body 71, for example, by using an adhesive or the like. The method of fixing the preventing portion 66 to the pivot base body 71 is not limited to this. The method of fixing the preventing portion 66 to the pivot base body 71 may be, for example, brazing using a solder or the like, press-fitting of the preventing portion 66 into the hole 122, or welding to the hole 122.

In this embodiment, by the same method as in the first embodiment, the cover 15 is removed, the rotational shaft 54 is displaced from the bearing 65 (the rotational shaft 54 is lifted from the bottom 65A of the bearing 65), and the bearing 65 and rotational shaft 54 can be cleaned.

Also when the preventing portion 66 is formed of the pin, as in the present embodiment, the cleaning performance of the bearing 65 and rotational shaft 54 can be improved at a time of maintenance. Thereby, the user-friendly endoscope 12 can be realized.

Sixth Embodiment

Figure 33:
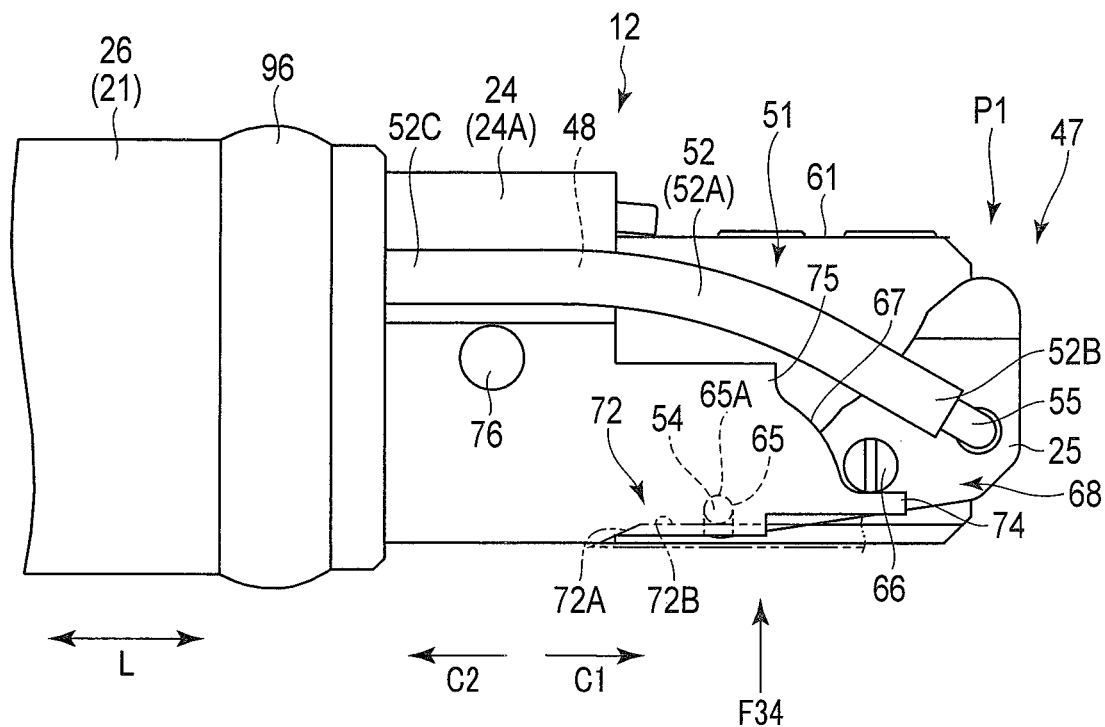
FIG. 33 is a side view illustrating a distal structure portion, rotational shaft and alignment portion in an endoscope system of a sixth embodiment.
Figure 34:
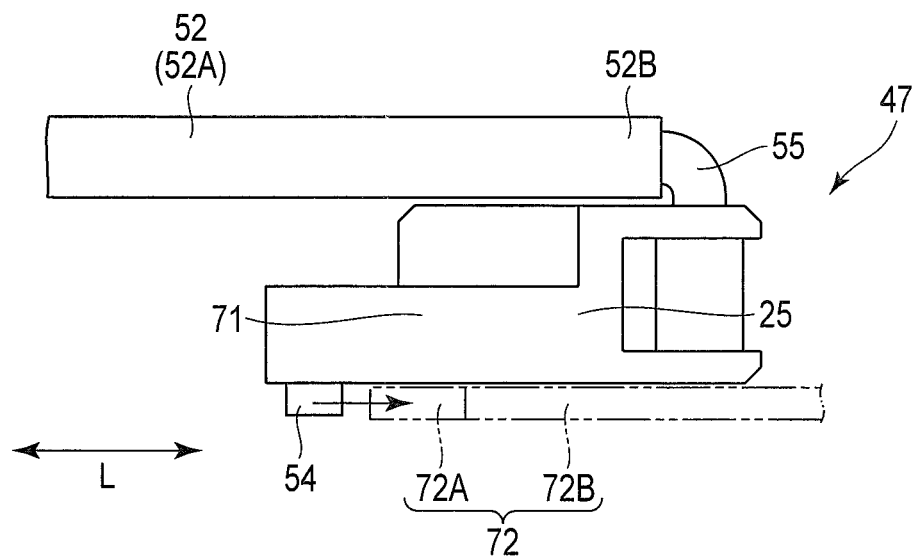
FIG. 34 is a bottom view illustrating a pivot mechanism (pivot base) as viewed in a direction of an arrow F34 in FIG. 33.

A sixth embodiment of the endoscope system 11 will be described with reference to FIG. 33 to FIG. 35.

The pivot base 25 includes a pivot base body 71, a rotational shaft 54 which is formed integral with the pivot base body 71, and a preventing portion 66 which prevents the rotational shaft 54 from dropping from the bearing 65 of the main body 24A. The rotational shaft 54 is provided to project on one side (a side opposite to the side on which the operating shaft portion 55 projects) in a direction crossing the longitudinal direction (L direction) from the pivot base body 71 of the pivot base 25.

Figure 35:
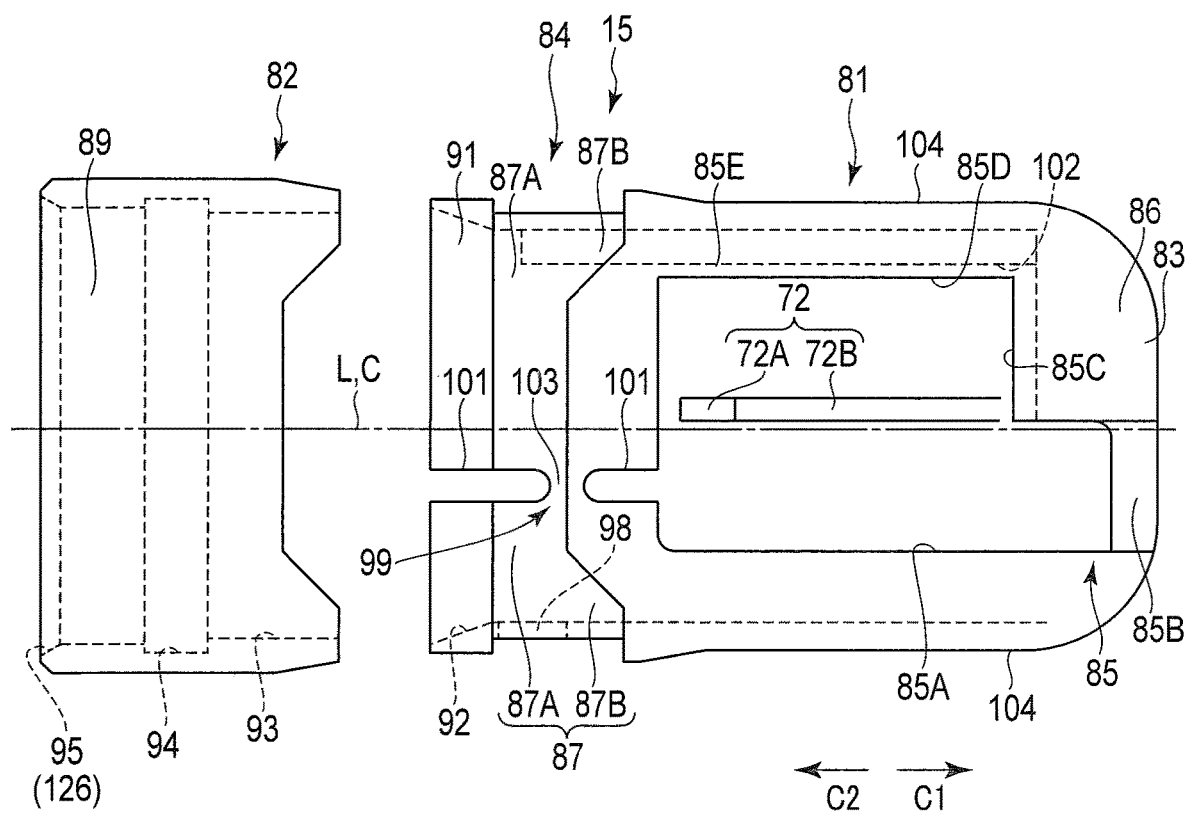
FIG. 35 is an exploded plan view of a cover of the endoscope system of the sixth embodiment.
Figure 36:
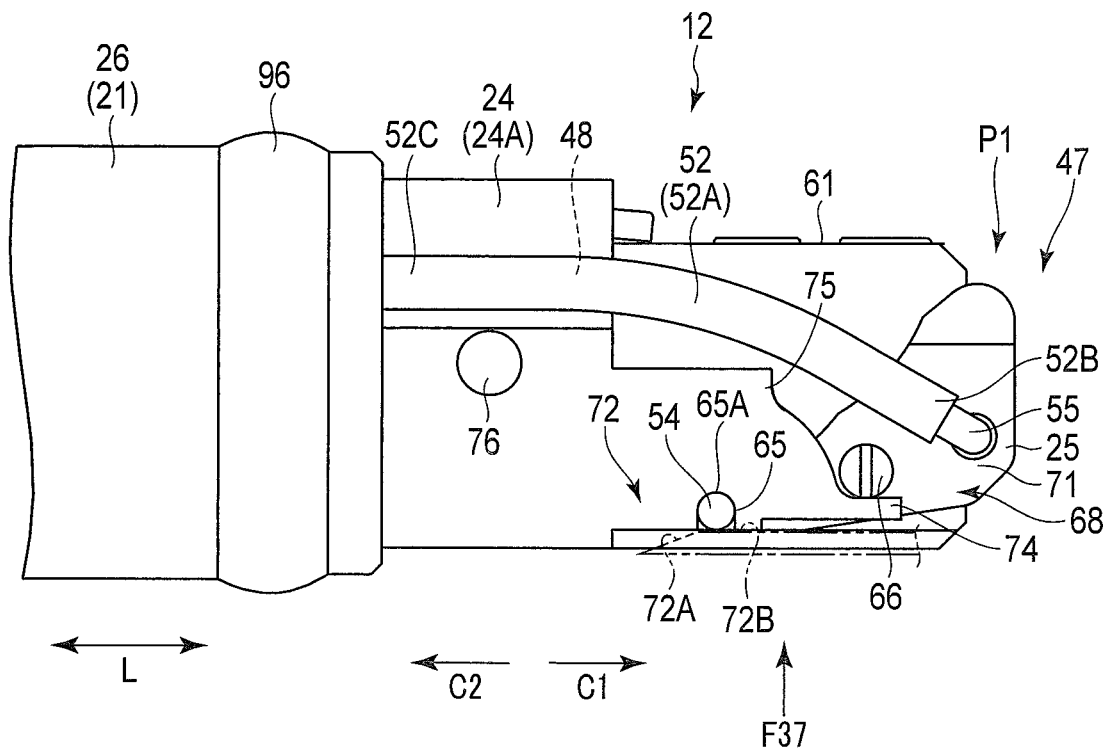
FIG. 36 is a side view illustrating a distal structure portion, rotational shaft and alignment portion in an endoscope system of a seventh embodiment.
Figure 37:
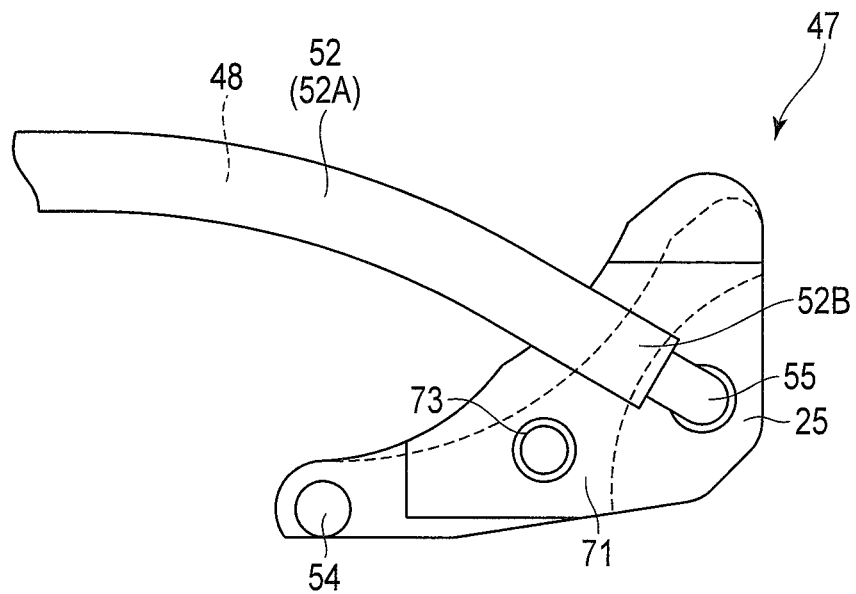
FIG. 37 is a side view illustrating, in enlarged scale, a pivot mechanism (pivot base) of the endoscope system illustrated in FIG. 36.
Figure 38:
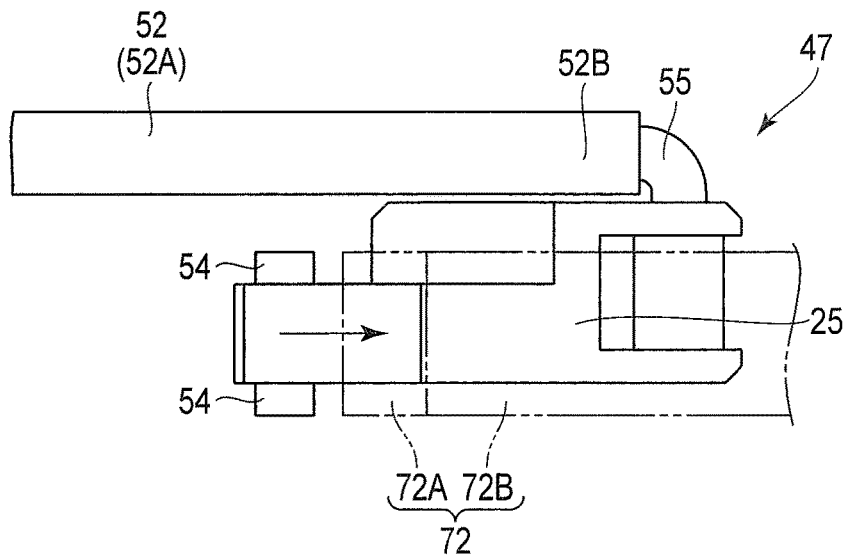
FIG. 38 is a bottom view illustrating the pivot mechanism (pivot base) as viewed in a direction of an arrow F37 in FIG. 36.
Figure 39:
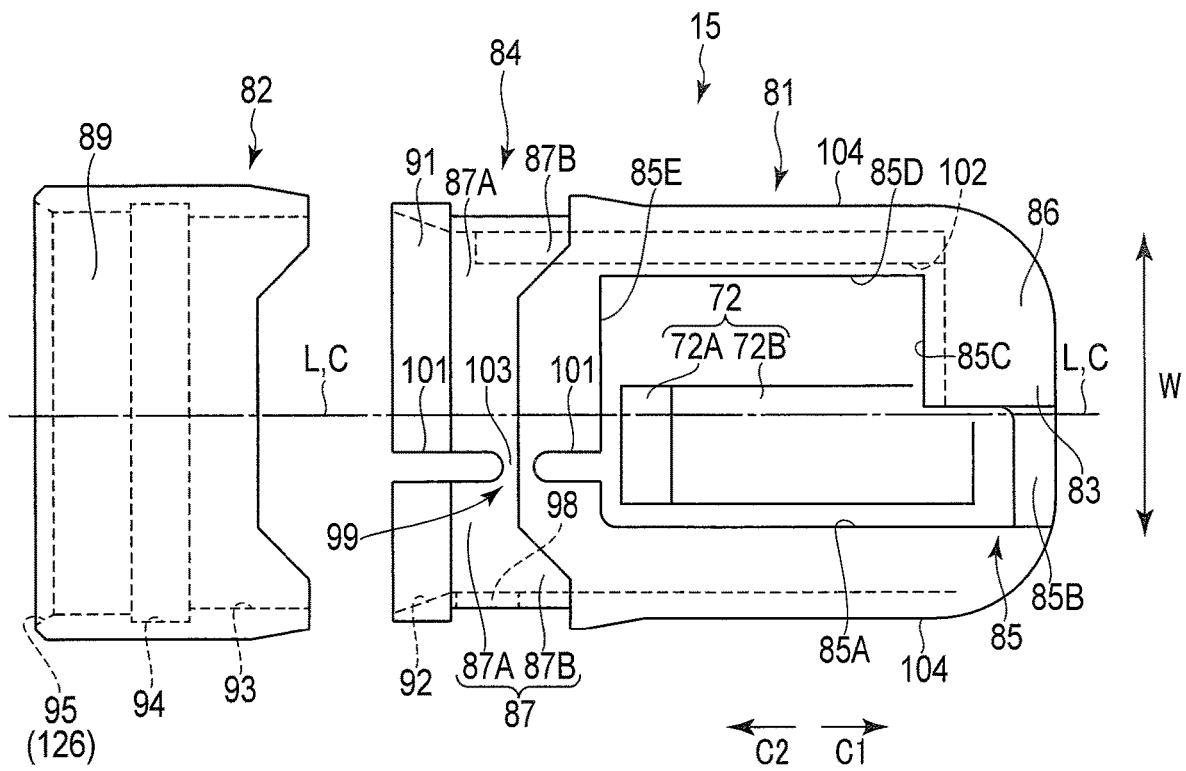
FIG. 39 is an exploded plan view of a cover of the endoscope system of the seventh embodiment.

As illustrated in FIG. 35, the alignment portion 72 is formed of one alignment portion having a projecting shape extending in the longitudinal direction (L direction). The alignment portion 72 includes an inclined surface 72A which gradually projects in an inward direction (direction toward the center axis C) toward the closing portion 83, and a track 72B extending from the inclined surface 72A in the longitudinal direction. The inclined surface 72A guides the rotational shaft 54 to the bearing 65 side, when the cover 15 is attached to the distal structure portion 24. The track 72B pushes the rotational shaft 54 onto the bearing 65, when the cover 15 is attached to the distal structure portion 24. After the cover 15 was attached to the distal structure portion 24, the track 72B abuts on the rotational shaft 54 and aligns the rotational shaft 54 in a predetermined position (bottom 65A) in the bearing 65. Thus, the rotational shaft 54 of the pivot base 25 is rotatably supported in a so-called cantilever support fashion, such that the rotational shaft 54 is clamped between the bearing 65 of the distal structure portion 24 and the alignment portion 72 of the cover 15.

In the present embodiment, by the same method as in the first embodiment, the cover 15 is removed, the rotational shaft 54 is displaced from the bearing 65 (the rotational shaft 54 is lifted from the bottom 65A of the bearing 65), and the bearing 65 and rotational shaft 54 can be cleaned.

According to this embodiment, also when the pivot base 25 is supported in the so-called cantilever support fashion, the cleaning performance of the bearing 65 and rotational shaft 54 can be improved at a time of maintenance. Thereby, the user-friendly endoscope 12 can be realized.

Seventh Embodiment

A seventh embodiment of the endoscope system 11 will be described with reference to FIG. 36 to FIG. 39.

The pivot base 25 includes a pivot base body 71, a rotational shaft 54 which is formed integral with the pivot base body 71, and a preventing portion 66 which prevents the rotational shaft 54 from dropping from the bearing 65 of the main body 24A. The rotational shaft 54 is provided to project on both sides in a direction crossing the longitudinal direction (L direction) from the pivot base body 71 of the pivot base 25.

The alignment portion 72 is formed of one large-width alignment portion having a projecting shape extending in the longitudinal direction (L direction). A width dimension of the alignment portion 72 in the direction W crossing the longitudinal direction L is greater than the width dimension in the same direction of the alignment portion 72 of the first embodiment. The width dimension of the alignment portion 72 in the direction W crossing the longitudinal direction L is substantially equal to the length dimension of the rotational shaft 54.

As illustrated in FIG. 36 to FIG. 39, the alignment portion 72 includes an inclined surface 72A which gradually projects in an inward direction (direction toward the center axis C) toward the closing portion 83, and a track 72B extending from the inclined surface 72A in the longitudinal direction L. The inclined surface 72A guides the rotational shaft 54 to the bearing 65 side, when the cover 15 is attached to the distal structure portion 24. The track 72B pushes the rotational shaft 54 onto the bearing 65, when the cover 15 is attached to the distal structure portion 24. After the cover 15 was attached to the distal structure portion 24, the track 72B abuts on the rotational shaft 54 and aligns the rotational shaft 54 in a predetermined position (bottom 65A) in the bearing 65. Thus, the rotational shaft 54 of the pivot base 25 is rotatably supported in a so-called both-end support fashion, such that the rotational shaft 54 is clamped between the bearing 65 of the distal structure portion 24 and the alignment portion 72 of the cover 15 (see FIG. 36).

In the present embodiment, by the same method as in the first embodiment, the cover 15 is removed, the rotational shaft 54 is displaced from the bearing 65 (the rotational shaft 54 is lifted from the bottom 65A of the bearing 65), and the bearing 65 and rotational shaft 54 can be cleaned.

According to this embodiment, also when the alignment portion 72 has a wider width than in the first embodiment and is formed of one alignment portion, the cleaning performance of the bearing 65 and rotational shaft 54 can be improved at a time of maintenance. Thereby, the user-friendly endoscope 12 can be realized.

Eighth Embodiment

An eighth embodiment of the endoscope system 11 will be described with reference to FIG. 40 to FIG. 44.

As illustrated in FIG. 40 to FIG. 43, the main body 24A of the distal structure portion 24 includes a bearing 65 which rotatably holds the rotational shaft 54 of the pivot base 25; a guide portion 67 which guides a preventing portion 66 of the pivot base 25; and a restriction portion 68 which is provided to neighbor the guide portion 67 and restricts the rotational angle of the pivot base 25. The restriction portion 68 includes a first stopper 74 which restricts the rotational angle of the pivot base 25 on the fallen position P1 side of the pivot base 25, and a second stopper 75 which restricts the rotational angle of the pivot base 25 on the raised position P2 side of the pivot base 25.

The main body 24A includes a projecting piece 123 as a part thereof. The guide portion 67 is formed of an opening which is provided in a manner to penetrate the projecting piece 123. Alternatively, the guide portion 67 may be formed in a recess shape which does not penetrate the projecting piece 123 and is recessed from the surface of the projecting piece 123.

Figure 40:
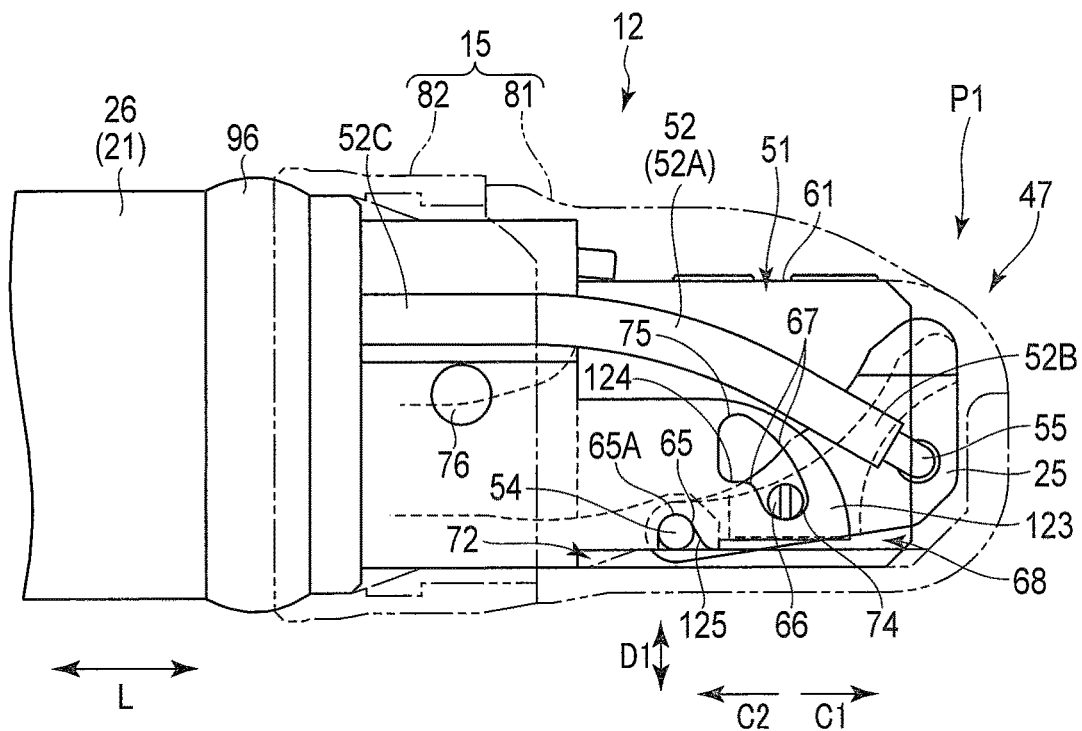
FIG. 40 is a side view illustrating a distal structure portion, cover and guide portion of an endoscope system of an eighth embodiment, FIG. 40 illustrating a state in which the pivot base is in the fallen position.
Figure 41:
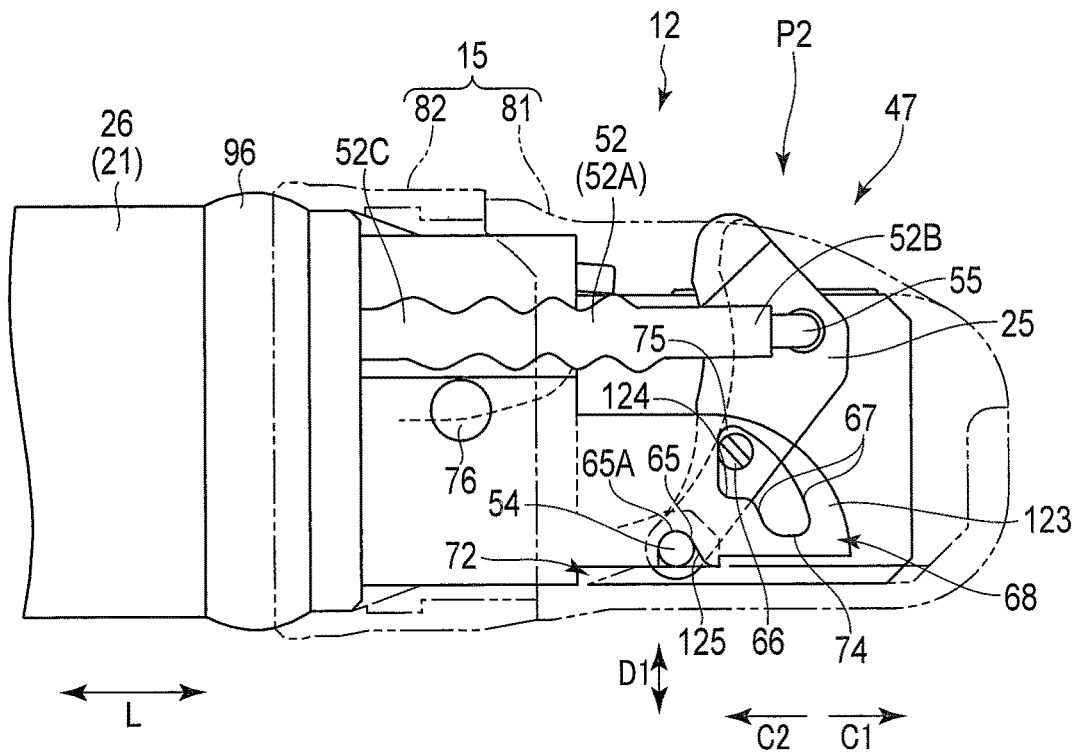
FIG. 41 is a side view illustrating a state in which the pivot base is in the raised position in the endoscope system illustrated in FIG. 40.

The guide portion 67 is formed in a groove shape along an arc having a center at the rotational shaft 54 which is in such a position that the rotational shaft 54 abuts on the bottom 65A of the bearing 65. The guide portion 67 includes a recess portion 124 which is recessed toward a direction in which the bearing 65 is present with respect to the arc. The recess portion 124 extends from the vicinity of the second stopper 75 in a direction toward the rotational shaft 54 (bearing 65) along a direction D1 in which the bearing 65 extends. Specifically, the recess portion 124 can guide the preventing portion 66 toward the direction in which the bearing 65 extends, when the pivot base 25 has rotated from the fallen position P1 by a predetermined angle, i.e. when the pivot base 25 is in the raised position P2. The guide portion 67 can guide the preventing portion 66 between a position at a time when the pivot base 25 is in the fallen position P1 as illustrated in FIG. 40 and a position at a time when the pivot base 25 is in the raised position P2 as illustrated in FIG. 41.

Unlike the first embodiment, the bearing 65 includes a notch portion 125 which is formed by obliquely cutting a portion of the bearing 65. The notch portion 125 is formed on the distal direction C1 side in the longitudinal direction L at a part which is in contact with the surface of the distal structure portion 24. In the present embodiment, by providing the bearing 65 with the notch portion 125, the rotational shaft 54 can be easily disengaged from the bearing 65.

As illustrated in FIG. 44, a second skirt portion 95 of the ferrule 82 constitutes a second alignment portion 126 which aligns the rotational shaft 54 that has dropped from the bearing 65, and the pivot base 25, in the bearing 65. Accordingly, by attaching the cover to the distal structure portion 24, the user can align the rotational shaft 54 and pivot base 25 in the predetermined position (bottom 65A) in the bearing 65 by the functions of the second alignment portion 126 and the alignment portion 72, without being aware of the position of the rotational shaft 54.

The user can remove the cover 15 by using the cover removing tool 16 by the same method as in the first embodiment.

The endoscope 12, from which the cover 15 was removed, that is, the insertion section 21 including the distal structure portion 24, the operation section 22 and the universal cord 23, are properly cleaned, disinfected and sterilized for reuse. In the present embodiment, as illustrated in FIG. 42 and FIG. 43, by displacing the rotational shaft 54 from the bearing 65 (by dropping the rotational shaft 54 from the bearing 65), the passage of a brush or the like is facilitated at a time of cleaning, and the cleaning performance of the distal structure portion 24 can be improved.

Figure 42:
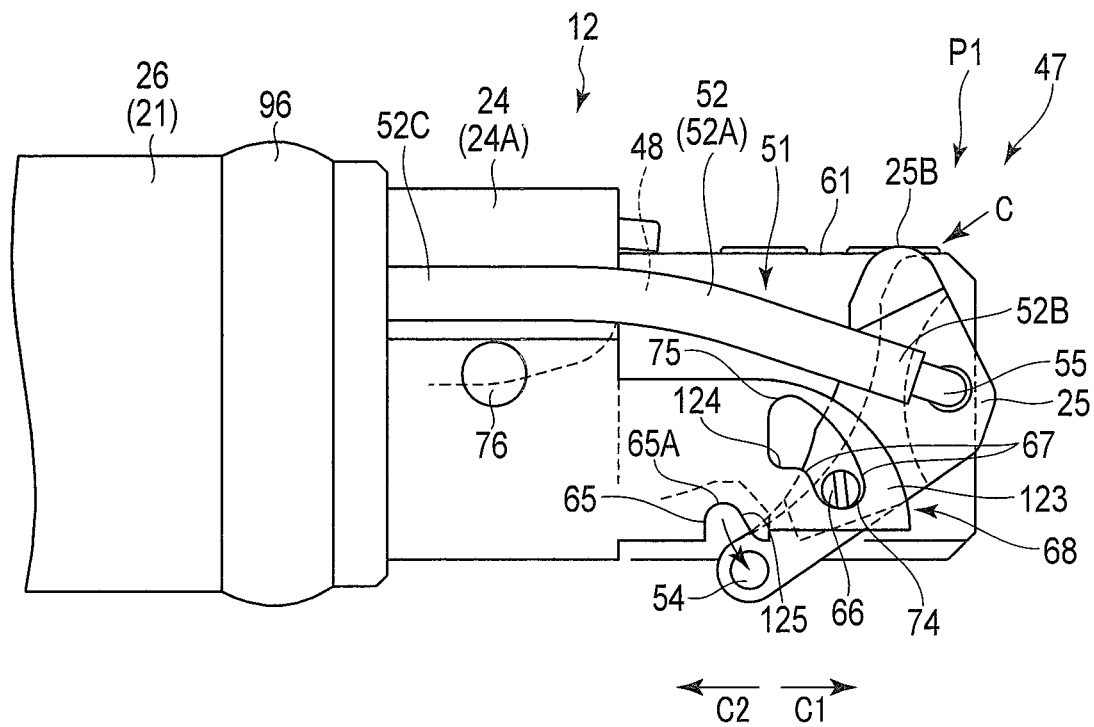
FIG. 42 is a side view illustrating a state in which the pivot base was pushed in a direction of an arrow C and the rotational shaft was displaced from the bearing, in a state in which the cover is removed in the endoscope system illustrated in FIG. 40.
Figure 43:
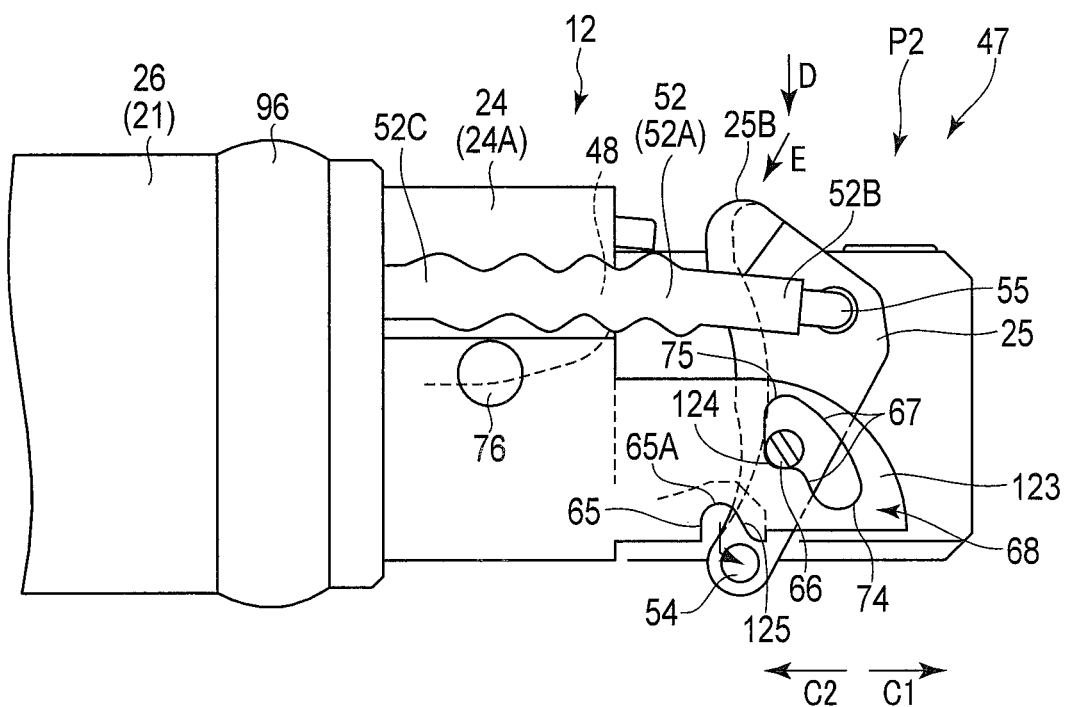
FIG. 43 is a side view illustrating a state in which the pivot base was pushed in directions of an arrow D and an arrow E and the rotational shaft was displaced from the bearing, in a state in which the cover is removed in the endoscope system illustrated in FIG. 41.

As illustrated in FIG. 42, in the state in which the pivot base 25 is in the fallen position P1, the user pushes the vicinity of the distal end portion 25B of the pivot base 25 from a direction indicated by an arrow C. Thereby, the rotational shaft 54 can be displaced (dropped) from the bearing 65. As illustrated in FIG. 43, in the state in which the pivot base 25 is in the raised position P2, if the user pushes the vicinity of the distal end portion 25B of the pivot base 25 from a direction indicated by an arrow D, the preventing portion 66 is moved into the recess portion 124, and the rotational shaft 54 is displaced (dropped) from the bearing 65. Thereafter, the user pushes the vicinity of the distal end portion 25B of the pivot base 25 from a direction indicated by an arrow E, and thereby the rotational shaft 54 can completely be displaced (dropped) from the bearing 65.

In this manner, in this embodiment, in each of the states of the fallen position P1 and raised position P2, the rotational shaft 54 can be displaced from the bearing 65. Thus, the passage of a brush or the like can be facilitated for the bearing 65 and rotational shaft 54, and usability is high for the user who cleans the bearing 65 and rotational shaft 54. After the cleaning, disinfection and sterilization are performed, and a new cover 15 is properly attached to the distal structure portion 24. Thereby, the endoscope system 11 is used for the next-time observation and treatment. Moreover, in this embodiment, as illustrated in FIG. 44, the second skirt portion 95 of the ferrule 82 of the cover 15 abuts on the pivot base 25 (pivot base body 71), and the rotational shaft 54 is positioned in the bearing 65. In this manner, since the second skirt portion 95 functions as the second alignment portion 126, the user can align the rotational shaft 54 in the predetermined position (bottom 65A) in the bearing 65 when attaching the cover 15, without being aware of the alignment.

According to the present embodiment, the guide portion 67 includes the recess portion 124 which can guide the preventing portion 66 toward the direction in which the bearing 65 extends, when the rotational portion has rotated by a predetermined angle. The rotational shaft 54 is displaced from the bearing 65 when the preventing portion 66 is moved into the recess portion 124 in the state in which the exterior member is removed from the distal structure portion 24.

According to this configuration, in the state in which the rotational portion has rotated by a predetermined angle, the rotational shaft 54 can be displaced from the bearing 65 by using the recess portion 124. Thus, the rotational shaft 54 can be displaced from the bearing 65 in both of the state in which the pivot base 25 is in the initial position (fallen position P1) and the state in which the pivot base 25 is rotated by the predetermined angle (in the raised position P2), and the bearing 65 and rotational shaft 54 can easily be cleaned by a brush or the like at the time of maintenance. In addition, compared to the first embodiment in which the gap is created between the bottom 65A of the bearing 65 and the rotational shaft 54, the passage of the brush or the like can be made still easier for the bearing 65 and rotational shaft 54, and workability is improved at a time of cleaning. Thereby, a more user-friendly endoscope 12 can be realized.

The exterior member includes the alignment portions 72 and 126. When the exterior member is attached to the distal structure portion 24, the alignment portions 72 and 126 align the rotational shaft 54 in the predetermined position in the bearing 65.

According to this configuration, when the exterior member is attached, the rotational shaft 54, even if displaced, can be aligned by the alignment portions 72 and 126. Thereby, the rotational shaft 54 can be aligned in the original position without making the user aware of the alignment, and a still more user-friendly endoscope 12 can be realized.

Ninth Embodiment

A ninth embodiment of the endoscope system 11 will be described with reference to FIG. 45 to FIG. 49.

The main body 24A of the distal structure portion 24 includes a bearing 65 which rotatably holds the rotational shaft 54 of the pivot base 25; a guide portion 67 which guides a preventing portion 66 of the pivot base 25; and a restriction portion 68 which is provided to neighbor the guide portion 67 and restricts the rotational angle of the pivot base 25. The restriction portion 68 includes a first stopper 74 which restricts the rotational angle of the pivot base 25 on the fallen position P1 side of the pivot base 25, and a second stopper 75 which restricts the rotational angle of the pivot base 25 on the raised position P2 side of the pivot base 25.

As illustrated in FIG. 45 to FIG. 48, the main body 24A includes a projecting piece 123 as a part thereof. The guide portion 67 is formed of an opening which is provided in a manner to penetrate the projecting piece 123. Alternatively, the guide portion 67 may be formed in a recess shape which does not penetrate the projecting piece 123 and is recessed from the surface of the projecting piece 123.

The guide portion 67 is formed in a groove shape along an arc having a center at the rotational shaft 54 which is in such a position that the rotational shaft 54 abuts on the bottom 65A of the bearing 65. The width dimension of the guide portion 67 with respect to the direction D1 in which the bearing 65 extends is greater than the diameter of the preventing portion 66, and is less than double the dimension of the diameter of the preventing portion 66. The width dimension of the guide portion 67 with respect to the direction D1 is set such that the preventing portion 66 can advance/retreat over a small distance with respect to the direction D1. Accordingly, the guide portion 67 can guide the preventing portion 66 toward the direction D1 in which the bearing 65 extends, when the pivot base 25 has rotated from the fallen position P1 by a predetermined angle, i.e. when the pivot base 25 is in the raised position P2.

Unlike the first embodiment, the bearing 65 includes a notch portion 125 which is formed by obliquely cutting a portion of the bearing 65. The notch portion 125 is formed on the distal direction C1 side in the longitudinal direction L at a part which is in contact with the surface of the distal structure portion 24. In the present embodiment, by providing the bearing 65 with the notch portion 125, the rotational shaft 54 can easily be disengaged from the bearing 65.

Figure 49:
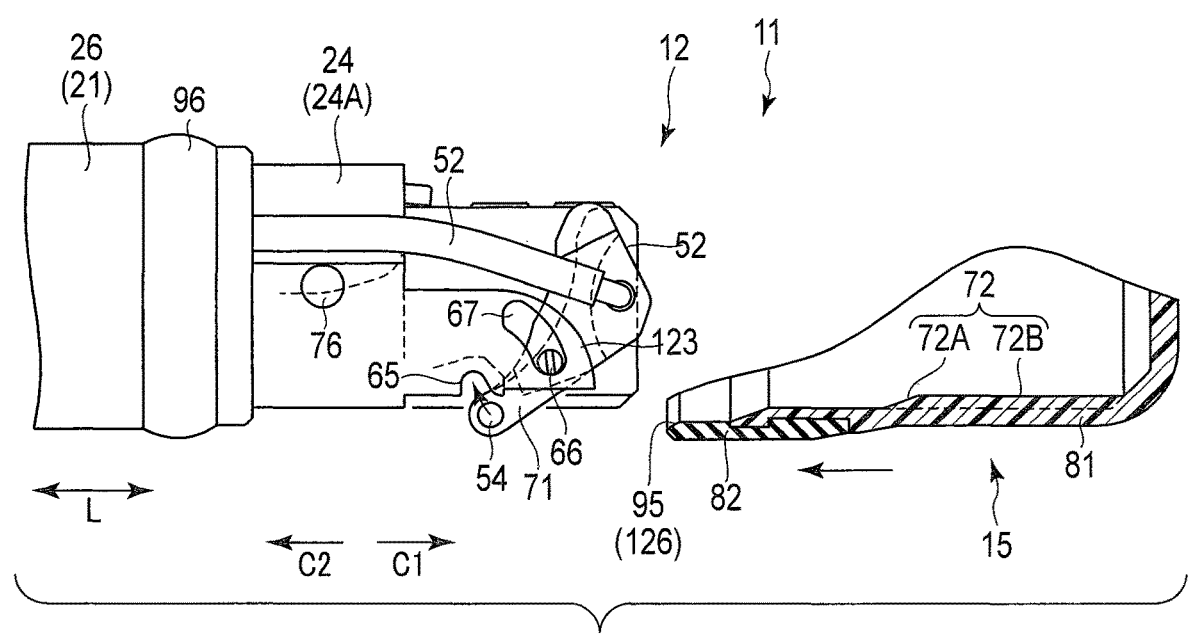
FIG. 49 is a side view illustrating a step of attaching the cover to the distal structure portion in the endoscope system illustrated in FIG. 45.

As illustrated in FIG. 49, a second skirt portion 95 of the ferrule 82 constitutes a second alignment portion 126 which aligns the rotational shaft 54 that has dropped from the bearing 65, and the pivot base 25, in the bearing 65. Accordingly, by attaching the cover to the distal structure portion 24, the user can align the rotational shaft 54 and pivot base 25 in the predetermined position (bottom 65A) in the bearing 65 by the functions of the second alignment portion 126 and the alignment portion 72, without being aware of the position of the rotational shaft 54.

The user can remove the cover 15 by using the cover removing tool 16 by the same method as in the first embodiment.

The endoscope, from which the cover 15 was removed, that is, the insertion section 21 including the distal structure portion 24, the operation section 22 and the universal cord 23, are properly cleaned, disinfected and sterilized for reuse. In the present embodiment, as illustrated in FIG. 47 and FIG. 48, by displacing the rotational shaft 54 from the bearing 65 (by dropping the rotational shaft 54 from the bearing 65, or by lifting the rotational shaft 54 from the bottom 65A of the bearing 65), the passage of a brush or the like is facilitated at a time of cleaning, and the cleaning performance of the distal structure portion 24 can be improved.

As illustrated in FIG. 47, in the state in which the pivot base 25 is in the fallen position P1, the user pushes the vicinity of the distal end portion 25B of the pivot base 25 from the direction indicated by the arrow C. Thereby, the rotational shaft 54 can be displaced (dropped) from the bearing 65. As illustrated in FIG. 48, in the state in which the pivot base 25 is in the raised position P2, the user pushes the vicinity of the distal end portion 25B of the pivot base 25 from the direction indicated by the arrow D. Thereby, the rotational shaft 54 can be displaced from the bottom 65A of the bearing 65 (can be lifted from the bottom 65A of the bearing 65) by a length corresponding to a dimension G3.

In this manner, in this embodiment, the rotational shaft 54 can be dropped from the bearing 65 in the fallen position P1, or the rotational shaft 54 can be lifted from the bottom 65A of the bearing 65 in the raised position P2. Thus, in each of the fallen position P1 and raised position P2, the passage of a brush or the like can be facilitated for the bearing 65 and rotational shaft 54, and usability is high for the user who cleans the bearing 65 and rotational shaft 54. After the cleaning, disinfection and sterilization are performed, and a new cover 15 is properly attached to the distal structure portion 24. Thereby, the endoscope system 11 is used for the next-time observation and treatment. Moreover, in this embodiment, as illustrated in FIG. 49, the second skirt portion 95 of the ferrule 82 of the cover 15 abuts on the pivot base 25 (pivot base body 71), and the rotational shaft 54 is positioned in the bearing 65. In this manner, since the second skirt portion 95 functions as the second alignment portion 126, the user can align the rotational shaft 54 in the predetermined position (bottom 65A) in the bearing 65 when attaching the cover 15, without being aware of the alignment.

According to the present embodiment, the guide portion 67 is formed of an opening having a groove shape along an arc having a center at the rotational shaft 54 which is in such a position that the rotational shaft 54 abuts on the bottom 65A of the bearing 65. The width dimension of the guide portion 67 with respect to the direction D1 in which the bearing 65 extends is greater than the diameter of the preventing portion 66, and is less than double the dimension of the diameter of the preventing portion 66. According to this configuration, when the pivot base 25 has rotated by a predetermined angle from the fallen position P1, the rotational shaft 54 can be lifted from the bottom 65A of the bearing 65. Besides, when the pivot base 25 is in the fallen position P1, the rotational shaft 54 can be dropped from the bearing 65. Thereby, the bearing 65 and rotational shaft 54 can easily be cleaned by a brush or the like at the time of maintenance. Therefore, a more user-friendly endoscope 12 can be realized.

Tenth Embodiment

A tenth embodiment of the endoscope system 11 will be described with reference to FIG. 50 to FIG. 55.

As illustrated in FIG. 50 to FIG. 53, the main body 24A of the distal structure portion 24 includes a bearing 65 which rotatably holds the rotational shaft 54 of the pivot base 25; a guide portion 67 which guides a preventing portion 66 of the pivot base 25; a restriction portion 68 which is provided to neighbor the guide portion 67 and restricts the rotational angle of the pivot base 25; and a missing portion 131 which is formed in a part of the guide portion 67 and can release, at this position, the guiding of the preventing portion 66. The restriction portion 68 includes a first stopper 74 which restricts the rotational angle of the pivot base 25 on the fallen position P1 side of the pivot base 25, and a second stopper 75 which restricts the rotational angle of the pivot base 25 on the raised position P2 side of the pivot base 25.

The main body 24A includes a projecting piece 123 as a part thereof. The guide portion 67 is formed of an opening which is provided in a manner to penetrate the projecting piece 123. Alternatively, the guide portion 67 may be formed in a recess shape which does not penetrate the projecting piece 123 and is recessed from the surface of the projecting piece 123.

The guide portion 67 is formed in a groove shape along an arc having a center at the rotational shaft 54 which is in such a position that the rotational shaft 54 abuts on the bottom 65A of the bearing 65. The guide portion 67 can guide the preventing portion 66 between a position at a time when the pivot base 25 is in the fallen position P1 as illustrated in FIG. 50 and a position at a time when the pivot base 25 is in the raised position P2 as illustrated in FIG. 51.

The missing portion 131 is formed by removing a part of a ring of an edge portion which defines the surrounding of the guide portion 67. Specifically, as illustrated in FIG. 52, etc., the missing portion 131 is formed by removing a part of the ring of the edge portion on the distal direction C1 side of the longitudinal direction L in that part of the edge portion of the surrounding of the guide portion 67, which neighbors the first stopper 74 (i.e. at the position corresponding to the preventing portion 66 when the pivot base 25 is in the fallen position P1).

The bearing 65 includes a notch portion 125 which is formed by obliquely cutting a portion of the bearing 65. The notch portion 125 is formed on the distal direction C1 side in the longitudinal direction L at a part which is in contact with the surface of the distal structure portion 24. In the present embodiment, by providing the bearing 65 with the notch portion 125, the rotational shaft 54 can easily be disengaged from the bearing 65.

Figure 50:
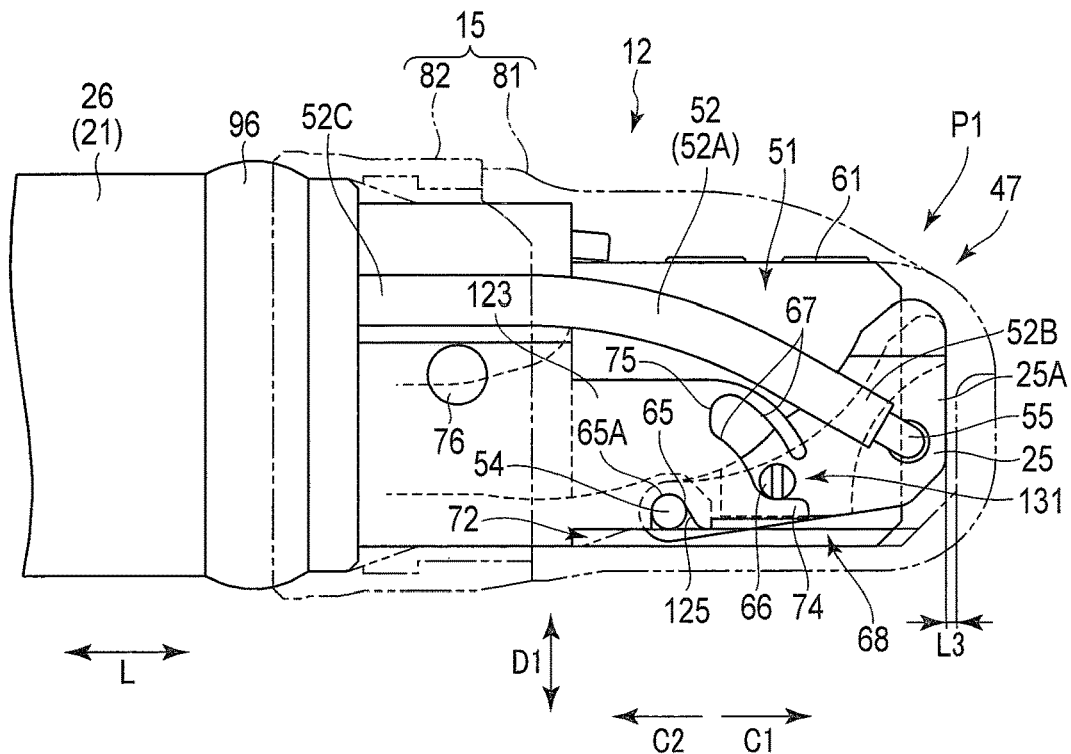
FIG. 50 is a side view illustrating a distal structure portion, cover and guide portion of an endoscope system of a tenth embodiment, FIG. 50 illustrating a state in which the pivot base is in the fallen position.
Figure 51:
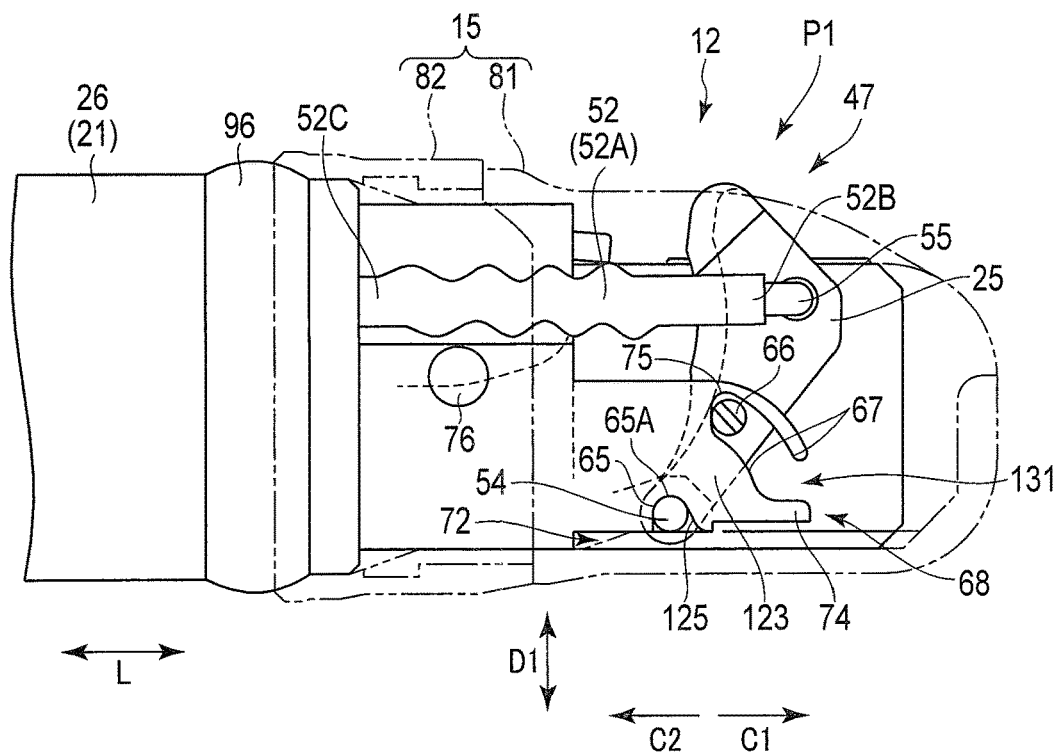
FIG. 51 is a side view illustrating a state in which the pivot base is in the raised portion in the endoscope system illustrated in FIG. 50.

As illustrated in FIG. 50, only a small gap L3 is present between the distal surface 25A of the pivot base 25 and the inner surface of the closing portion 83 of the cover 15. Thus, in the state in which the cover 15 is attached to the distal structure portion 24, even if the rotational shaft 54 drops from the bearing 65 due to some cause, the distal surface 25A of the pivot base 25 abuts on the inner surface of the closing portion 83. Thus, even in such a case, it is possible to prevent the pivot base 25 from dropping from the distal structure portion 24, with the preventing portion 66 being displaced to the distal direction C1 side via the missing portion 131.

Figure 55:
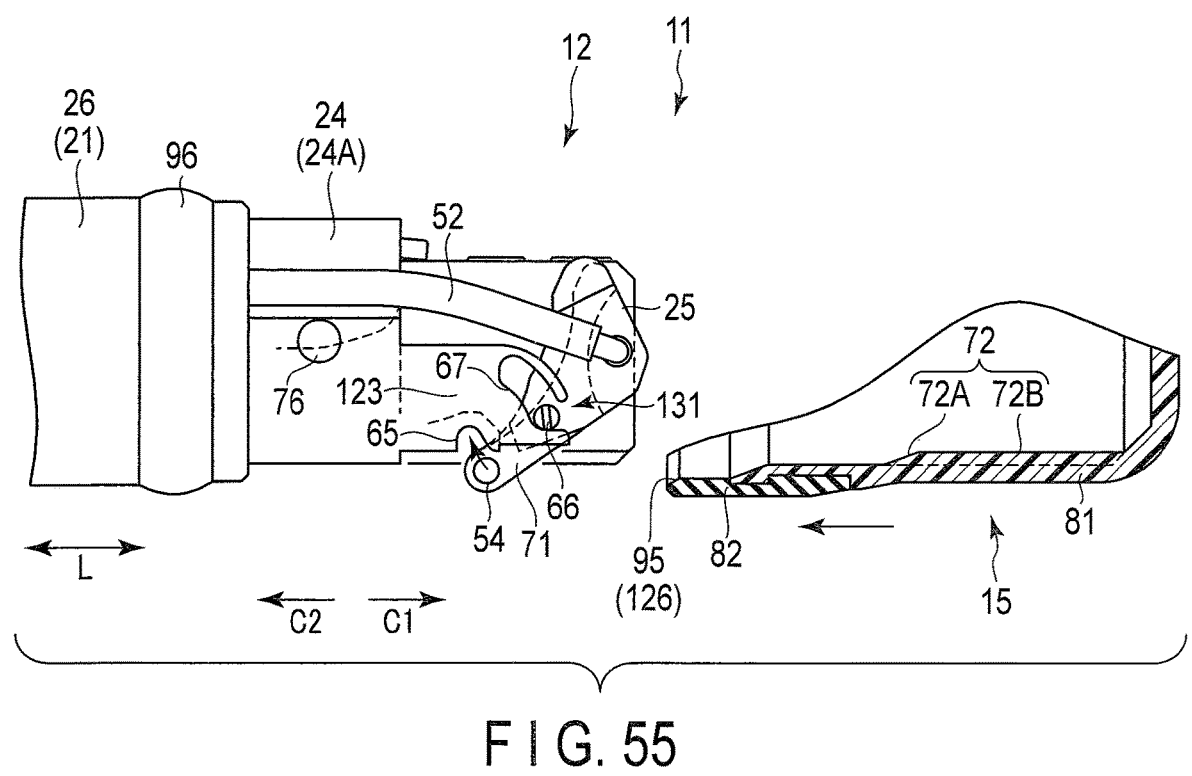
FIG. 55 is a side view illustrating a step of attaching the cover to the distal structure portion in the endoscope system illustrated in FIG. 50.

As illustrated in FIG. 55, a second skirt portion 95 of the ferrule 82 of the cover 15 constitutes a second alignment portion 126 which aligns the rotational shaft 54 that has dropped from the bearing 65, and the pivot base 25, in the bearing 65. Accordingly, by attaching the cover 15 to the distal structure portion 24 in the state in which the rotational shaft 54 is restored in the guide portion 67 via the missing portion 131, the user can align the rotational shaft 54 and pivot base 25 in the predetermined position (bottom 65A) in the bearing 65 by the functions of the second alignment portion 126 and the alignment portion 72.

The user can remove the cover 15 by using the cover removing tool 16 by the same method as in the first embodiment.

The endoscope 12, from which the cover 15 was removed, that is, the insertion section 21 including the distal structure portion 24, the operation section 22 and the universal cord 23, are properly cleaned, disinfected and sterilized for reuse. In the present embodiment, as illustrated in FIG. 52 and FIG. 53, by displacing the rotational shaft 54 from the bearing 65 (by dropping the rotational shaft 54 from the bearing 65, or by lifting the rotational shaft 54 from the bottom 65A of the bearing 65), the passage of a brush or the like is facilitated at a time of cleaning, and the cleaning performance of the distal structure portion 24 can be improved.

Figure 54:
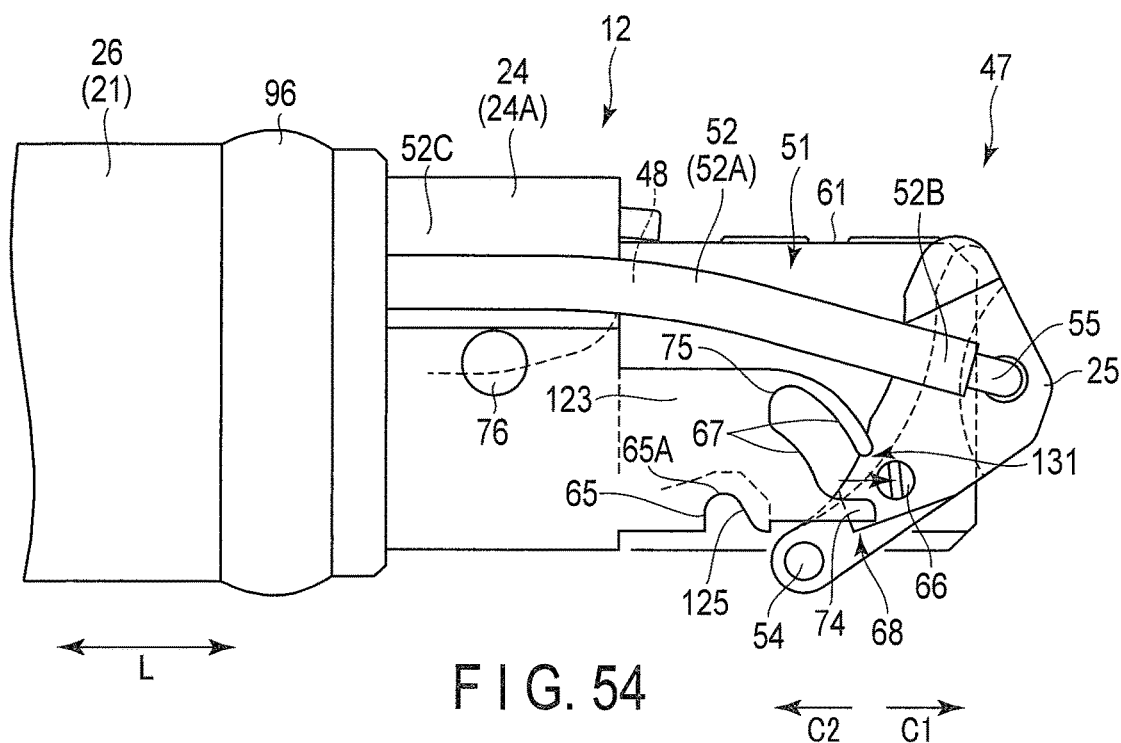
FIG. 54 is a side view illustrating a preventing portion was dropped via a missing portion and the pivot base was disengaged from the distal structure portion, in a state in which the cover is removed from the endoscope system illustrated in FIG. 50.

As illustrated in FIG. 52, in the state in which the pivot base 25 is in the fallen position P1, the user pushes the vicinity of the distal end portion 25B of the pivot base 25 from the direction indicated by the arrow C. Thereby, the rotational shaft 54 can be dropped from the bearing 65. As illustrated in FIG. 53, in the state in which the pivot base 25 is in the raised position P2, the user pushes the vicinity of the distal end portion 25B of the pivot base 25 from the direction indicated by the arrow D. Thereby, the rotational shaft 54 can be lifted from the bottom 65A of the bearing 65 by a length corresponding to a dimension G4. Furthermore, as illustrated in FIG. 54, the user can drop the preventing portion 66 from the guide portion 67 via the missing portion 131, and can disengage the pivot base 25 from the distal structure portion 24. Thereby, the cleaning performance of not only the vicinity of the bearing 65 and rotational shaft 54, but also the vicinity of the pivot base 25, guide portion 67 and preventing portion 66, is improved.

In this manner, in this embodiment, in each of the states of the fallen position P1 and raised position P2, the rotational shaft 54 can be displaced (dropped or lifted) from the bearing 65. Thus, the passage of a brush or the like can be facilitated for the bearing 65 and rotational shaft 54, and usability is high for the user who cleans the bearing 65 and rotational shaft 54. After the cleaning, disinfection and sterilization are performed, and a new cover 15 is properly attached to the distal structure portion 24. Thereby, the endoscope system 11 is used for the next-time observation and treatment. Moreover, in this embodiment, from the state illustrated in FIG. 54, the preventing portion 66 is restored in the guide portion 67 via the missing portion 131 by the user's hand, as illustrated in FIG. 55. In this state, when the new cover 15 is attached to the distal structure portion 24, the second skirt portion 95 of the ferrule 82 of the cover 15 abuts on the pivot base 25 (pivot base body 71). Thereby, the rotational shaft 54 is positioned in the bearing 65. In this manner, since the second skirt portion 95 functions as the second alignment portion 126, the user can align the rotational shaft 54 in the predetermined position (bottom 65A) in the bearing 65 when attaching the cover 15, without being aware of the alignment.

According to the present embodiment, the preventing portion 66 is provided on the rotational portion, and the guide portion 67 includes the missing portion 131 which can release the guiding of the preventing portion 66. According to this configuration, by releasing the guiding of the preventing portion 66 via the missing portion 131, the rotational portion can be disengaged from the distal structure portion 24. In the state in which the rotational portion is disengaged in this manner, the rotational portion, rotational shaft 54, bearing 65, guide portion 67, etc. can easily be cleaned by a brush or the like. Therefore, at the time of maintenance, the cleaning performance of these parts can be further improved, and a more user-friendly endoscope 12 can be realized.

Eleventh Embodiment

An eleventh embodiment of the endoscope system 11 will be described with reference to FIG. 56 to FIG. 61.

As illustrated in FIG. 56, the restriction portion 68 has substantially the same configuration as in the above-described second embodiment.

The pivot base 25 is pivotable relative to the bearing 65 of the main body 24A, with the rotational shaft 54 functioning as the fulcrum. The pivot base 25 is an example of the rotational portion which rotates about the rotational shaft 54. The pivot base 25 includes a pivot base body 71 having a substantially triangular shape or a boomerang shape; the rotational shaft 54 which is formed integral with the pivot base body 71; an auxiliary plate 132 which is formed integral with the pivot base body 71; and a guide portion 67 formed in the auxiliary plate 132. The rotational shaft 54 is provided to project on both sides in a direction crossing the longitudinal direction C from the pivot base body 71 of the pivot base 25. Thus, the rotational shaft 54 of the pivot base 25 is rotatably supported in a so-called both-end support fashion, such that the rotational shaft 54 is clamped between the bearing 65 of the distal structure portion 24 and the alignment portion 72 of the cover 15 (see FIG. 58). In the present embodiment, the preventing portion 66 is provided on the distal structure portion 24 side. The preventing portion 66 is put in contact with the guide portion 67 of the pivot base 25 (rotational portion), thereby preventing the pivot base 25 from being disengaged from the distal structure portion 24. In addition, the auxiliary plate 132 and pivot base body 71 are fixed by, for example, an adhesive or the like. Besides, instead of providing the auxiliary plate 132, the side surface of the pivot base body 71 may be formed to have the same shape as the guide portion 67 of the auxiliary plate 132.

The guide portion 67 is formed in a groove shape recessed from the surface of the auxiliary plate 132. The preventing portion 66, which prevents the dropping of the pivot base 25, can be received in the inside of the guide portion 67. The guide portion 67 has an arcuate shape having a center at the rotational shaft 54. The guide portion 67 can guide the preventing portion 66 between a position at a time when the pivot base 25 is in the fallen position P1 as illustrated in FIG. 58 and a position at a time when the pivot base 25 is in the raised position P2 as illustrated in FIG. 59.

The main body 24A of the distal structure portion 24 includes a projecting piece 123 which is provided as a part thereof, and the preventing portion 66 which prevents the rotational shaft 54 from dropping from the bearing 65. As illustrated in FIG. 56, the preventing portion 66 is composed of a stepped pin (a distal portion of a pin) which is fixed in a through-hole 133 provided in the projecting piece 123. The stepped pin (preventing portion 66) is fixed to the projecting piece 123 by brazing using a solder or the like. However, the fixing method of the stepped pin is not limited to this. The stepped pin (preventing portion 66) may be fixed to the projecting piece 123 by an adhesive, may be fixed by press-fitting the rotational shaft 54 into the through-hole 133, or may be fixed by welding to the through-hole 133.

The preventing portion 66 cooperates with the guide portion 67 and wire 48, thereby defining a distance of lifting of the rotational shaft 54 from the bottom 65A of the bearing 65. Specifically, the structure of the preventing portion 66 and guide portion 67 prevents the rotational shaft 54 from dropping from the bearing 65, and prevents the pivot base 25 from dropping from the distal structure portion 24.

The user can remove the cover 15 by using the cover removing tool 16 by the same method as in the first embodiment.

The endoscope 12, from which the cover 15 was removed, that is, the insertion section 21 including the distal structure portion 24, the operation section 22 and the universal cord 23, are properly cleaned, disinfected and sterilized for reuse. In the present embodiment, as illustrated in FIG. 60 and FIG. 61, the rotational shaft 54 can be displaced from the bearing 65 (the rotational shaft 54 can be lifted from the bottom 65A of the bearing 65).

Figure 60:
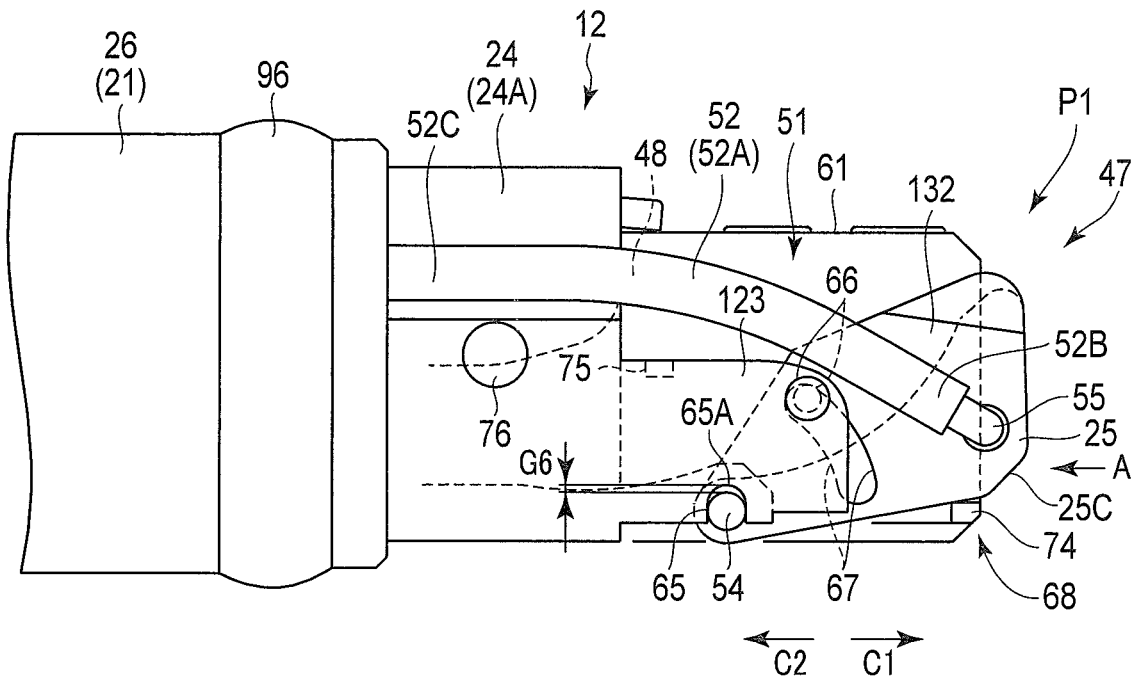
FIG. 60 is a side view illustrating a state in which the pivot base was pushed in the direction of the arrow A and the rotational shaft was displaced from the bearing, in a state in which the cover is removed in the endoscope system illustrated in FIG. 58.
Figure 61:
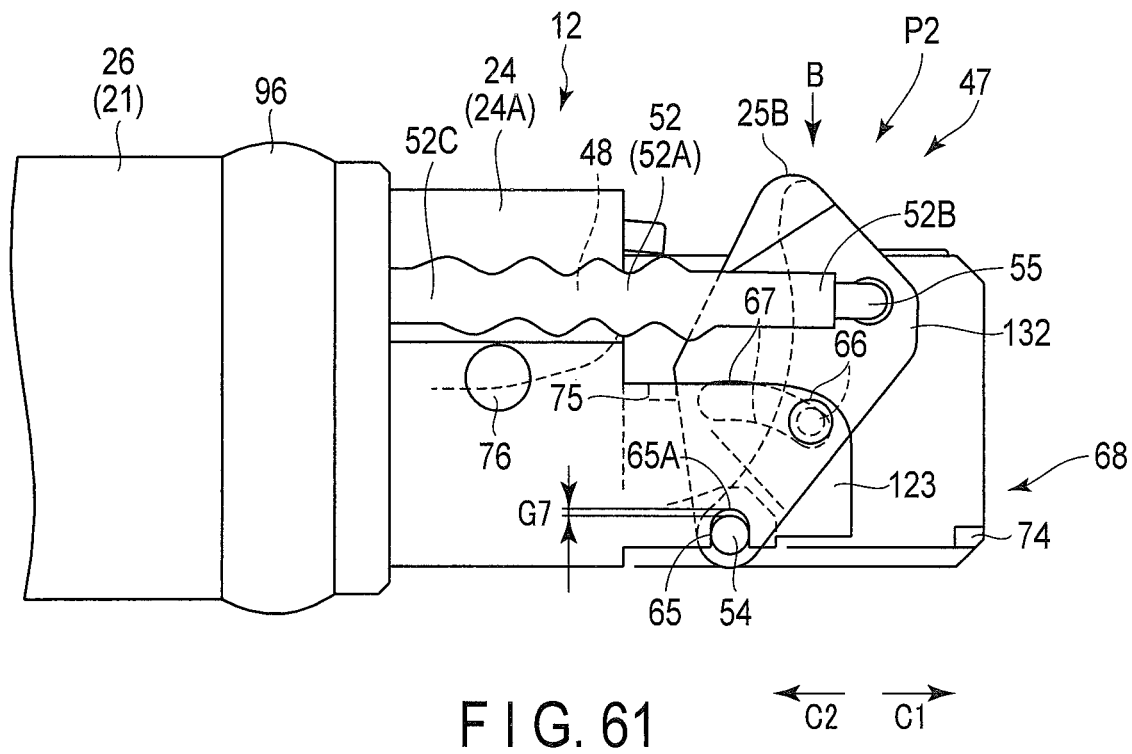
FIG. 61 is a side view illustrating a state in which the pivot base was pushed in the direction of the arrow B and the rotational shaft was displaced from the bearing, in a state in which the cover is removed in the endoscope system illustrated in FIG. 59.

As illustrated in FIG. 60, in the state in which the pivot base 25 is in the fallen position P1, the user pushes the vicinity of the distal chamfered portion 25C of the pivot base 25 from the direction indicated by the arrow A. Thereby, the rotational shaft 54 can be lifted from the bottom 65A of the bearing 65 by a length corresponding to a dimension G6. As illustrated in FIG. 61, in the state in which the pivot base 25 is in the raised position P2, the user pushes the vicinity of the distal end portion 25B of the pivot base 25 from the direction indicated by the arrow B. Thereby, the rotational shaft 54 can be lifted from the bottom 65A of the bearing 65 by a length corresponding to a dimension G7.

In this manner, in this embodiment, in each of the states of the fallen position P1 and raised position P2, the rotational shaft 54 can be displaced (lifted) from the bearing 65. Thus, the passage of a brush or the like can be facilitated for the bearing 65 and rotational shaft 54, and usability is high for the user who cleans the bearing 65 and rotational shaft 54. After the cleaning, disinfection and sterilization are performed, and a new cover 15 is properly attached to the distal structure portion 24. Thereby, the endoscope system 11 is used for the next-time observation and treatment.

According to the present embodiment, the preventing portion 66 is provided on the distal structure portion 24 side, and the guide portion 67 is provided on the rotational portion (pivot base 25) side. Also with this configuration, the cleaning performance of the bearing 65 and rotational shaft 54 can be improved, and the user-friendly endoscope 12 can be realized.

In each of the above-described embodiments and modifications, the example in which the distal structure portion 24 is of a side-viewing type was described. However, needless to say, the distal structure portion 24 may be formed as a so-called forward-viewing type for observation in a direction along the longitudinal direction L of the insertion section 21, or may be formed as an oblique-viewing type for observation in an arbitrary direction in a range between the direction along the longitudinal axis L of the insertion section 21 and the direction perpendicular to the longitudinal axis L.

Although some embodiments were concretely described above with reference to the accompanying drawings, the present invention is not limited to the above embodiments, and the structural elements can be modified and embodied without departing from the spirit of the invention. Besides, the structural elements in the above-described different embodiments may be properly combined to realize one endoscope system 11 or endoscope 12.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:
1. An endoscope comprising:
a distal structure portion provided on a distal side of an insertion section;
a rotational portion including a rotational shaft which is held to be rotatable relative to the distal structure portion, and configured to rotate about the rotational shaft;
a bearing recessed from an outer surface of the distal structure portion in a direction intersecting an axial direction of the rotation shaft, the bearing being configured to receive and support the rotational shaft in a manner that the rotational shaft may be displaced from the distal structure portion;
a preventing surface provided on one of the rotational portion and the distal structure portion, the preventing surface being configured to prevent disengagement of the rotational portion by coming in contact with an other of the rotational portion and the distal structure portion; and
an exterior member detachably attached to the distal structure portion, wherein the bearing is opposed to the exterior member, the bearing is configured to displace the rotational shaft relative to the distal structure portion in a direction intersecting the axial direction of the rotational shaft without disengagement of the rotational shaft from the bearing when the exterior member is detached from the distal structure portion.

2. The endoscope of claim 1, wherein the preventing surface is configured to prevent the disengagement of the rotational portion in a position in which the rotational portion is not raised relative to the distal structure portion.

3. The endoscope of claim 1, further comprising a guide surface configured to guide the preventing surface when the rotational portion is rotated relative to the distal structure portion.

4. The endoscope of claim 3, further comprising a restriction surface configured to restrict a range of rotation of the rotational portion relative to the distal structure portion.

5. The endoscope of claim 3, wherein the preventing surface is provided on the rotational portion, and
the guide surface includes an opening configured to release guiding of the preventing surface.

6. The endoscope of claim 5, wherein the guide surface includes a recess portion configured to guide the preventing surface toward a direction in which the bearing extends, when the rotational portion is rotated by a predetermined angle, and the rotational shaft is displaced from the bearing when the preventing surface is moved into the recess portion in a state in which the exterior member is removed from the distal structure portion.

7. The endoscope of claim 1, wherein the exterior member includes an alignment surface, the alignment surface being configured to align the rotational shaft in a predetermined position in the bearing when the exterior member is attached to the distal structure portion.

8. The endoscope of claim 7, wherein when the exterior member is attached to the distal structure portion in a direction along a longitudinal direction of the insertion section, the alignment surface allows the movement of the rotational shaft in a direction crossing the longitudinal direction, and aligns the rotational shaft in the predetermined position in the bearing.

9. The endoscope of claim 8, wherein the alignment surface includes, on an inner surface of the exterior member, an inclined surface which projects toward a distal structure portion side, the inclined surface being configured to guide the rotational shaft to the predetermined position in the bearing when the exterior member is attached to the distal structure portion.

10. The endoscope of claim 9, wherein the alignment surface includes, on the inner surface of the exterior member, a track which projects toward the distal structure portion side and is continuous with the inclined surface, the track being configured to hold the rotational shaft in the predetermined position in the bearing.

11. The endoscope of claim 1, wherein a dimension of the bearing in a longitudinal direction of the insertion section is greater than a dimension of the bearing in a direction crossing the longitudinal direction of the insertion section.

12. The endoscope of claim 1, wherein the exterior member is a jacket which covers the distal structure portion when the exterior member is attached to the distal structure portion.

13. The endoscope of claim 1, further comprising an alignment surface provided on the exterior member and configured to move, when the exterior member is attached to the distal structure portion, the rotational shaft in a direction crossing a longitudinal direction of the insertion section, and to align the rotational shaft in a predetermined position in the bearing.

14. An endoscope system comprising:
the endoscope of claim 1; and
an exterior member removing tool which is rotatable relative to the exterior member, the exterior member removing tool including a bottom portion which abuts on a distal end of the exterior member, a cylindrical portion which projects from the bottom portion and is configured to cover a periphery of the exterior member, and an abutment portion which is provided in an inside of the cylindrical portion, abuts on an opening portion provided in the exterior member when the exterior member removing tool is rotated relative to the exterior member, and breaks a fragile portion of the exterior member,
wherein a dimension in the longitudinal direction of the insertion section from the bottom portion to an end face of the cylindrical portion is greater than a dimension in the longitudinal direction from the bottom portion to the rotational shaft, and is less than a dimension in the longitudinal direction from the bottom portion to the fragile portion of the exterior member.

15. An endoscope comprising:
a distal structure portion provided on a distal side of an insertion section;
a rotational portion including a rotational shaft which is held to be rotatable relative to the distal structure portion, and configured to rotate about the rotational shaft;
a bearing recessed from an outer surface of the distal structure portion in a direction intersecting an axial direction of the rotational shaft, the bearing comprising a slot open to the outer surface of the distal structure portion, the rotational shaft being movable within the slot relative to the distal structure portion, the bearing supporting the rotation shaft such that the rotational shaft is configured to be displaced relative to the distal structure portion in the direction intersecting the axial direction; and
a preventing surface provided on one of the rotational portion and the distal structure portion, the preventing surface being configured to prevent disengagement of the rotational portion by coming in contact with an other of the rotational portion and the distal structure portion;
wherein a shortest distance between the preventing surface and the rotational shaft is shorter than a shortest distance between the preventing surface and an exterior corner of the slot of the bearing that is closest to the preventing surface.

16. The endoscope of claim 1, wherein a shortest distance between the preventing surface and rotational shaft is shorter than a shortest distance between the preventing surface and an exterior corner of the slot of the bearing that is closest to the preventing surface.

* * * * *